(12) United States Patent
Jackson et al.

(10) Patent No.: US 12,076,055 B2
(45) Date of Patent: Sep. 3, 2024

(54) PIVOTAL BONE ANCHOR ASSEMBLY WITH FAVORED-ANGLE RECEIVER HAVING UPPER TOOL ENGAGEMENT GROOVES AND BREAK-OFF EXTENSIONS

(71) Applicant: Roger P. Jackson, Prairie Village, KS (US)

(72) Inventors: Roger P. Jackson, Prairie Village, KS (US); James L Surber, Kansas City, KS (US)

( * ) Notice: Subject to any disclaimer, the term of this patent is extended or adjusted under 35 U.S.C. 154(b) by 155 days.

(21) Appl. No.: 17/736,295

(22) Filed: May 4, 2022

(65) Prior Publication Data

US 2022/0257290 A1 Aug. 18, 2022

Related U.S. Application Data

(63) Continuation of application No. 17/113,984, filed on Dec. 7, 2020, now Pat. No. 11,337,735, which is a
(Continued)

(51) Int. Cl.
| | |
|---|---|
| *A61B 17/70* | (2006.01) |
| *A61B 17/86* | (2006.01) |
| *A61B 90/00* | (2016.01) |

(52) U.S. Cl.
CPC ...... *A61B 17/7037* (2013.01); *A61B 17/7032* (2013.01); *A61B 17/7035* (2013.01);
(Continued)

(58) Field of Classification Search
CPC .................................................. A61B 17/7037
See application file for complete search history.

(56) References Cited

U.S. PATENT DOCUMENTS

| | | | |
|---|---|---|---|
| 2,005,348 | A | 6/1935 | Michell |
| 2,833,325 | A | 5/1958 | Laisy |
| | | (Continued) | |

FOREIGN PATENT DOCUMENTS

| | | |
|---|---|---|
| DE | 20207850 U1 | 10/2002 |
| WO | WO 95/13755 | 5/1995 |
| WO | WO 2009/055747 | 4/2009 |

OTHER PUBLICATIONS

European Search Report, EP14189707.4, dated Feb. 25, 2015.
"Expedium Spine System" Product Catalog, DePuySpine, a Johnson & Johnson Company, Aug. 2004.

*Primary Examiner* — Andrew Yang
(74) *Attorney, Agent, or Firm* — Polsinelli PC

(57) ABSTRACT

A pivotal bone anchor assembly includes a receiver with an axial bore communicating with a bottom of the receiver through a lower opening, with the bottom of the receiver including an angled planar surface extending upward to define an expanded portion of the lower opening. The receiver further includes upright arms with opposed internal surfaces extending between front and back faces of the upright arms to define an open channel, side outer surfaces opposite the internal surfaces extending downward toward the bottom of the receiver, break-off extensions integrally formed with and extending upwardly from inner edge portions of top surfaces of the upright arms, and non-threaded tool engagement grooves extending horizontally and entirely across the side outer surfaces to the front and back faces of the upright arms, with each tool engagement groove being isolated from the axial bore and located below the top of the respective upright arm.

17 Claims, 36 Drawing Sheets

Related U.S. Application Data continuation of application No. 16/111,461, filed on Aug. 24, 2018, now Pat. No. 10,856,912, which is a continuation of application No. 14/164,952, filed on Jan. 27, 2014, now Pat. No. 10,058,354.

(60) Provisional application No. 61/834,625, filed on Jun. 13, 2013, provisional application No. 61/849,514, filed on Jan. 28, 2013.

(52) U.S. Cl.
CPC ........ *A61B 17/7091* (2013.01); *A61B 17/863* (2013.01); *A61B 17/864* (2013.01); *A61B 2090/037* (2016.02)

(56) References Cited

U.S. PATENT DOCUMENTS

| | | |
|---|---|---|
| 4,600,225 A | 7/1986 | Blose |
| 5,067,955 A | 11/1991 | Cotrel |
| 5,092,635 A | 3/1992 | DeLange et al. |
| 5,234,430 A | 8/1993 | Huebner |
| 5,334,203 A | 8/1994 | Wagner |
| 5,605,458 A | 2/1997 | Bailey et al. |
| 5,607,304 A | 3/1997 | Bailey et al. |
| 5,672,176 A | 9/1997 | Biedermann et al. |
| 5,797,911 A | 8/1998 | Sherman et al. |
| 6,006,930 A | 12/1999 | Dreyer et al. |
| 6,010,502 A | 1/2000 | Bagby |
| 6,063,090 A | 5/2000 | Schlapfer |
| 6,077,262 A | 6/2000 | Schlapfer et al. |
| 6,077,267 A | 6/2000 | Huene |
| 6,254,146 B1 | 7/2001 | Church |
| 6,296,642 B1 | 10/2001 | Morrison et al. |
| 6,412,831 B1 | 7/2002 | Noel et al. |
| 6,554,834 B1 | 4/2003 | Crozet et al. |
| 6,726,689 B2 | 4/2004 | Jackson |
| 6,730,089 B2 | 5/2004 | Jackson |
| 6,736,820 B2 | 5/2004 | Biedermann |
| 6,997,927 B2 | 2/2006 | Jackson |
| 7,087,057 B2 | 8/2006 | Konieczynski et al. |
| 7,186,255 B2 | 3/2007 | Baynham et al. |
| 7,204,838 B2 | 4/2007 | Jackson |
| 7,572,279 B2 | 8/2009 | Jackson |
| 7,717,942 B2 | 5/2010 | Schumacher |
| 7,794,477 B2 | 9/2010 | Melkent et al. |
| 7,972,364 B2 | 7/2011 | Biedermann et al. |
| 8,029,539 B2 | 10/2011 | Kirschman |
| 8,197,517 B1 | 6/2012 | Lab et al. |
| 8,262,662 B2 | 9/2012 | Beardsley et al. |
| 8,382,809 B2 | 2/2013 | Kaufman et al. |
| 8,814,913 B2 | 8/2014 | Jackson |
| 8,911,479 B2 | 12/2014 | Jackson et al. |
| 8,926,670 B2 | 1/2015 | Jackson |
| 9,198,692 B1 | 12/2015 | Doose et al. |
| 9,259,247 B2 | 2/2016 | Chandanson et al. |
| 9,445,847 B2 | 9/2016 | Biedermann et al. |
| 9,724,145 B2 | 8/2017 | Spratt et al. |
| D799,949 S | 10/2017 | Stevenson et al. |
| 9,775,660 B2 | 10/2017 | Spratt et al. |
| 9,782,204 B2 | 10/2017 | Spratt et al. |
| 10,058,354 B2 | 8/2018 | Jackson et al. |
| 10,441,319 B2 | 10/2019 | Jackson et al. |
| 10,973,555 B2 | 4/2021 | Jackson et al. |
| 2002/0143341 A1 | 10/2002 | Biedermann et al. |
| 2003/0023243 A1 | 1/2003 | Biedermann et al. |
| 2003/0100896 A1 | 5/2003 | Biedermann et al. |
| 2003/0100904 A1 | 5/2003 | Biedermann |
| 2003/0149431 A1 | 8/2003 | Varieur et al. |
| 2003/0153911 A1 | 8/2003 | Shluzas |
| 2004/0049196 A1 | 3/2004 | Jackson |
| 2004/0138662 A1 | 7/2004 | Landry et al. |
| 2004/0143265 A1 | 7/2004 | Landry |
| 2004/0147929 A1 | 7/2004 | Biedermann et al. |
| 2004/0167524 A1 | 8/2004 | Jackson |
| 2004/0167525 A1 | 8/2004 | Jackson |
| 2004/0172032 A1 | 9/2004 | Jackson |
| 2004/0186474 A1 | 9/2004 | Matthis et al. |
| 2005/0182410 A1 | 8/2005 | Jackson |
| 2005/0216003 A1 | 9/2005 | Biedermann et al. |
| 2005/0277928 A1 | 12/2005 | Boschert |
| 2006/0009773 A1 | 1/2006 | Jackson |
| 2006/0025771 A1 | 2/2006 | Jackson |
| 2006/0058794 A1 | 3/2006 | Jackson |
| 2006/0083603 A1 | 4/2006 | Jackson |
| 2007/0118123 A1 | 5/2007 | Strausbaugh et al. |
| 2007/0208344 A1 | 9/2007 | Young |
| 2007/0270813 A1 | 11/2007 | Garamszegi |
| 2008/0009864 A1 | 1/2008 | Forton et al. |
| 2008/0269809 A1 | 10/2008 | Garamszegi |
| 2009/0105769 A1 | 4/2009 | Rock et al. |
| 2010/0100136 A1 | 4/2010 | Won et al. |
| 2010/0204735 A1 | 8/2010 | Gephart et al. |
| 2010/0241175 A1 | 9/2010 | Walker et al. |
| 2011/0040338 A1 | 2/2011 | Jackson |
| 2011/0087288 A1 | 4/2011 | Stevenson et al. |
| 2011/0160778 A1 | 6/2011 | Elsbury |
| 2011/0202095 A1 | 8/2011 | Semler et al. |
| 2012/0232598 A1 | 9/2012 | Hestad et al. |
| 2013/0013003 A1 | 1/2013 | Carbone et al. |
| 2013/0218213 A1 | 8/2013 | Lemoine |
| 2014/0081334 A1 | 3/2014 | Jackson |
| 2014/0094849 A1 | 4/2014 | Spratt et al. |
| 2014/0214084 A1 | 7/2014 | Jackson et al. |
| 2014/0277157 A1 | 9/2014 | Chandanson et al. |
| 2021/0106362 A1 | 4/2021 | Jackson et al. |
| 2021/0186570 A1 | 6/2021 | Jackson et al. |

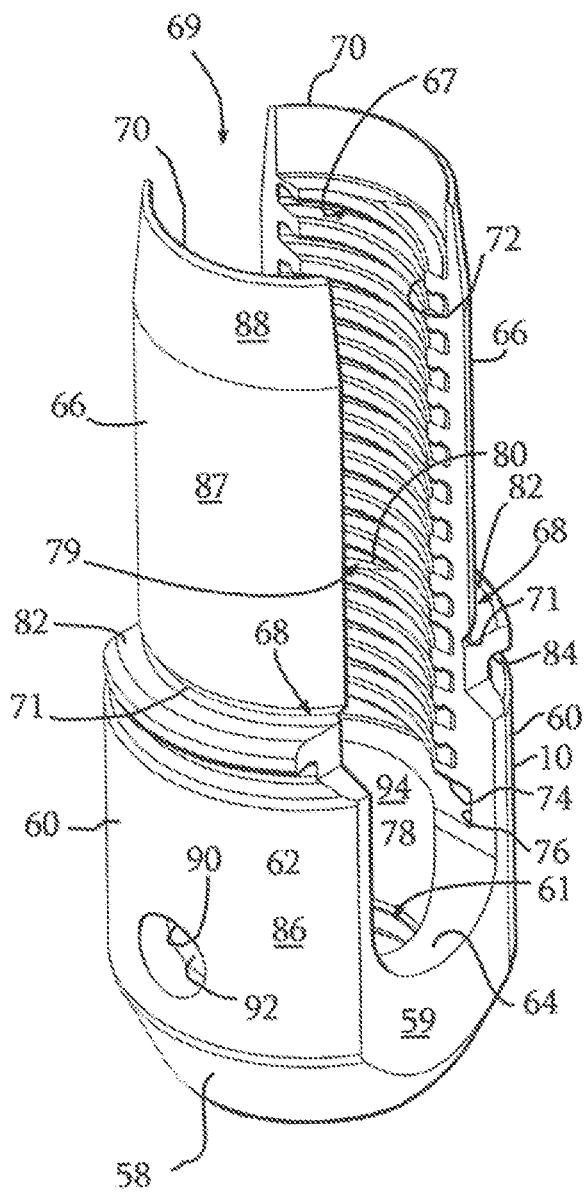
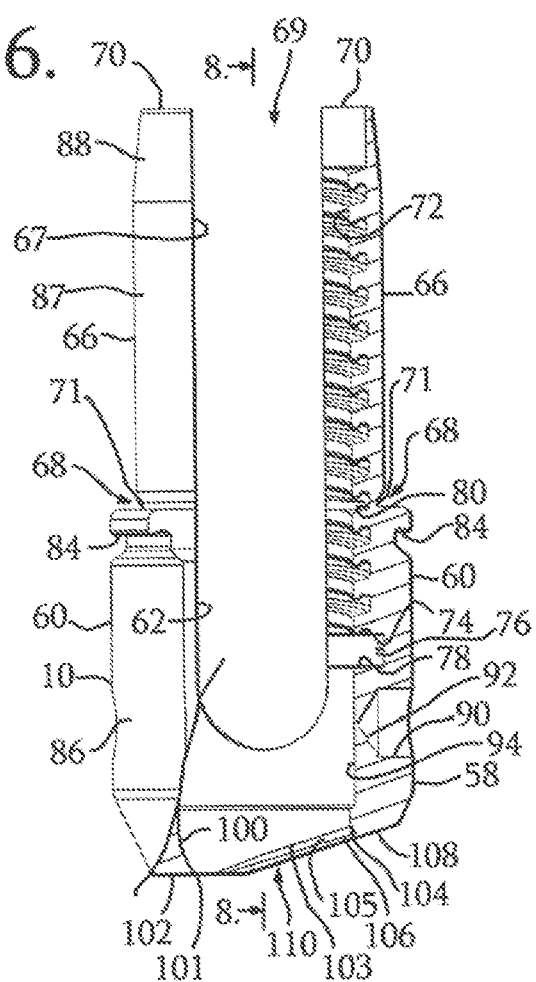
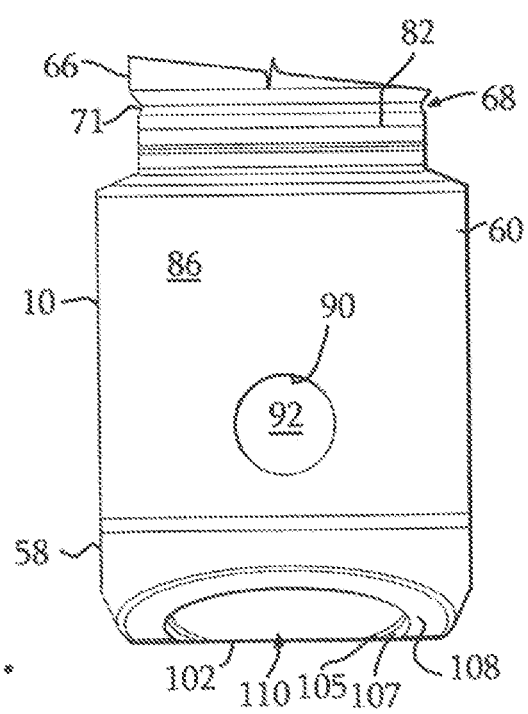

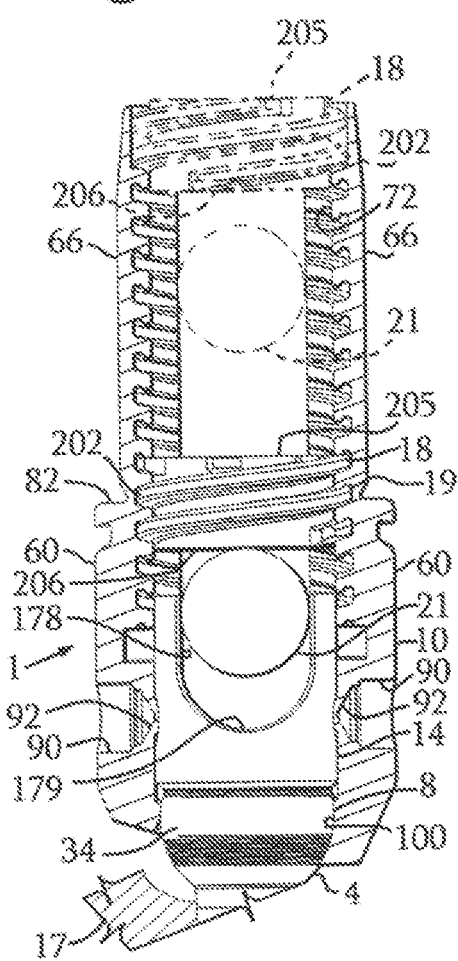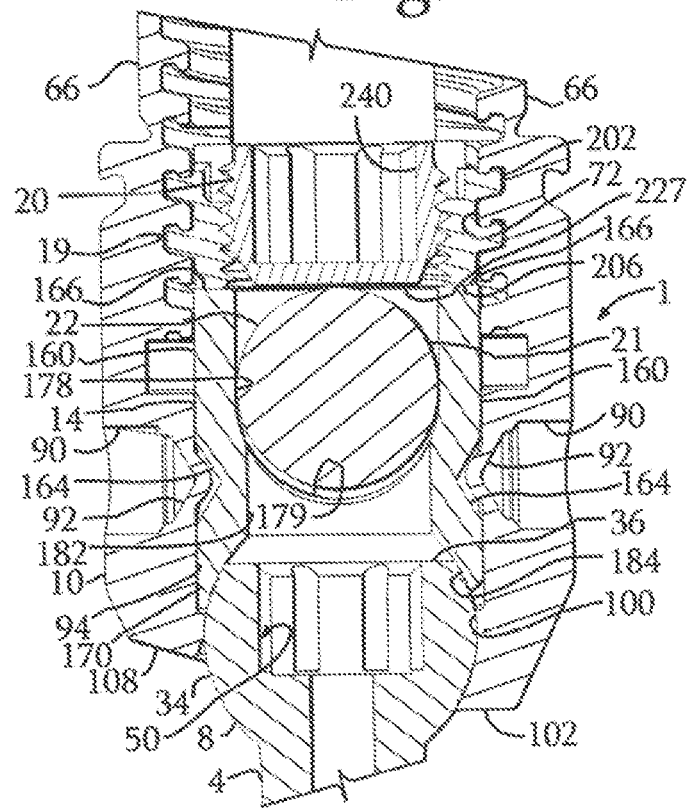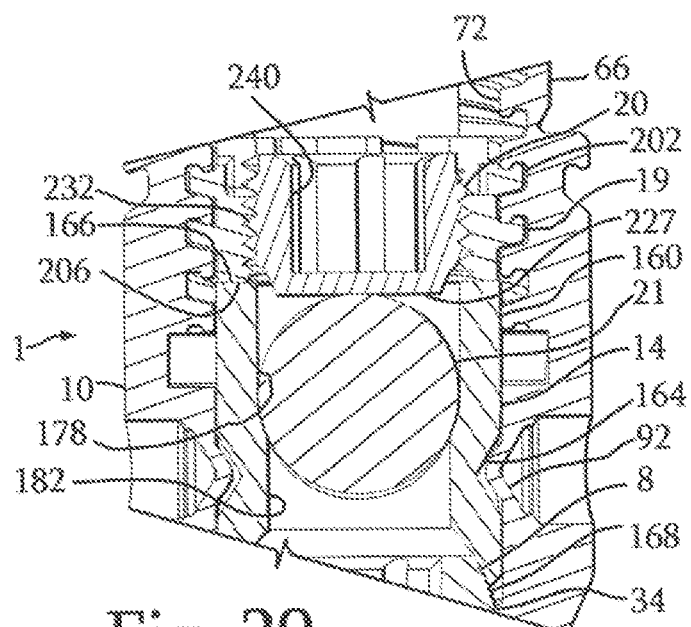

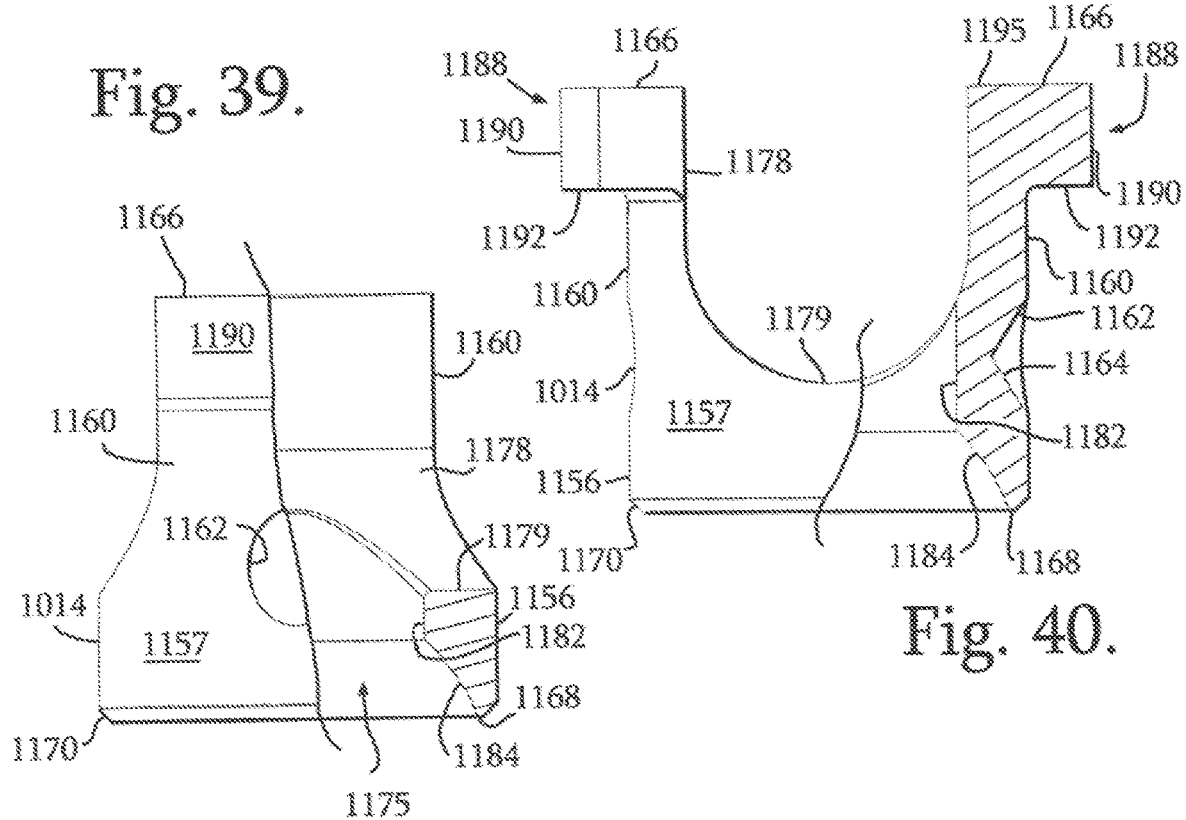
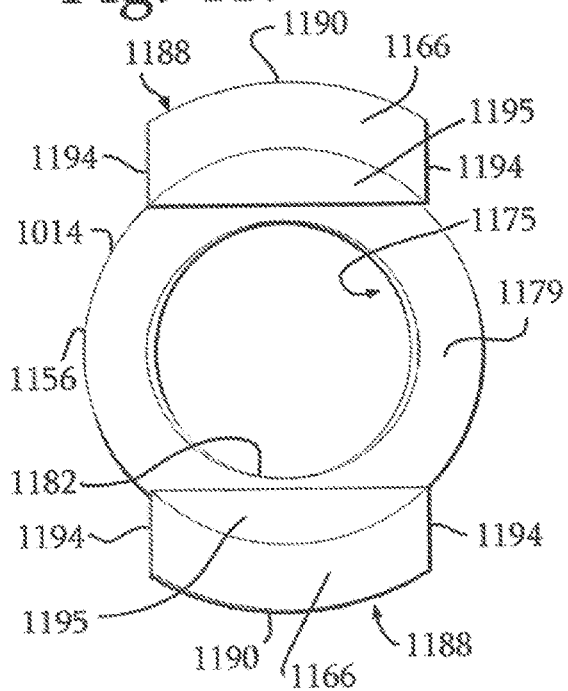

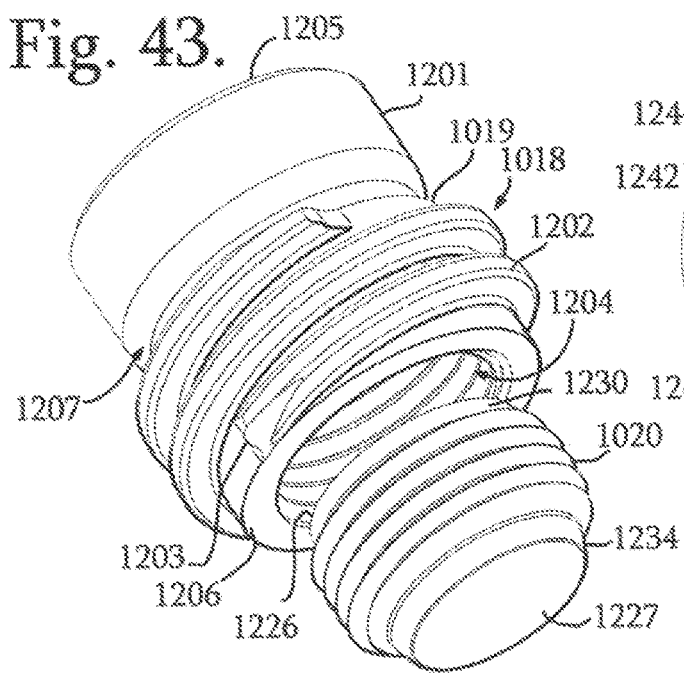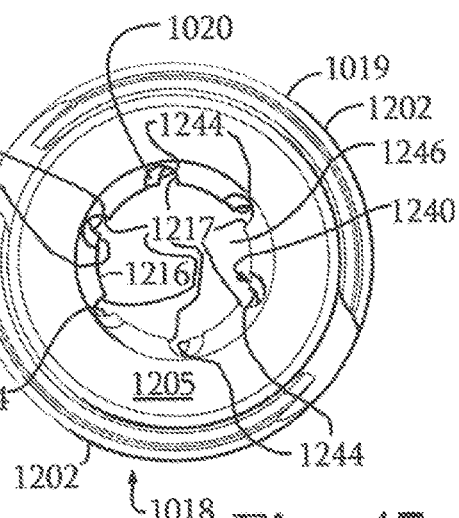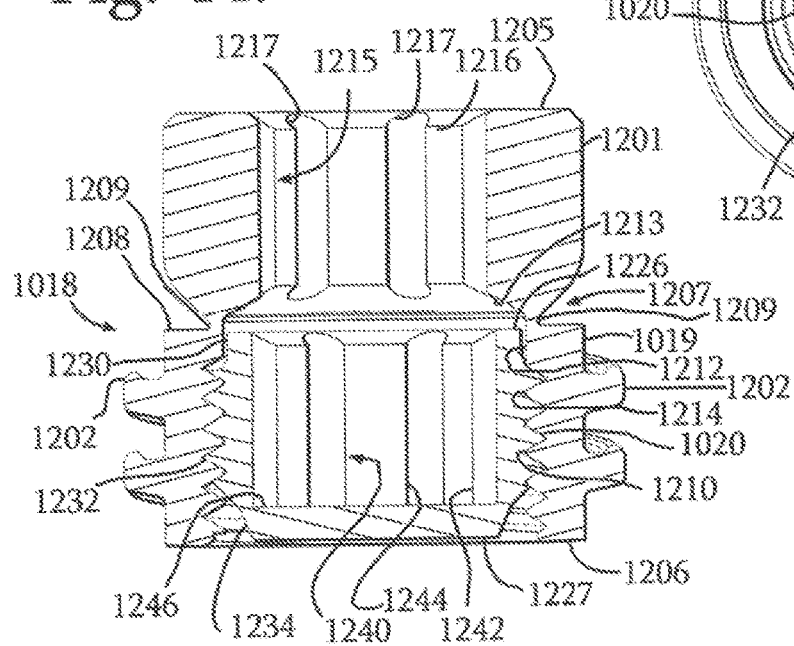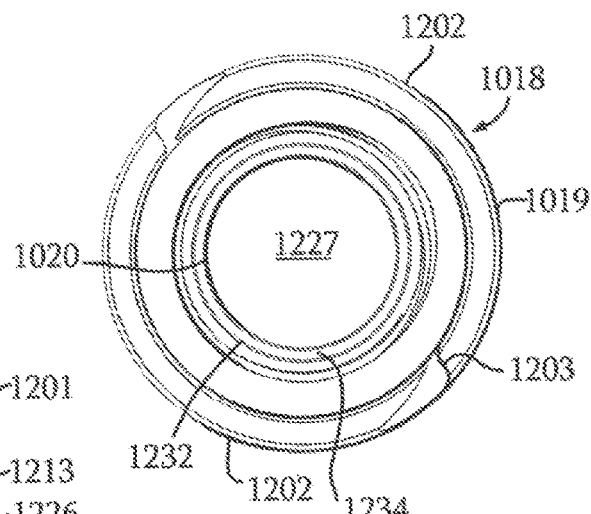
Fig. 43.
Fig. 45.
Fig. 44.
Fig. 46.

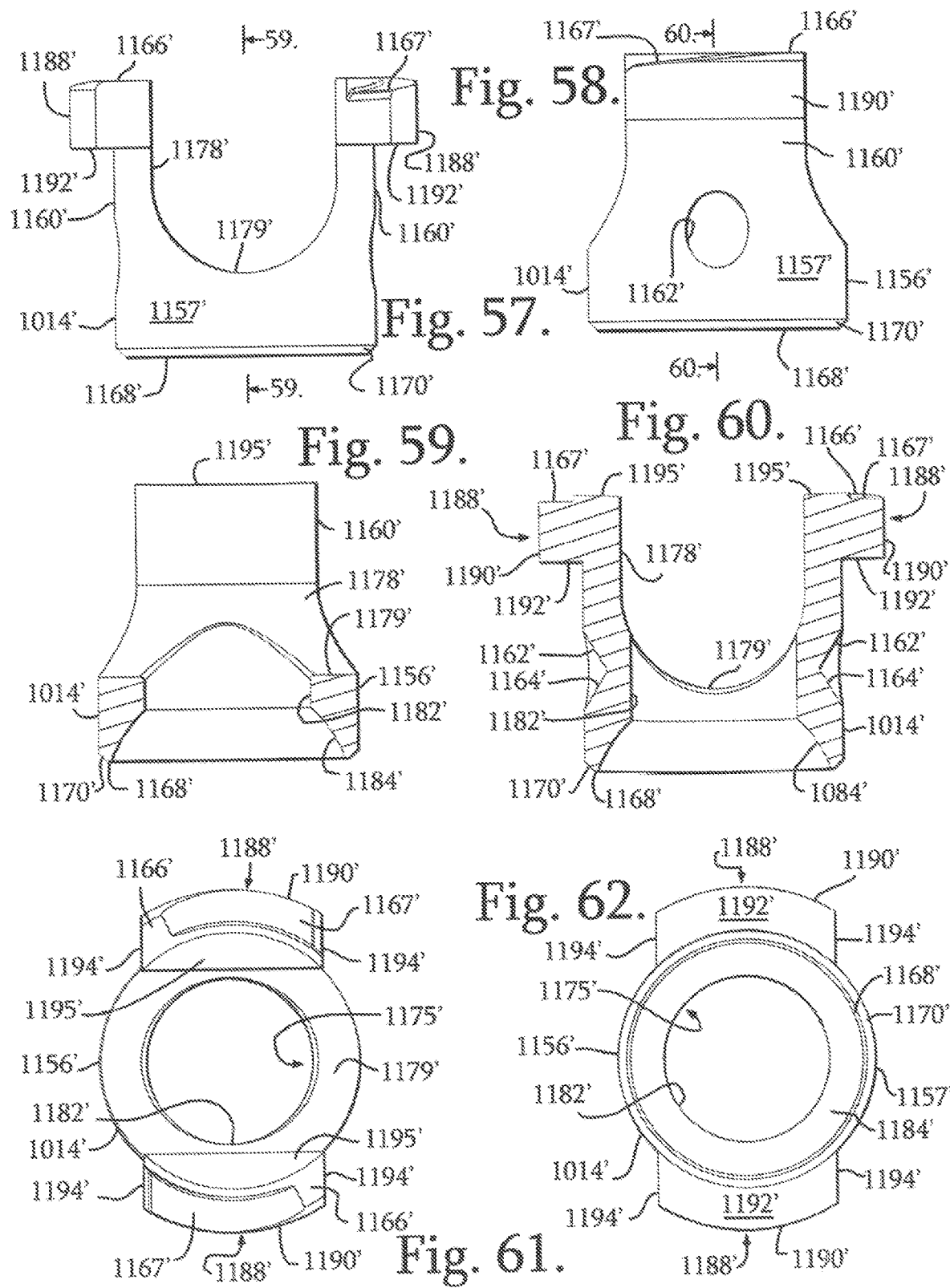

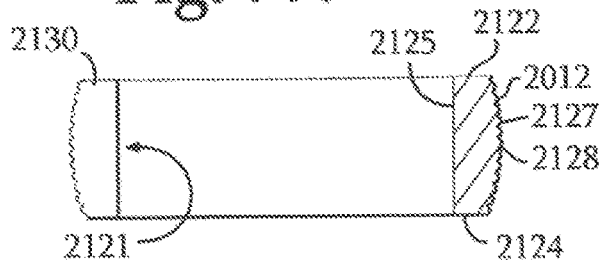
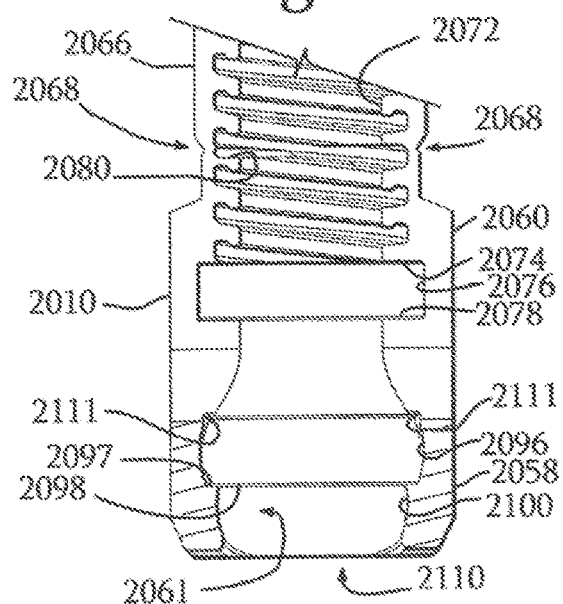
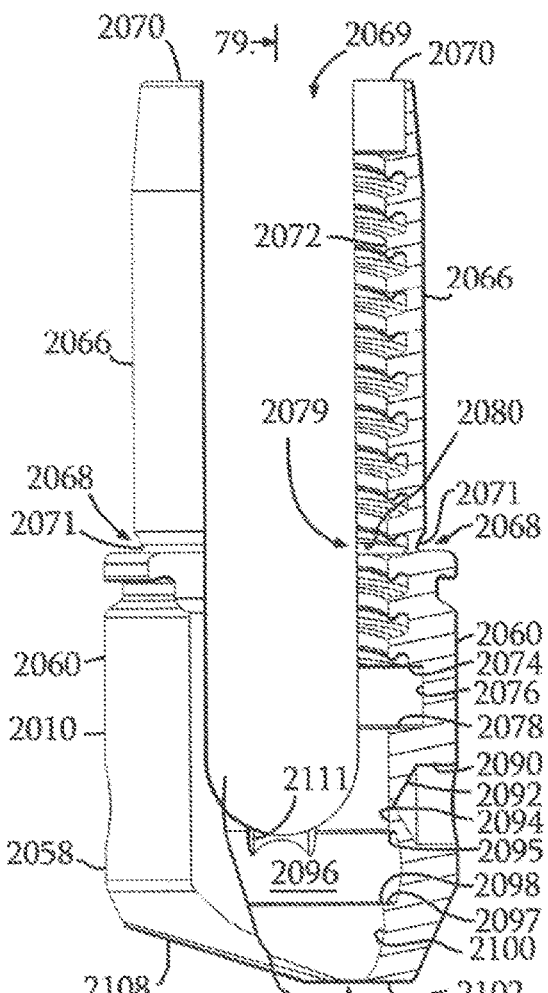
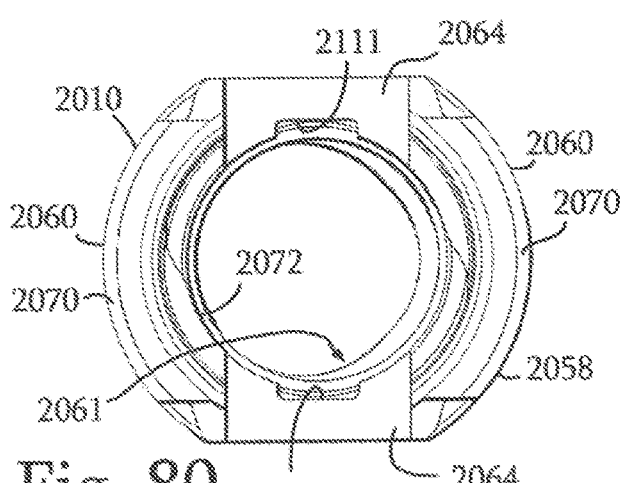
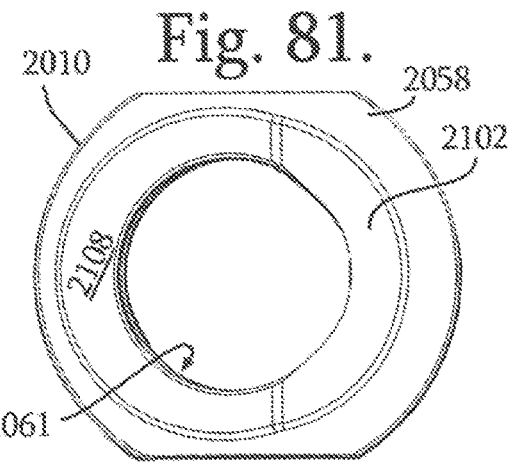

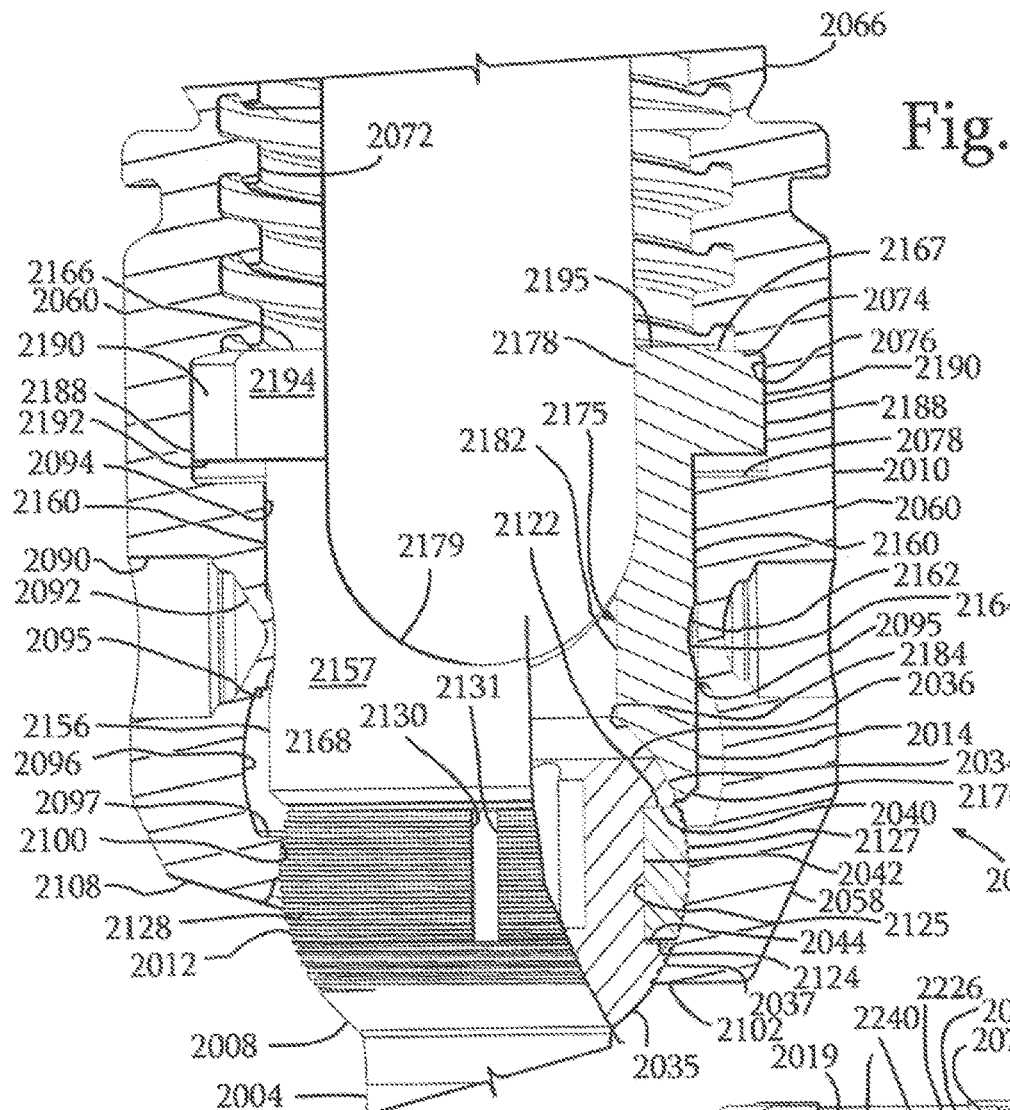
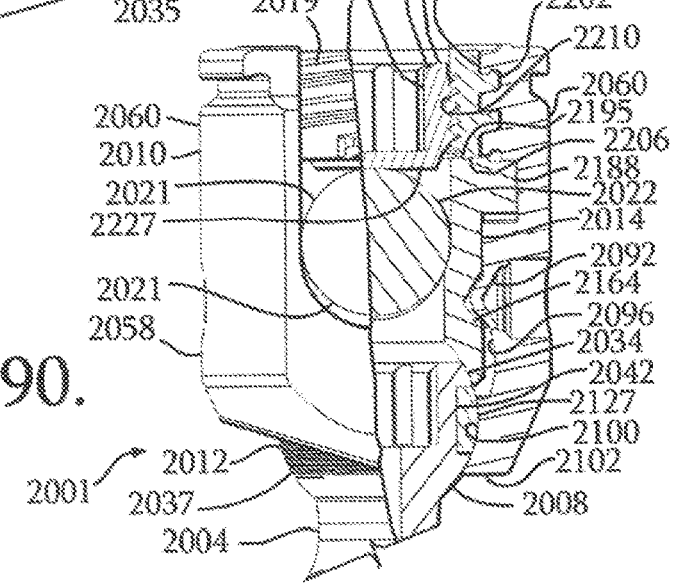

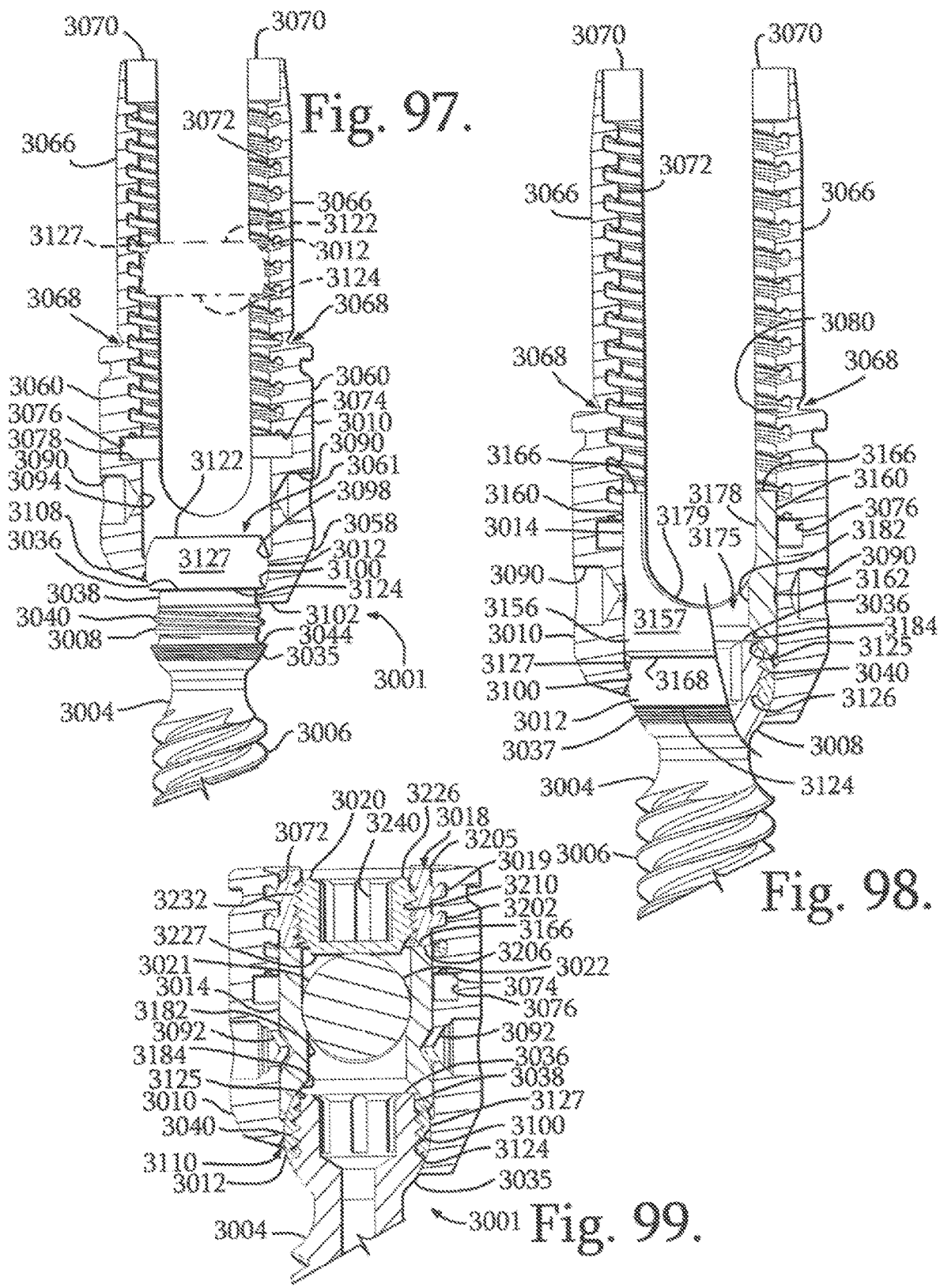

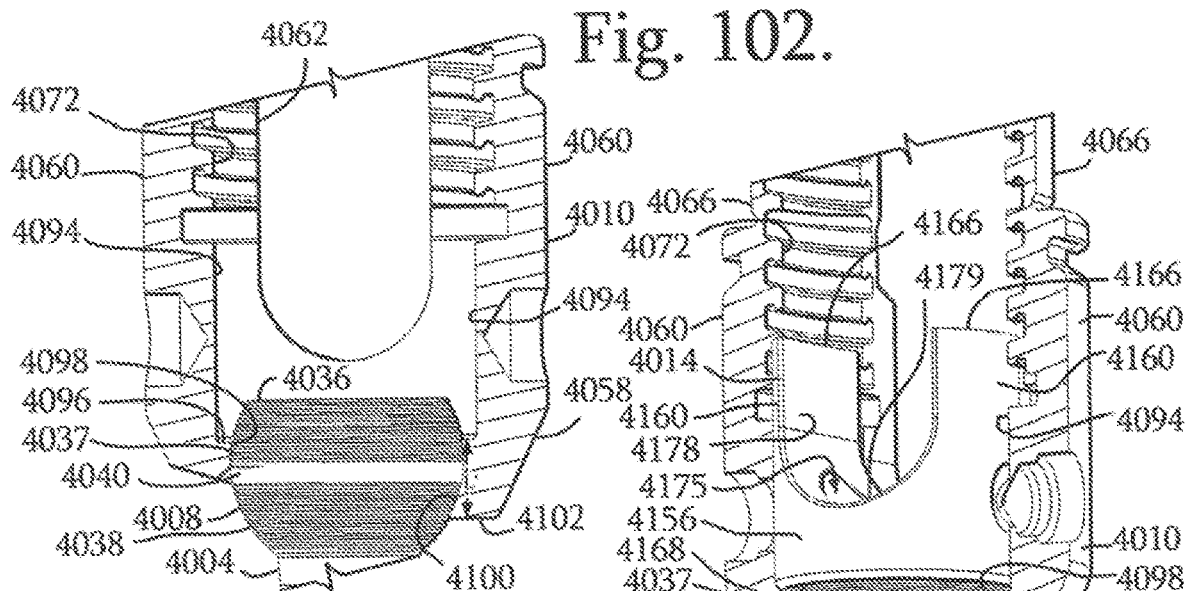
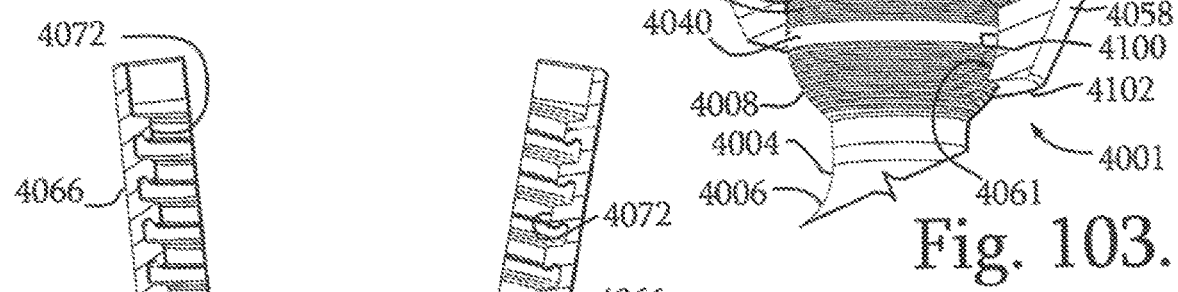
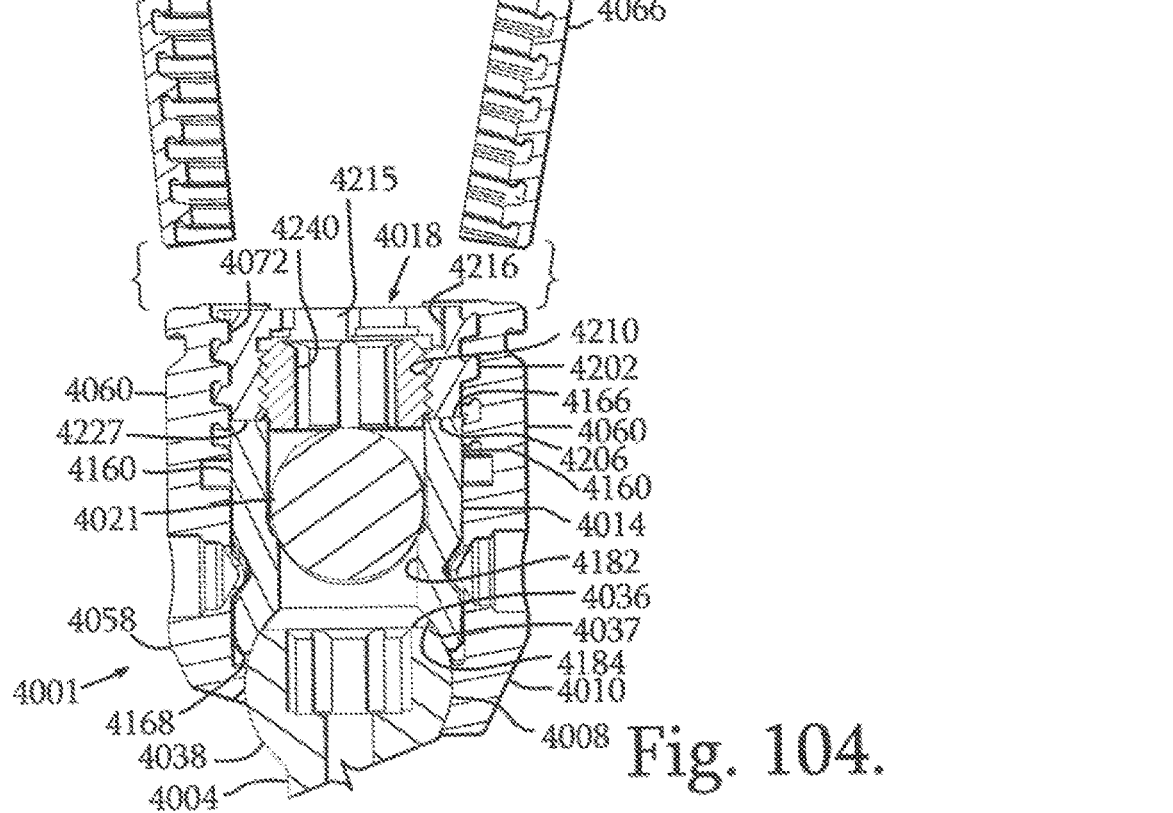

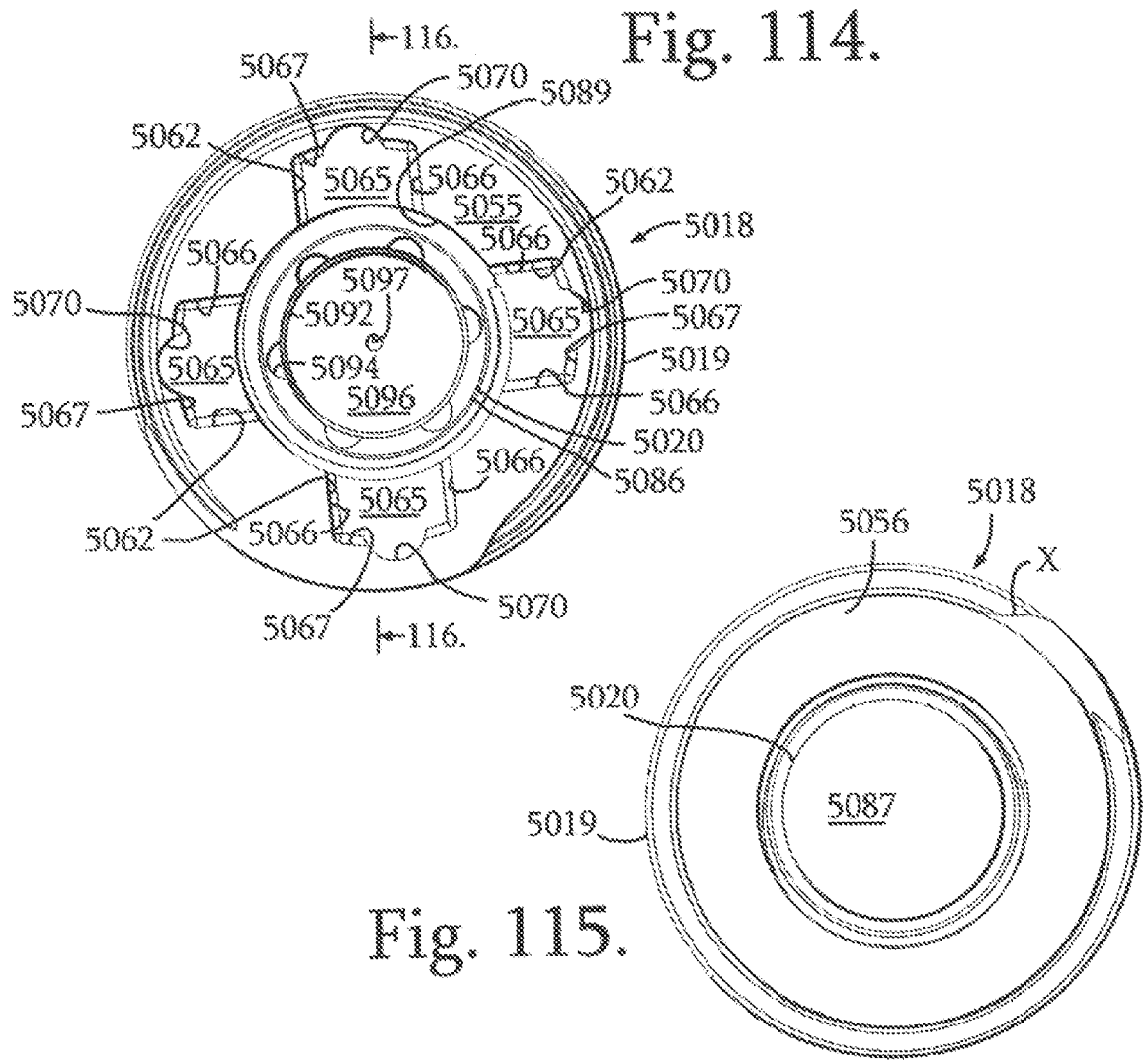
Fig. 114.
Fig. 115.
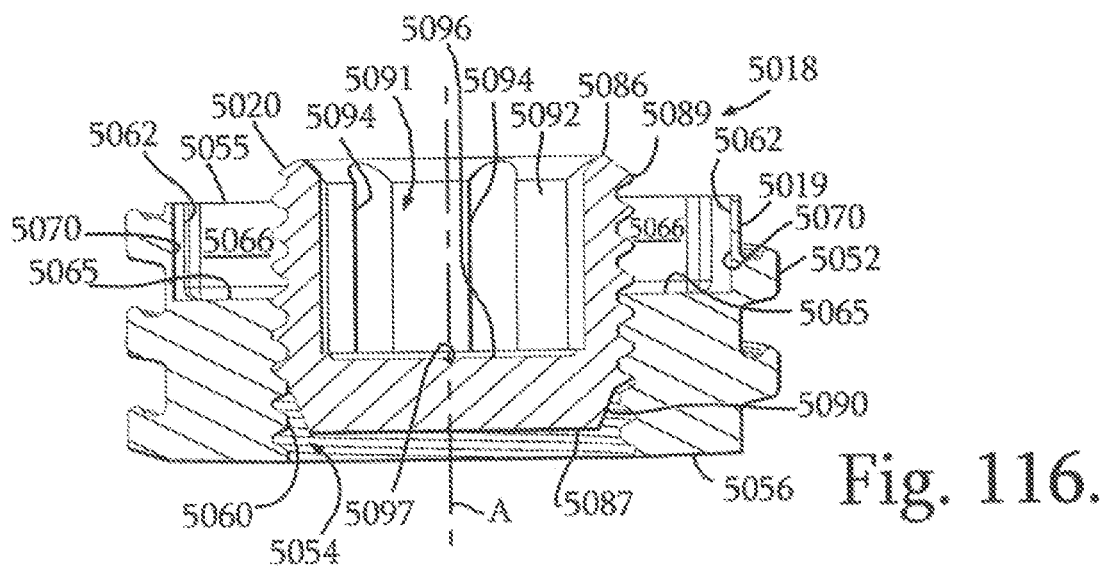
Fig. 116.

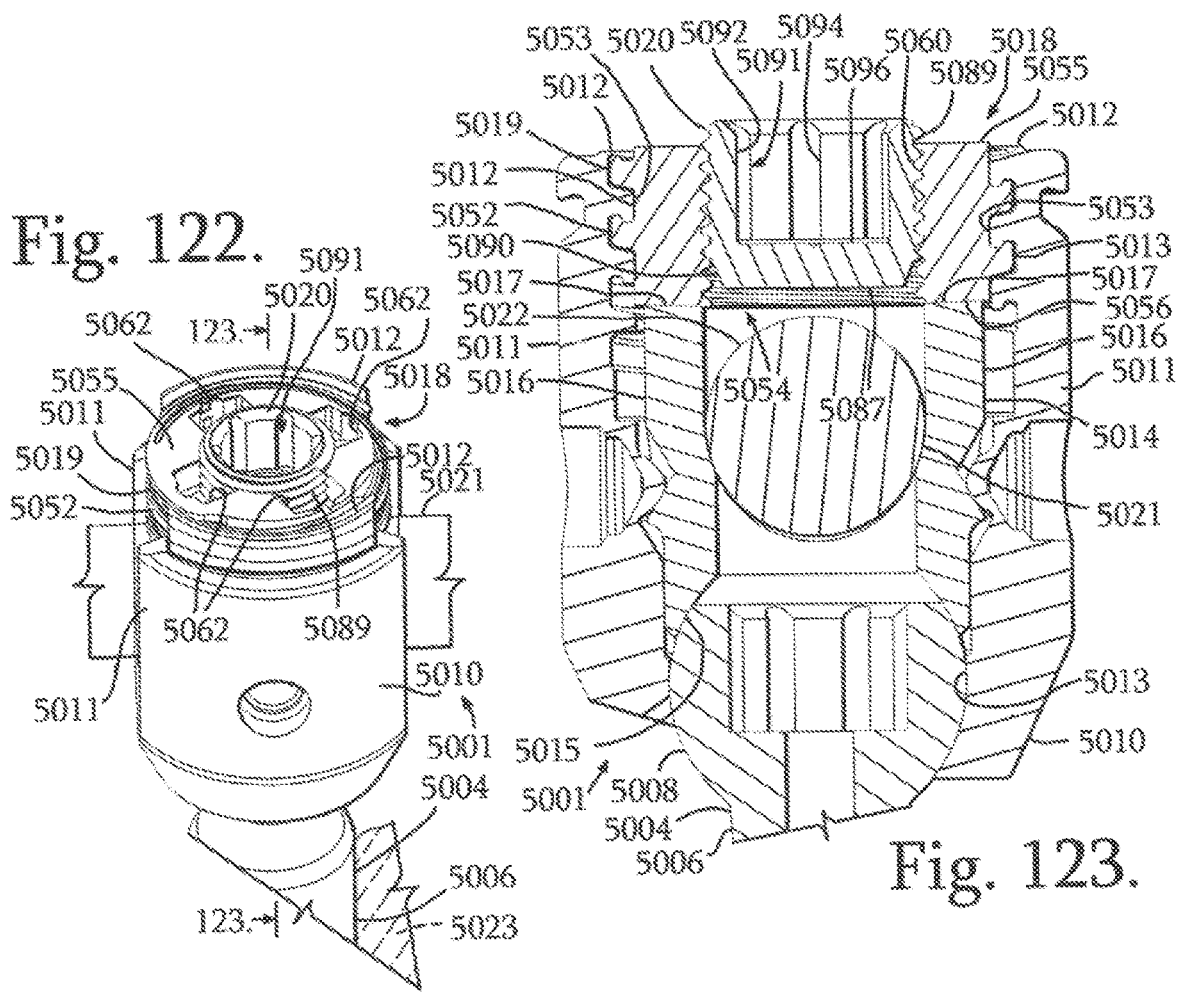
Fig. 122.
Fig. 123.
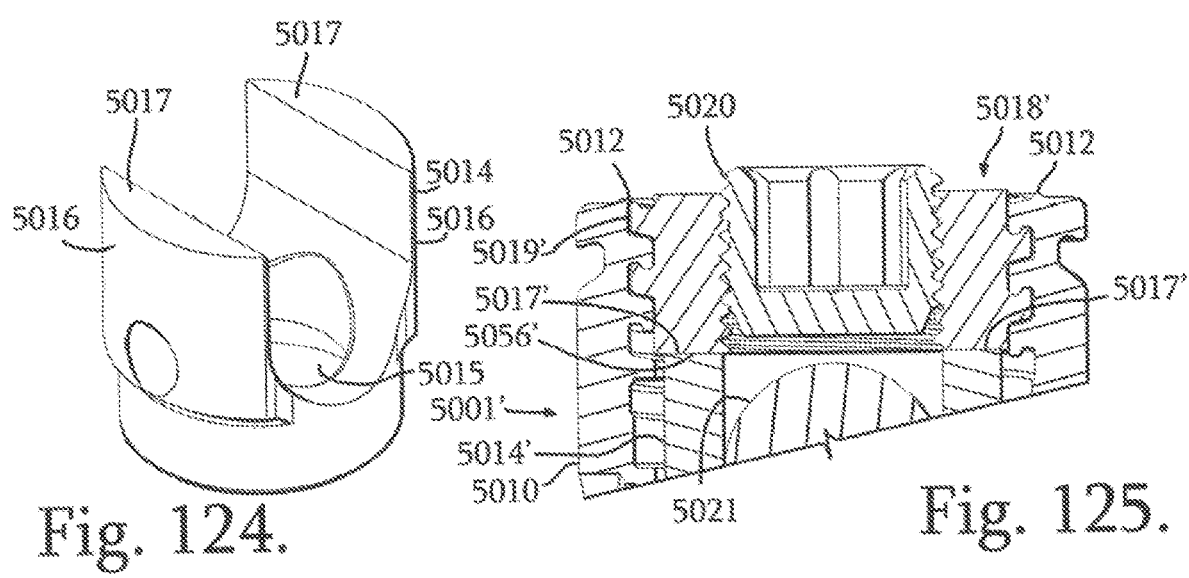
Fig. 124.
Fig. 125.

PIVOTAL BONE ANCHOR ASSEMBLY WITH FAVORED-ANGLE RECEIVER HAVING UPPER TOOL ENGAGEMENT GROOVES AND BREAK-OFF EXTENSIONS

CROSS REFERENCE TO RELATED APPLICATIONS

This application is a continuation of U.S. application Ser. No. 17/113,984, filed Dec. 7, 2020, which is a continuation of U.S. application Ser. No. 16/111,461, filed Aug. 24, 2018, now U.S. Pat. No. 10,856,912, which is a continuation of U.S. application Ser. No. 14/164,952, filed Jan. 27, 2014, now U.S. Pat. No. 10,058,354, which claims the benefit of U.S. Provisional Application No. 61/834,625, filed Jun. 13, 2013, and U.S. Provisional Application No. 61/849,514, filed Jan. 28, 2013, each of which is incorporated by reference in its entirety herein and for all purposes.

BACKGROUND OF THE INVENTION

The present invention is directed to closure structures for joining together parts of a medical implant and to drive systems for such structures, in particular for use with open bone anchors in spinal surgery, and in some embodiments thereof, for use with spinal bone anchors such as polyaxial screws that include compression inserts.

Bone anchors, such as bone screws and hooks are utilized in many types of spinal surgery in order to secure various implants to vertebrae along the spinal column for the purpose of stabilizing and/or adjusting spinal alignment. For example, the most common mechanism for providing vertebral support is to implant bone screws into certain bones which then in turn support a longitudinal connecting member, such as a rod, or are supported by the connector. Although both closed-ended and open-ended bone anchors are known, open-ended anchors are particularly well suited for connections to longitudinal connecting members such as hard, soft or deformable rods, dynamic, soft or elastic connectors and connector sleeves or arms, because such rods or other connector members do not need to be passed through a closed bore, but rather can be laid or urged into an open channel within a receiver or head of such a bone anchor. Generally, the anchors must be inserted into the bone as an integral unit or a preassembled unit, in the form of a shank or hook and connected pivotal receiver. In some instances, a portion of such a preassembled unit, such as a shank of a polyaxial bone screw assembly, may be independently implanted into bone, followed by push- or pop-on assembly of a receiver portion of the unit that includes the open channel for receiving a rod or other longitudinal connecting member.

Typical open-ended bone screws include a threaded shank with a head or receiver having a pair of parallel projecting branches or arms which form a yoke with a U-shaped slot or channel to receive a portion of a rod or other longitudinal connecting member. Hooks and other types of connectors, as are used in spinal fixation techniques, may also include similar open ends for receiving rods or portions of other fixation and stabilization structure. After the rod or other longitudinal connecting member is placed in the receiver channel, a closure, typically in the form of a substantially cylindrical plug is often used to close the channel. Known closures include slide-on types, twist-on varieties that are rotated ninety degrees to a locked in position, and a variety of one- and two-piece cylindrical types having helically wound guide and advancement structures including, for example, thread forms having v-thread, reverse-angle, buttress or square thread forms, to name a few, as well as other non-threadlike helically wound forms, such as Applicant's flange forms described in U.S. Pub. No. 2005/0182410.

SUMMARY OF THE INVENTION

A closure structure embodiment according to the invention includes an outer fastener portion and a cooperating inner set screw portion, the closure structure outer fastener portion cooperating with a bone anchor for capturing a spinal fixation longitudinal connecting member, such as a rod, the anchor having an open receiver with spaced apart arms defining a longitudinal connecting member receiving channel therebetween. The bone anchor further includes a shank or hook portion that pivots with respect to the receiver. The outer fastener is sized and shaped for engagement with spaced apart arms of a compression or pressure insert located within the bone anchor open receiver. The outer fastener presses downwardly against the pressure insert arms and the insert in turn presses against an upper surface of the pivotal shank or hook portion, fixing an angle of the shank or hook with respect to the receiver independently of the fixing of the longitudinal connecting member with respect to the bone anchor receiver. It is the inner set screw that ultimately abuts against the longitudinal connecting member, fixing the connector with respect to the bone anchor.

In a particular embodiment, the outer fastener includes an internal drive feature having pockets or partially closed slots (could also be described as partially open sockets) formed in a top surface thereof. The pockets could also be described as partially open sockets as they are hollows in which a driver extension is placed to rotate the fastener that are open in a radially inwardly direction and closed at a location near an outer cylindrical surface of the fastener. Although a four pocket fastener is illustrated, as few as two pockets and up to six or more pockets may be formed in the outer fastener top surface. The illustrated pockets further include an outer curved or lobular recess that extends all the way to the outer fastener helically wound guide and advancement structure without breaking through driving or crest surfaces thereof. A cooperating driver includes extensions or prongs for closely fitting within the drive pockets and an inner extension that is slidingly received by the closure inner set screw.

A system for designing two-piece plug closures of the invention include designing the outer fastener with pockets that have drive surfaces that extend inwardly rather than outwardly to result in a splay control outer flange form or other helical guide and advancement structure having driving and splay control features that are not broken or otherwise compromised by the outer fastener inner drive feature while providing an outer fastener with adequate driving face or flank surface area. Such a system also includes designing a smaller set screw for cooperation with the outer fastener. The set screw is in turn designed with an outer helical guide and advancement structure, preferably a v-thread, that is fine (i.e., a small pitch), resulting in increased thrust of the inner set screw against a cooperating longitudinal connecting member as well as a lower torque value.

Also according to an embodiment of the invention, a compression insert of a polyaxial bone anchor is made from a hard material, such as a cobalt chrome alloy. Embodiments of the invention aid in splay control during torquing or tightening of the closure with respect to the arms that occurs when the closure abuts against the insert located in the receiver. Although the illustrated outer fasteners are shown with helically wound flange form structures, it is noted that other helical forms, such as buttress, reverse angle and square threads may be utilized on the outer fastener and cooperating bone anchor receiver.

The drawings constitute a part of this specification and include exemplary embodiments of the present invention and illustrate various objects and features thereof.

BRIEF DESCRIPTION OF THE DRAWINGS

FIG. 5 is an enlarged perspective view of the receiver of FIG. 1.

FIG. 6 is a front elevational view of the receiver of FIG. 5 with portions broken away to show the detail thereof.

FIG. 7 is an enlarged and partial side elevational view of the receiver of FIG. 5.

FIG. 27 is a reduced and partial front elevational view of the of assembly as shown in FIG. 26 with portions broken away to show the detail thereof, further showing the rod and closure top of FIG. 1, also in front elevation, in a stage wherein the closure top is being wound downwardly in mating relationship with the receiver extension tabs and reducing the rod into the receiver, an earlier stage of loading of the rod and closure top shown in phantom.

FIG. 28 is an enlarged and partial front elevational view with portions broken away, similar to FIG. 27, showing the outer portion of the closure top pressing the insert downwardly into locking relationship with the shank head.

FIG. 29 is an enlarged and partial front elevational view with portions broken away, similar to FIG. 28 and further showing the closure top inner set screw locking down on the rod.

FIG. 39 is an enlarged side elevational view of the insert of FIG. 38 with portions broken away to show the detail thereof.

FIG. 40 is an enlarged front elevational view of the insert of FIG. 38 with portions broken away to show the detail thereof.

FIG. 41 is a top plan view of the insert of FIG. 40.

FIG. 42 is a bottom plan view of the insert of FIG. 40.

FIG. 43 is an enlarged exploded perspective view of the two piece dual start closure of FIG. 33.

FIG. 44 is an enlarged front elevational view of the closure of FIG. 43 with portions broken away to show the detail thereof.

FIG. 45 is a top plan view of the closure of FIG. 43.

FIG. 46 is a bottom plan view of the closure of FIG. 43.

FIG. 57 is a front elevational view of the insert of FIG. 56.

FIG. 58 is a side elevational view of the insert of FIG. 56.

FIG. 59 is a cross-sectional view taken along the line 59-59 of FIG. 57.

FIG. 60 is a cross-sectional view taken along the line 60-60 of FIG. 58.

FIG. 61 is a top plan view of the insert of FIG. 56.

FIG. 62 is a bottom plan view of the insert of FIG. 56.

FIG. 77 is an enlarged cross-sectional view taken along the line 77-77 of FIG. 75.

FIG. 78 is an enlarged front elevational view of the receiver of FIG. 71 with portions broken away to show the detail thereof.

FIG. 79 is a reduced cross-sectional view taken along the line 79-79 of FIG. 78.

FIG. 80 is an enlarged top plan view of the receiver of FIG. 78.

FIG. 81 is an enlarged bottom plan view of the receiver of FIG. 78.

Figure 71:
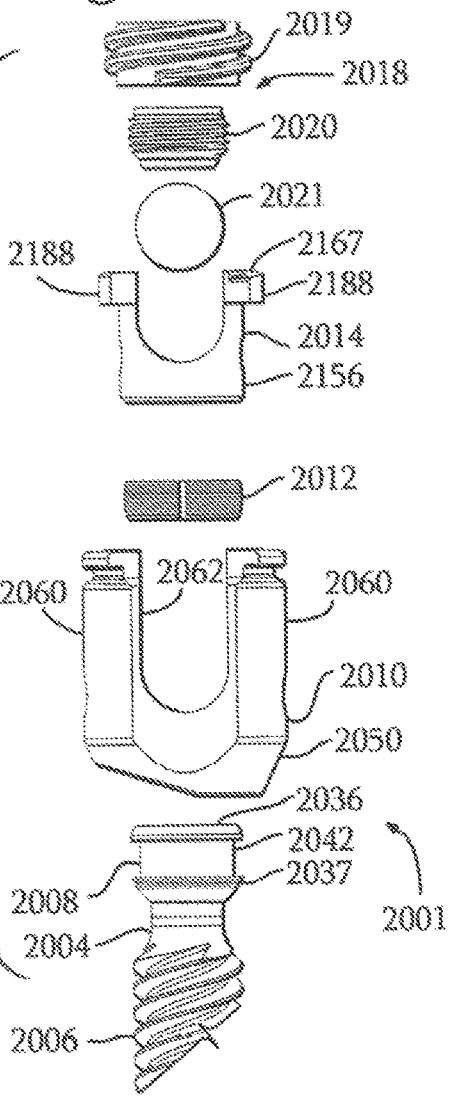
FIG. 71 is an exploded and partial front elevational view of another alternative polyaxial bone screw assembly (shown assembled in FIG. 90), including a shank having an upper portion with a partially cylindrical head, a receiver (shown after break-off tabs removed), a retainer, a cam compression insert and shown with a rod and a two-piece dual start closure top (shown after break-off head removed).
Figure 88:
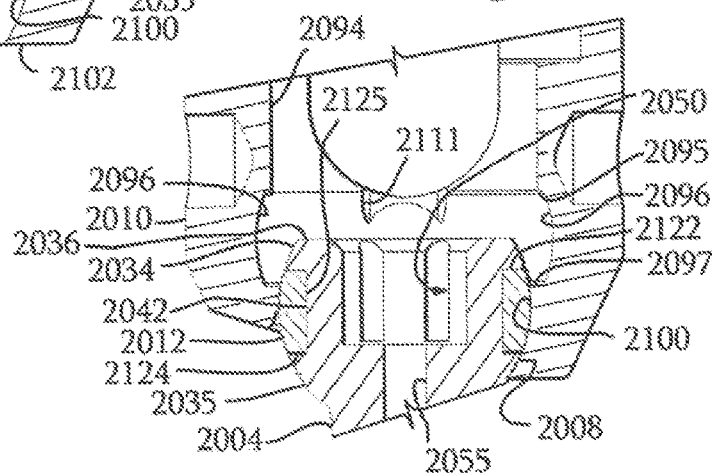
FIG. 88 is a reduced and partial front elevational view with portions broken away of the assembly of FIG. 87 wherein the now assembled retainer and shank are subsequently seated on an inner radiused surface of the receiver.

FIG. 89 is an enlarged and partial front elevational view with portions broken away of the assembly of FIG. 88, further showing the insert of FIG. 71 after being loaded and rotated into an operative position in the receiver and in contact with the shank.

FIG. 90 is a reduced and partial front elevational view of the assembly as shown in FIG. 89 with portions broken away and further shown with a rod and a two piece dual start closure top shown after a break-off head (not shown) has been removed.

Figure 91:
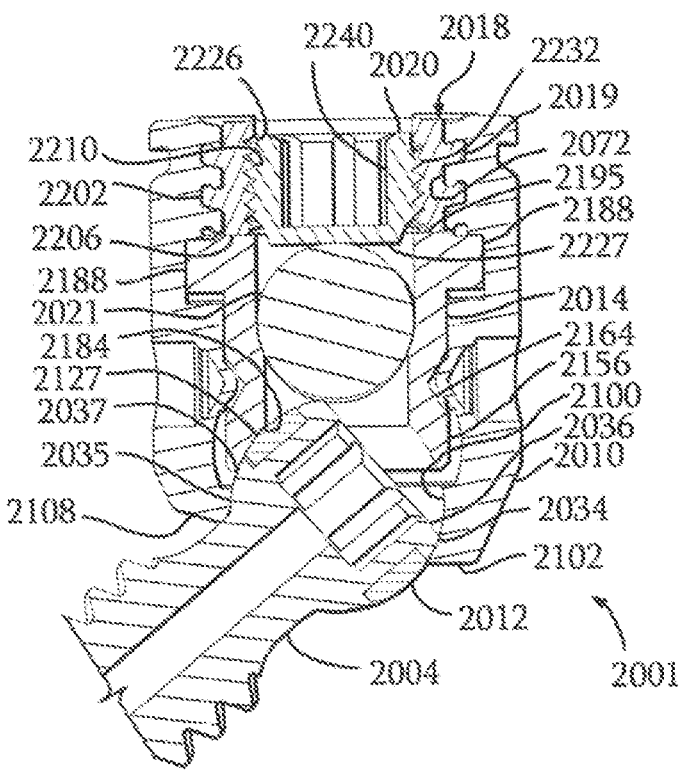

FIG. 91 is a partial front elevational view of the assembly of FIG. 90 with portions broken away, but shown with the shank disposed at a fifty degree (medial) angle with respect to the receiver.

Figure 92:
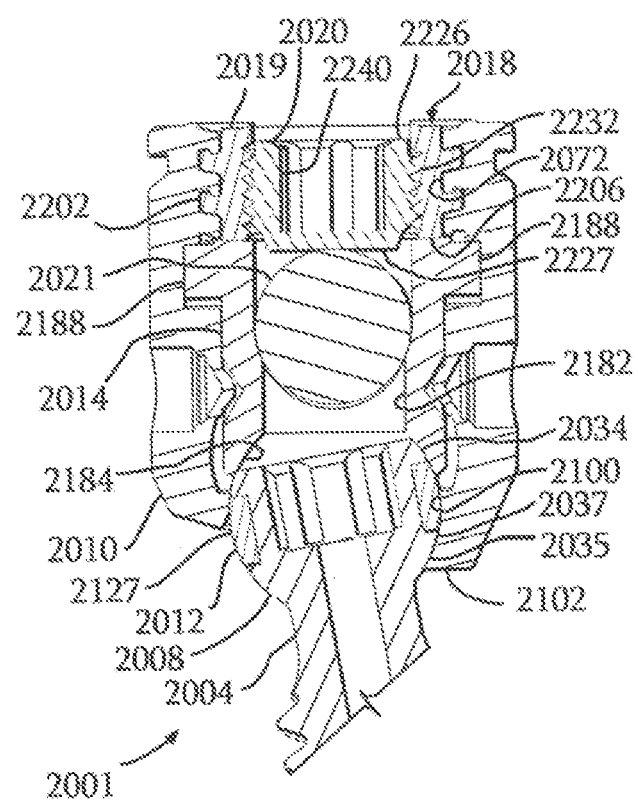

FIG. 92 is a partial front elevational view of the assembly of FIG. 90 with portions broken away, but shown with the shank disposed at a ten degree (lateral) angle with respect to the receiver.

Figure 93:
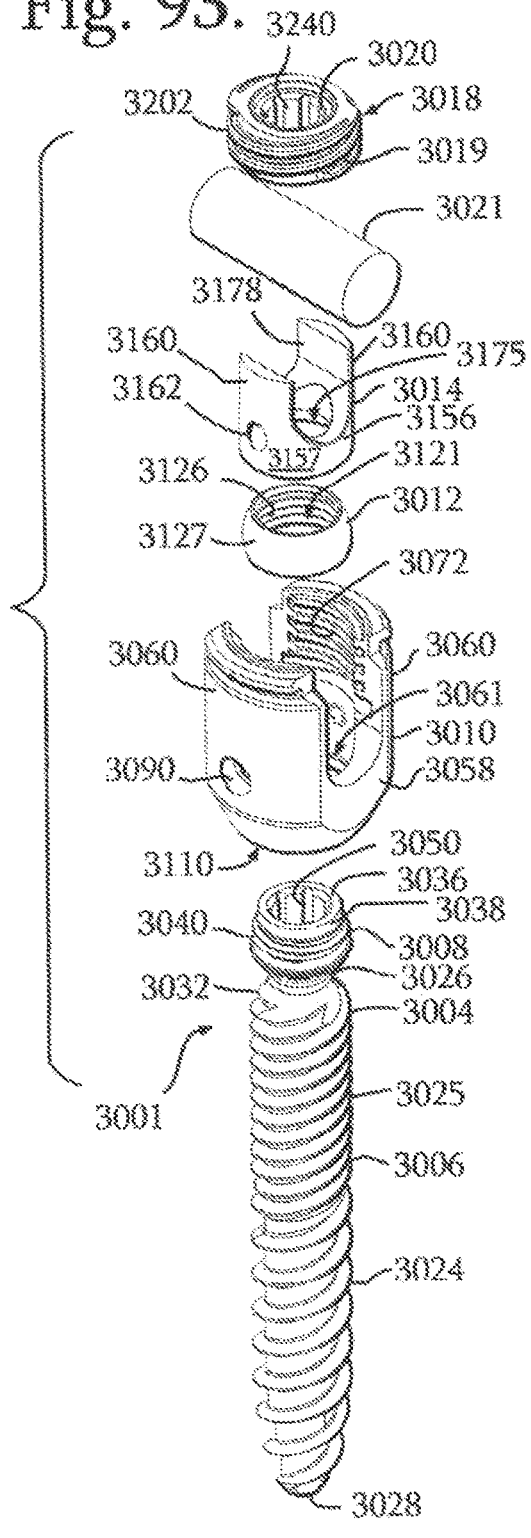

FIG. 93 is an exploded perspective view of another alternative screw including a shank with a threaded head, a receiver, a threaded retainer, an insert and further shown with a rod and a dual start two-piece closure top.

Figure 94:
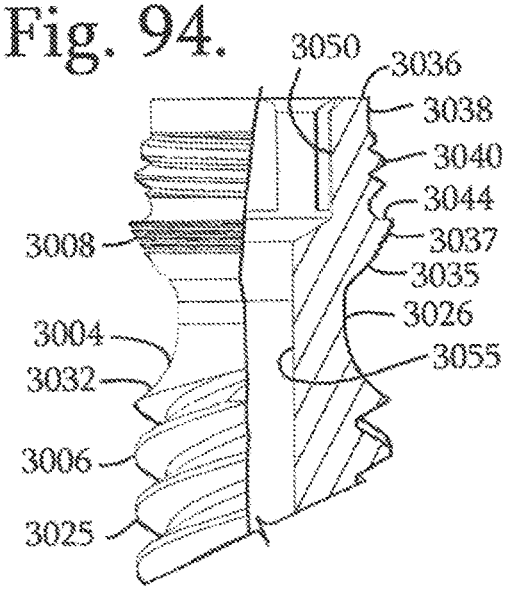

FIG. 94 is an enlarged and partial front elevational view of the shank of FIG. 93 with portions broken away to show the detail thereof.

Figure 95:
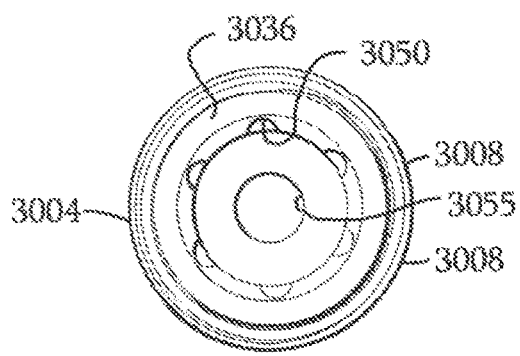

FIG. 95 is an enlarged top plan view of the shank of FIG. 94.

Figure 96:
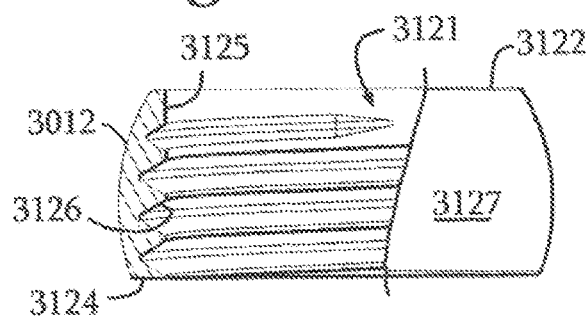

FIG. 96 is an enlarged front elevational view of the retainer of FIG. 93 with portions broken away to show the detail thereof.

FIG. 97 is an enlarged and partial front elevational view with portions broken away of the receiver, retainer and shank of FIG. 93 showing the retainer loaded in the receiver (a top loading stage shown in phantom) and the shank just prior to being loaded in the receiver.

FIG. 98 is an enlarged and partial front elevational view with portions broken away of the assembly of FIG. 97 further showing the shank head threaded into the retainer and also showing the insert of FIG. 93 loaded into the receiver, the insert also in front elevation with portions broken away.

FIG. 99 is an enlarged and partial front elevational view of the assembly of FIG. 98 with portions broken away and further shown with a rod and a two piece dual start closure top.

Figure 100:
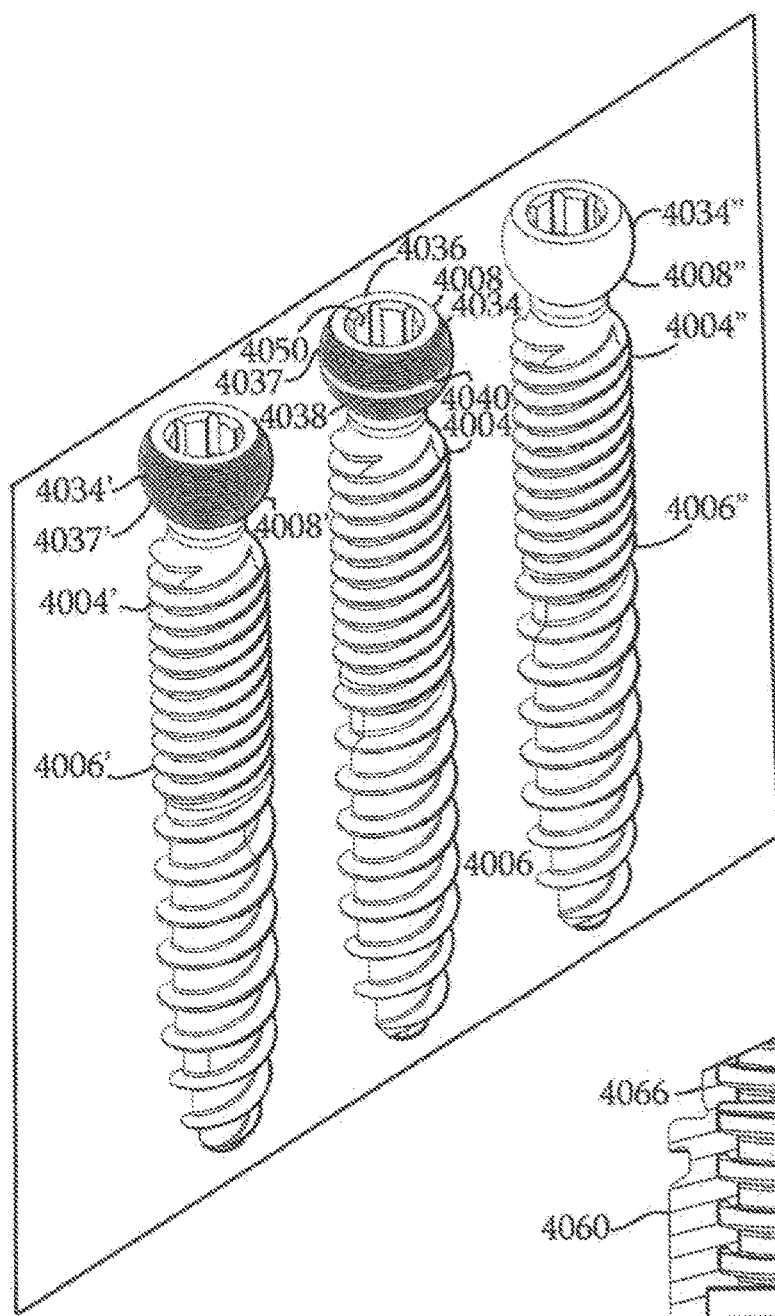

FIG. 100 is a perspective view of a set of first, second and third alternative bone screw shanks for use in bone anchors of the application.

Figure 101:
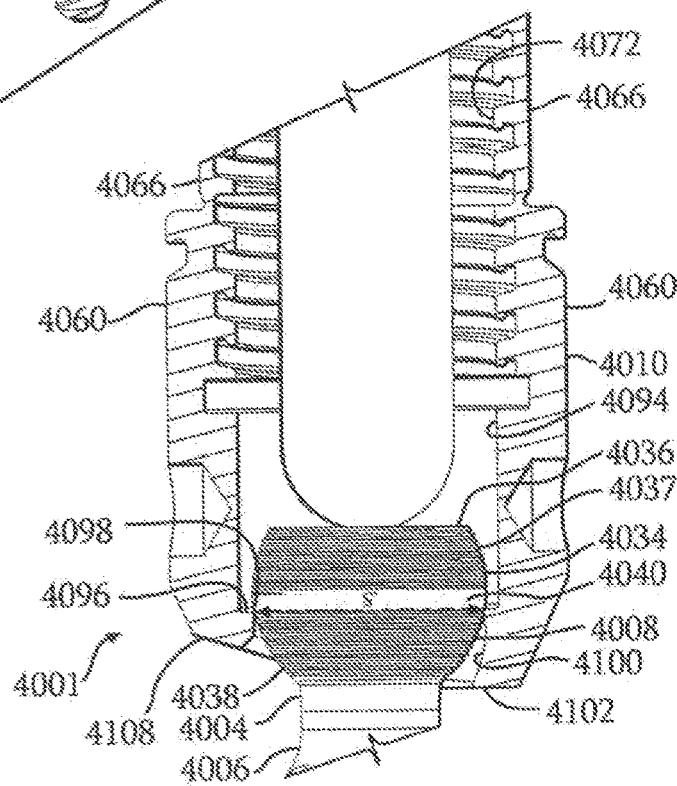

FIG. 101 is an enlarged and partial front elevational view of the second alternative bone screw shank of FIG. 100 shown inserted into another alternative receiver (similar, but not identical to the receiver of FIG. 1), also shown in enlarged and partial front elevation and with portions broken away to show the detail thereof.

FIG. 102 is a partial front elevational view with portions broken away of the shank and receiver of FIG. 102 shown in a subsequent assembly step of seating the shank head on an inner radiused surface of the receiver.

Figure 1:
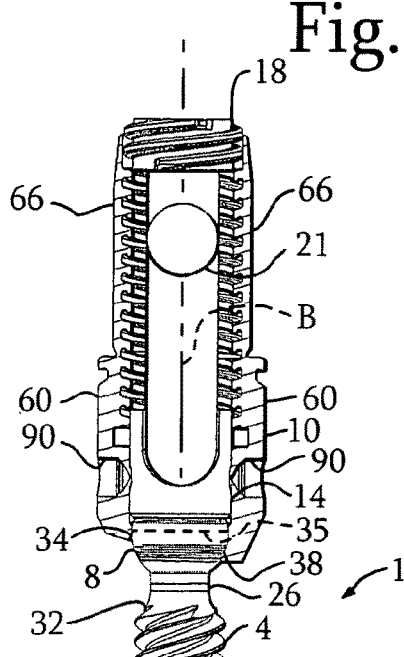
FIG. 1 is a front elevational view of a polyaxial bone screw assembly, shown partially assembled with a longitudinal connecting member in the form of a rod, the assembly including a shank having an integral substantially spherical head, a receiver with break-off extensions or tabs (with portions broken away to show the detail thereof), a compression insert and a two piece dual start closure top having both an outer portion and an inner set screw.
Figure 2:
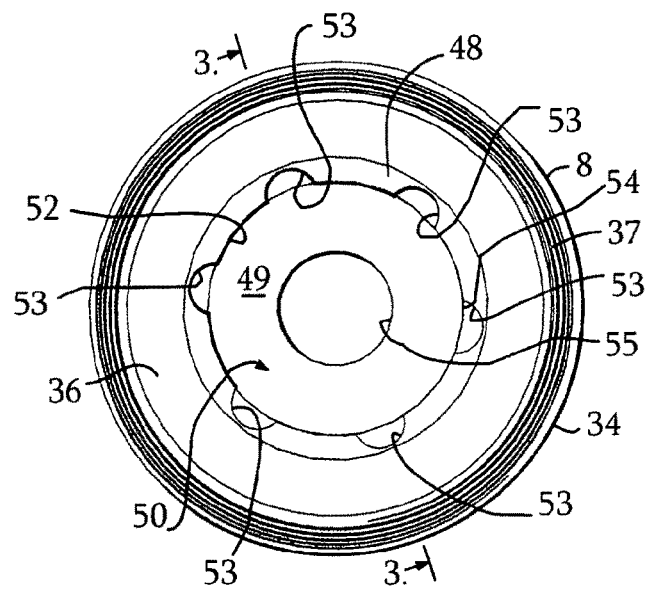
FIG. 2 is an enlarged top plan view of the shank of FIG. 1.
Figure 3:
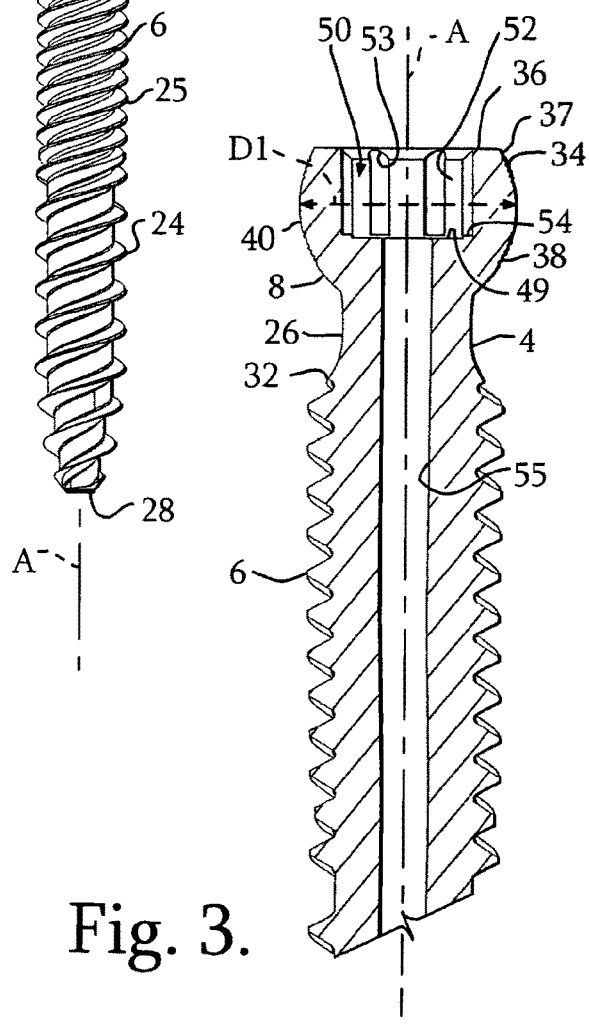
FIG. 3 is a reduced and partial cross-sectional view taken along the line 3-3 of FIG. 2.
Figure 4:
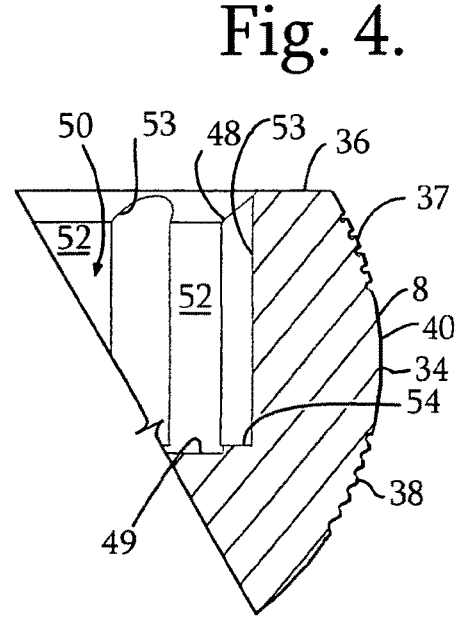
FIG. 4 is an enlarged and partial cross-sectional view taken along the line 3-3 of FIG. 2.

FIG. 103 is a partial perspective view of the shank and receiver of FIG. 102 further shown with an insert substantially similar to the insert shown in FIG. 1.

FIG. 104 is a reduced and partial front elevational view of the shank, receiver and insert of FIG. 103 with portions broken away to show the detail thereof, and shown with a rod and an alternative two-piece single start closure with portions broken away to show the detail thereof, and further shown with the receiver break-off tabs removed.

Figure 105:
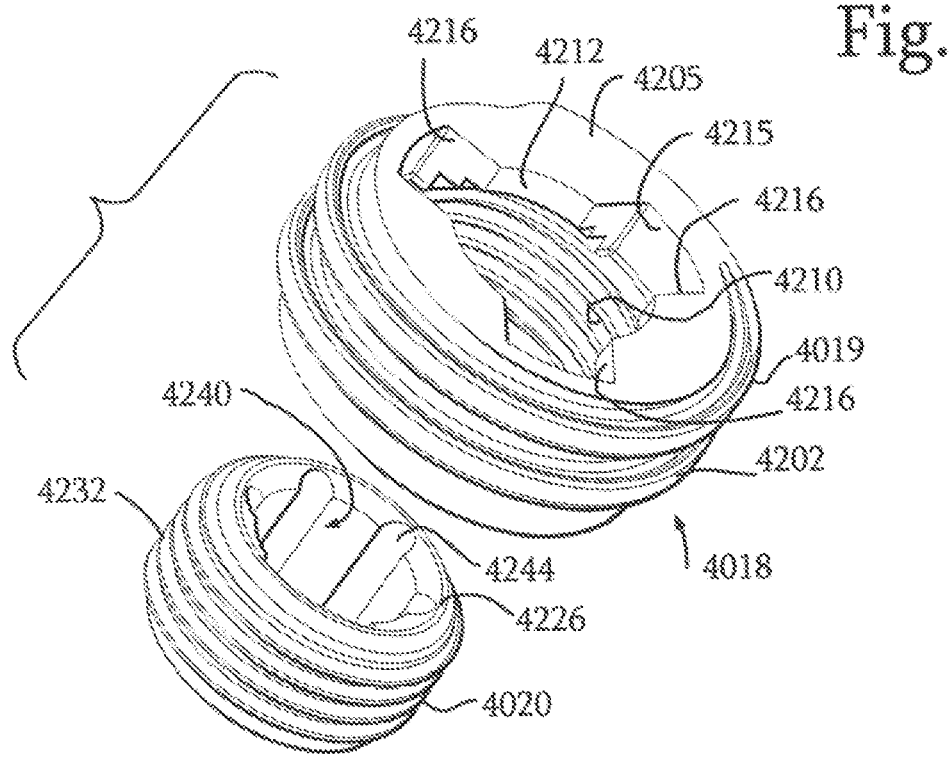

FIG. 105 is an enlarged and exploded perspective view of the two-piece closure of FIG. 104.

Figure 106:
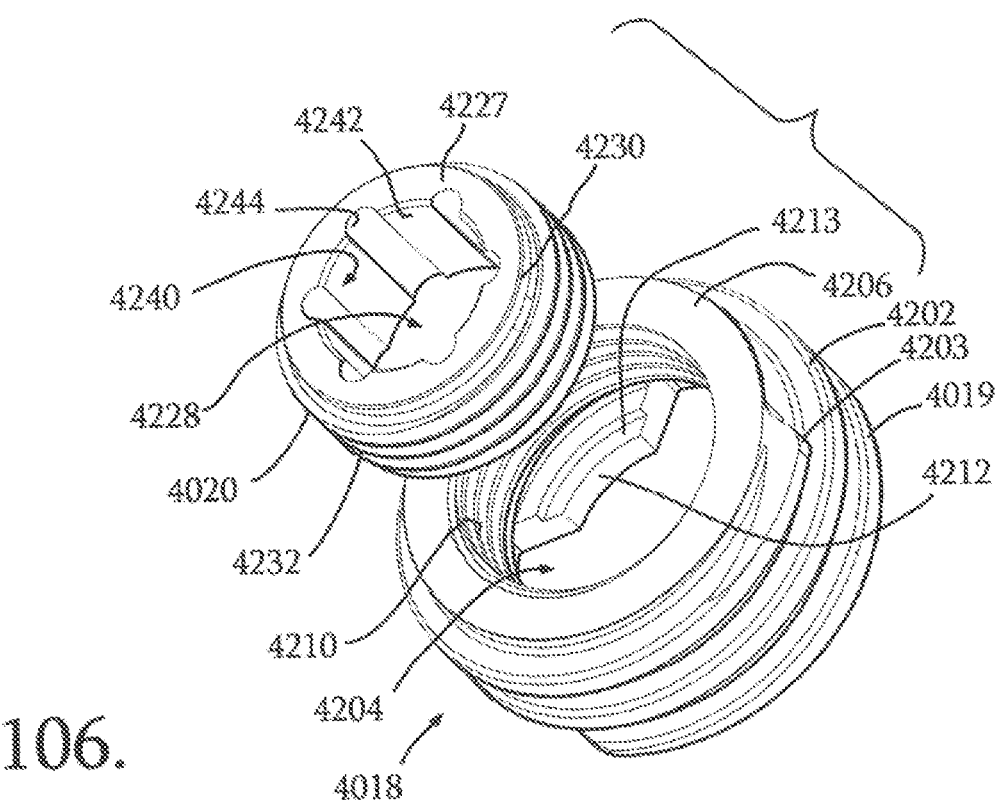

FIG. 106 is another exploded perspective view of the closure of FIG. 105.

Figure 107:
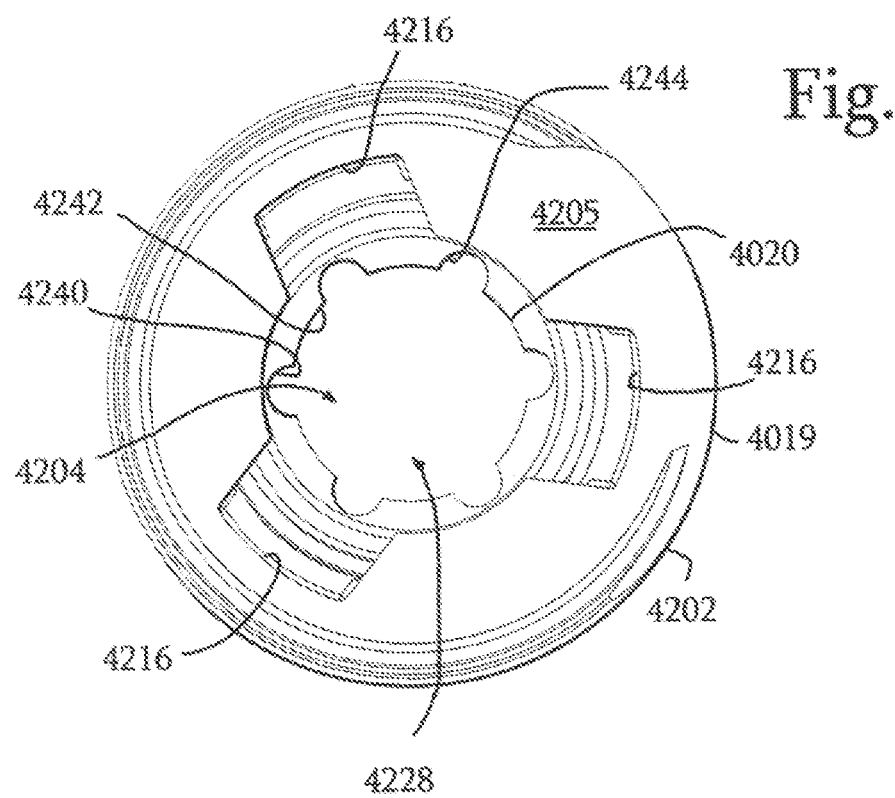

FIG. 107 is an enlarged top plan view of the closure of FIG. 105.

Figure 108:
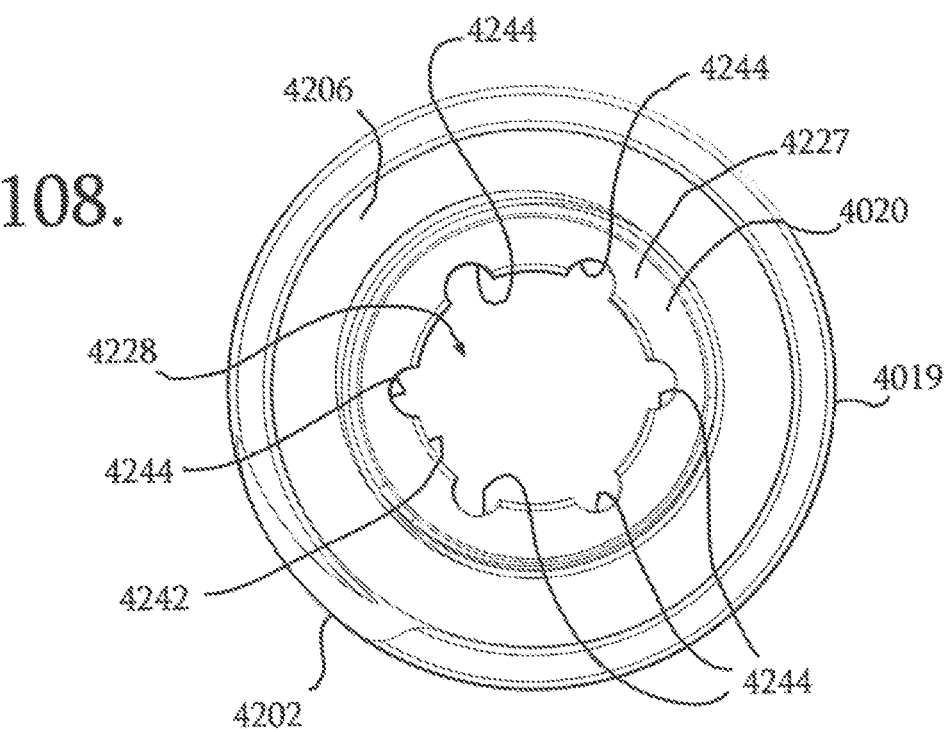

FIG. 108 is an enlarged bottom plan view of the closure of FIG. 105.

Figure 109:
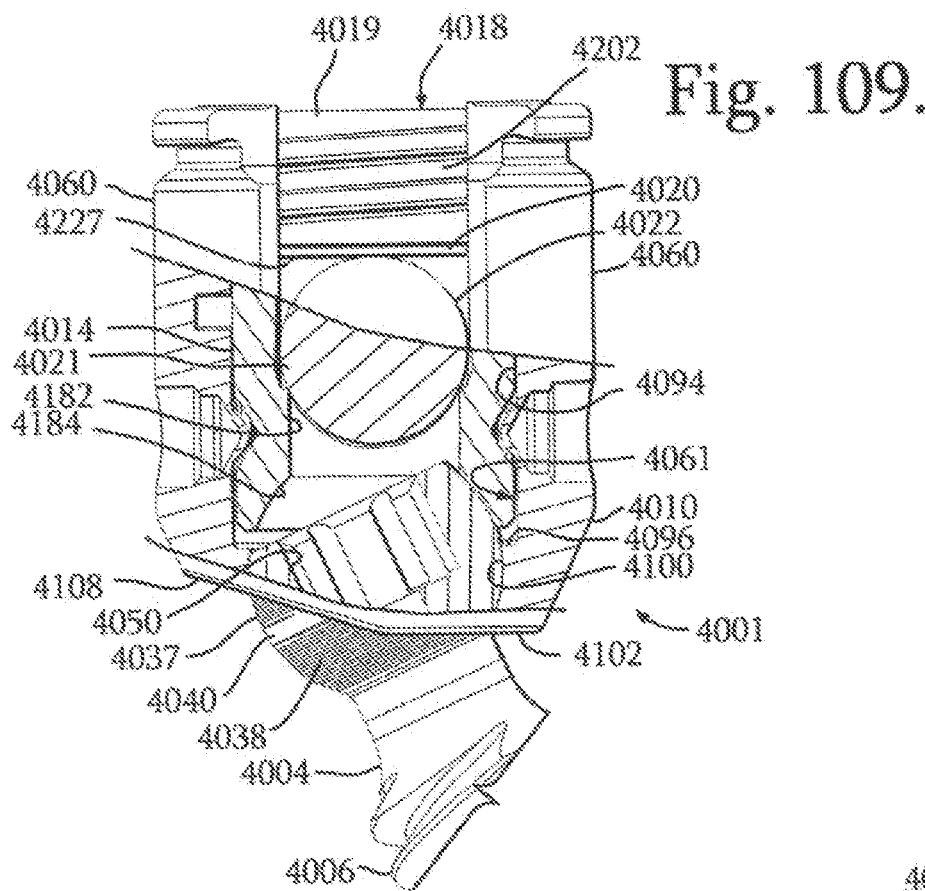

FIG. 109 is an enlarged and partial front elevational view of the assembly of FIG. 104 with portions broken away, but shown with the shank disposed at a minus twenty-five degree angle (medial) with respect to the receiver.

Figure 110:
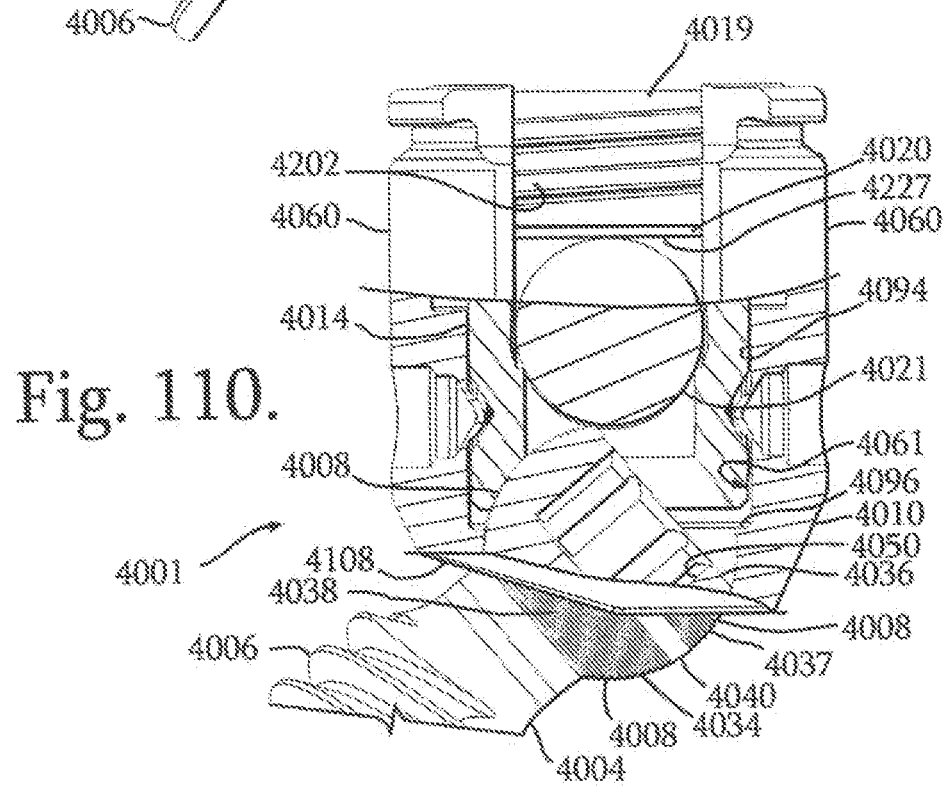

FIG. 110 is an enlarged and partial front elevational view of the assembly of FIG. 104 with portions broken away, but shown with the shank disposed at a plus fifty degree angle (medial) with respect to the receiver.

Figure 111:
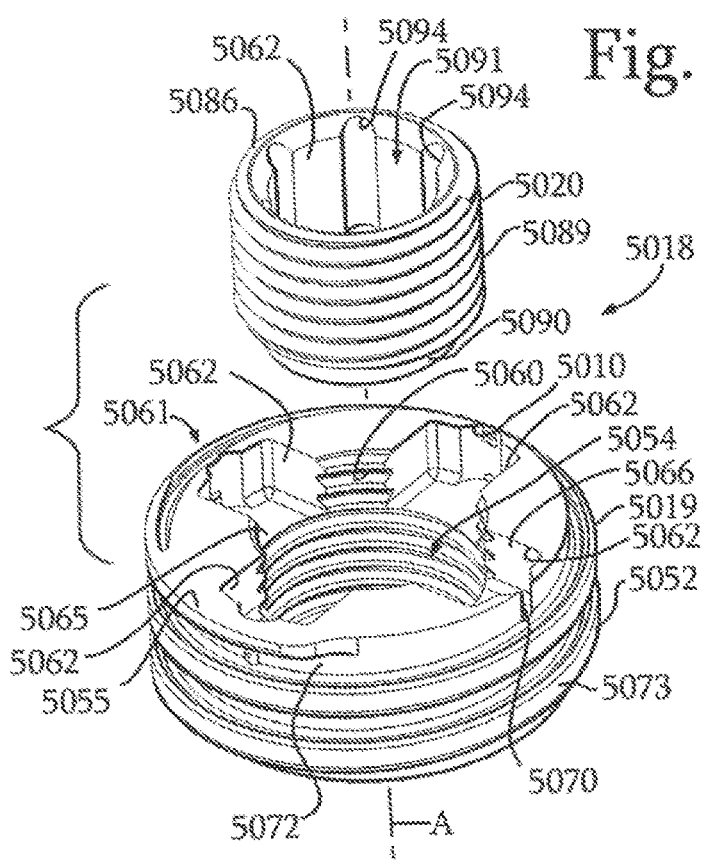

FIG. 111 is an exploded perspective view of a two-piece closure according to another embodiment of the invention.

Figure 112:
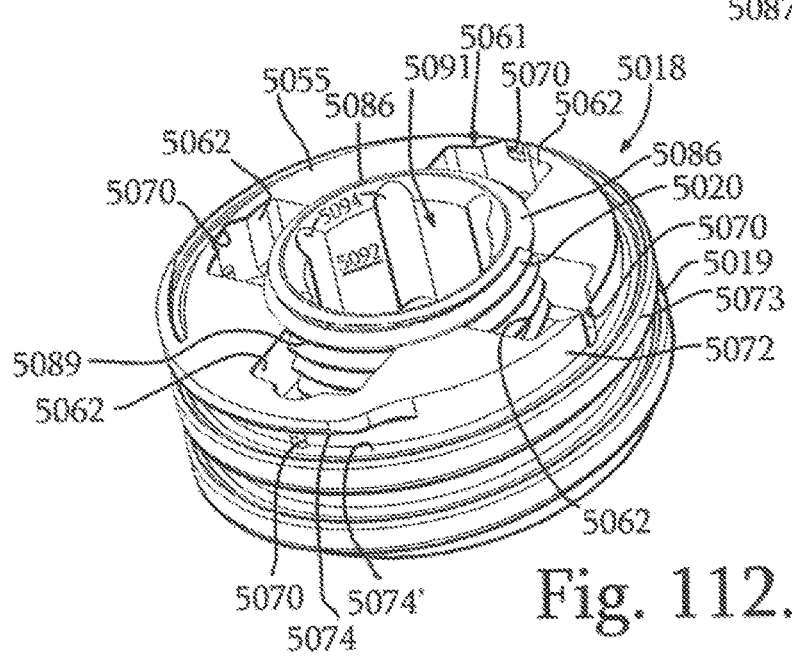

FIG. 112 is an enlarged perspective view of the closure of FIG. 111.

Figure 113:
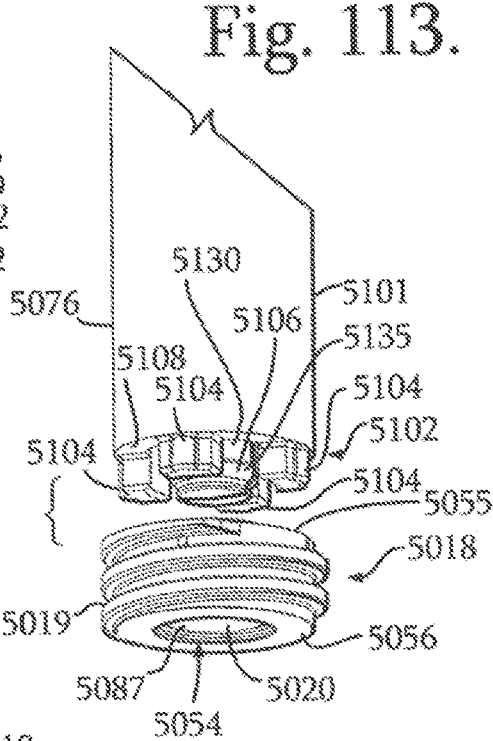

FIG. 113 is a reduced perspective view of the closure of FIG. 111 and shown with a driver according to an embodiment of the invention shown in partial perspective view.

FIG. 114 is an enlarged top plan view of the closure of FIG. 111.

FIG. 115 is an enlarged bottom plan view of the closure of FIG. 111.

FIG. 116 is an enlarged cross-sectional view taken along the line 116-116 of FIG. 114.

Figure 117:
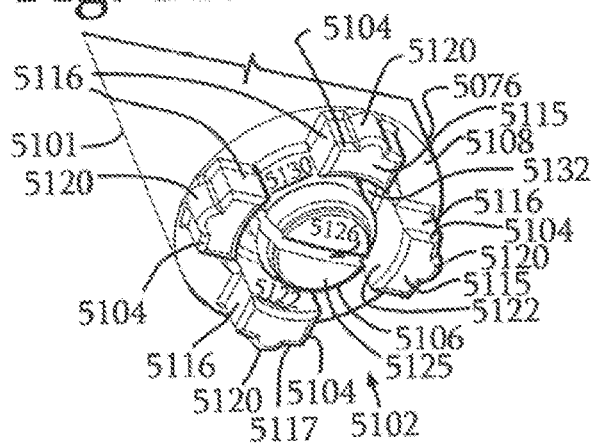

FIG. 117 is an enlarged and partial perspective view of the driver of FIG. 113.

Figure 118:
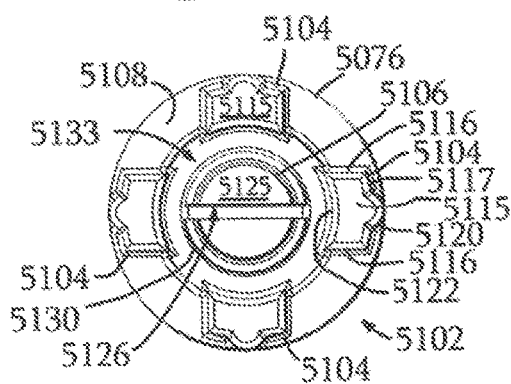

FIG. 118 is an enlarged bottom plan view of the driver of FIG. 113.

Figure 119:
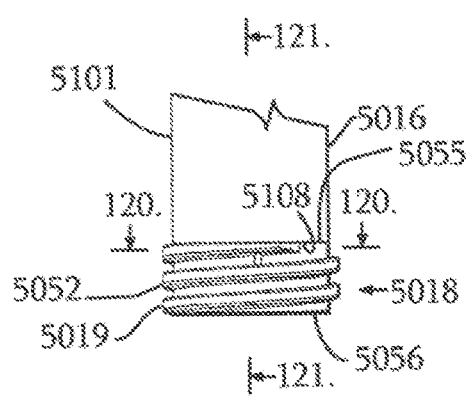

FIG. 119 is a reduced front elevational view of the closure and driver of FIG. 113, the driver shown in engagement with the closure.

Figure 120:
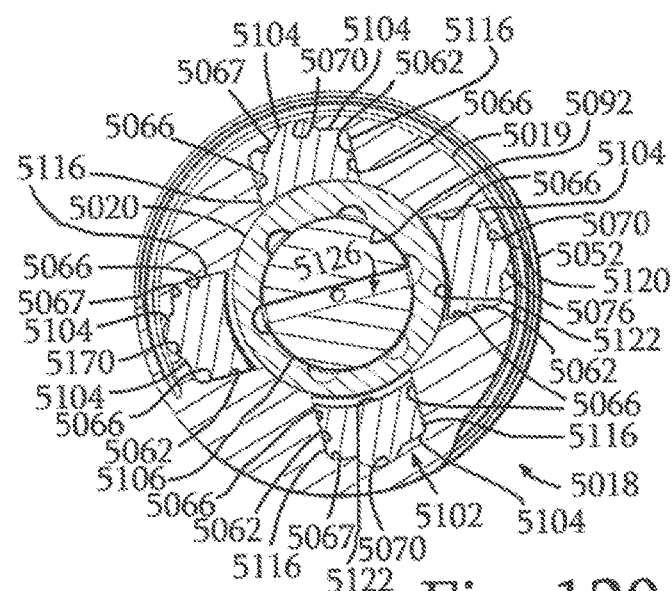

FIG. 120 is an enlarged cross-sectional view taken along the line 120-120 of FIG. 119.

Figure 121:
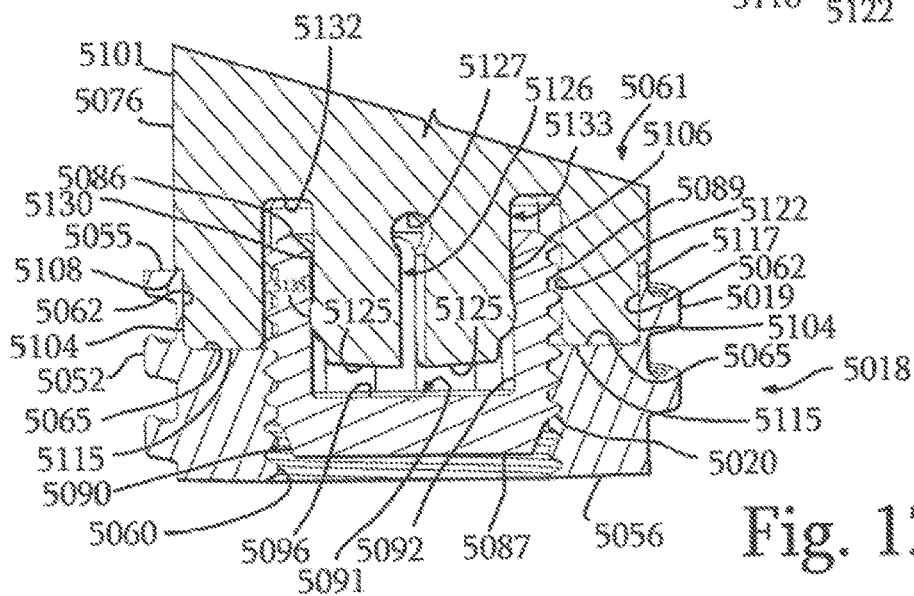

FIG. 121 is an enlarged cross-sectional view taken along the line 121-121 of FIG. 119.

FIG. 122 is a reduced perspective view of the closure of FIG. 111 shown in engagement with a polyaxial bone anchor and capturing a longitudinal connecting member, both in partial perspective view, the connecting member being in the form of a rod, the bone anchor shown implanted into bone (shown schematically in partial and in phantom).

FIG. 123 is an enlarged and partial cross-sectional view taken along the line 123-123 of FIG. 122 and illustrating the polyaxial bone screw of FIG. 122 that includes a receiver, a bone screw shank and a lower compression insert.

FIG. 124 is a reduced perspective view of the compression insert shown in FIG. 123.

FIG. 125 is a reduced and partial cross-sectional view of the receiver and rod of FIG. 123 and further shown with an alternative insert and closure according to an embodiment of the invention, also in partial cross-section.

DETAILED DESCRIPTION OF THE INVENTION

As required, detailed embodiments are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. It is also noted that any reference to the words top, bottom, up and down, and the like, in this application refers to the alignment shown in the various drawings, as well as the normal connotations applied to such devices, and is not intended to restrict positioning of the bone attachment structures, fasteners and tools in actual use.

It is noted that some of the helically wound guide and advancement structures described in detail herein that include a flange form cannot be considered a thread form as flange forms include numerous features, including surfaces and contours in addition to and not anticipated by traditional screw thread technology and nomenclature. However, certain terms used in this application for flange form guide and advancement structures will be similar to those used in thread form nomenclature typically used for v-threads, reverse angle threads, buttress threads and square threads. For example, in traditional v-thread nomenclature, a flank is often described as a thread face running from a root to a crest of a thread form with the root being the bottom or inmost surface joining flanks of two adjacent flanks and the crest being the top or outmost surface joining two flanks of a single thread form. In this application, the term flank may be used to describe such a surface of a v-thread or other type of thread and may also be used to describe certain surfaces of a flange form, such as a loading or thrust surface, but unlike a thread, a flange form flank does not necessarily connect a root to a crest of a particular form. Similarly, a crest or outermost surface of a flange form does not necessarily function as the surface that joins two flanks as other features, such as loaded or unloaded curves, contours or substantially flat surfaces may be located between a flank and a crest. Furthermore, while a root surface of a flange form may typically be substantially cylindrical and a crest surface of a flange form may be at least partially cylindrical, such surface may also be sloped or curved. Thus, an entire outer surface which might be identified as a "crest" surface of a closure plug may or may not be at a uniform distance from a cooperating root surface.

Also, the terms lead, pitch and start, as such terms are used to describe helically wound guide and advancement structures such as v-threads, are to be understood as follows: Lead is a distance along the axis of a closure or plug that is covered by one complete rotation (360 degrees) of the closure with respect to a mating structure. Pitch is the distance from a location on a crest or most outward surface of one thread or flange form structure to the same location on the next thread or adjacent flange form structure. For example in a single-start thread-form, such as a single start, helically wound v-thread closure plug, lead and pitch are the same. Single start means that there is only one helically wound form wrapped around a cylindrical core, or in the case of embodiments of closures according to the present invention, wrapped around a cylindrical closure plug body and thus there is only one start structure or surface at a base or forward end of the closure body that initially engages a mating structure on an open implant. Each time a single start closure rotates one turn (360 degrees), the closure has advanced axially by a width of one thread or helical flange form. Double-start means that there are two threads or forms wrapped around a core body and thus there are two starting surfaces or structures on the closure plug. Therefore, each time a double-start body rotates one turn (360 degrees), such a body has advanced axially by a width of two threads or helical flange forms. Multi-start means that there are at least two and may be up to three or more of threads or other types of forms wrapped around a core body.

Similar to threads, flange forms may also be coarse or fine. Course threads as well as course flange forms are those threads or forms with a larger pitch (fewer forms per axial distance) and fine forms have a smaller pitch (more forms per axial distance).

Also it is noted that the term thrust is traditionally defined as the amount of linear output force produced by a given input torque in a screw and nut drive system. Torque is traditionally defined as the amount of rotational force applied to a screw or nut necessary to produce linear thrust in a screw and nut system.

Closures according to embodiments of the invention are illustrated having an outer plug-like fastener with an outer helically wound flange form and an inner helically wound v-thread that cooperates with an inner set screw having a mating outer helically wound v-thread. However, other flange forms or thread forms, including, but not limited to square, reverse angle and buttress thread forms, for example, may be used on both the outer fastener and the inner set screw. Closures according to embodiments of the invention may be used with a wide variety of medical implants, including, but not limited to mono-axial screws and hooks, hinged or uni-planar screws and hooks and dual multi-piece polyaxial bone screws and hooks. A variety of polyaxial bone screws may also be used with closures of the invention and the illustrated embodiment should not be considered limiting. For example, structures of the invention may be used with bone screws having top loaded bone screw shanks with spherical heads (such as the illustrated bone screw 1) and also with bottom-loaded multi-part screw shanks as well as other types of bottom loaded screws.

With reference to FIGS. 1-32, the reference number 1 generally represents an open implant in the form of a polyaxial bone screw apparatus or assembly that includes a shank 4, that further includes a body 6 integral with an upwardly extending substantially spherical upper portion or head 8; a receiver 10; a compression or pressure insert 14; and a two piece multi-start closure structure or top 18 that includes an outer structure 19 having a double-start helically wound flange-form and a threaded inner plug 20. As will be described in greater detail below, the outer structure 19 mates with the receiver 10 and presses downwardly against the insert 14 that in turn presses against the shank head 8 while the inner plug 20 ultimately presses against a longitudinal connecting member, for example, a rod 21, so as to capture, and fix the longitudinal connecting member 21 within the receiver 10 and thus fix the member 21 relative to a vertebra 17. The receiver 10 and the shank 4 are initially assembled and then assembled with the insert 14 prior to implantation of the shank body 6 into a vertebra 17, as will be described in greater detail below.

The illustrated rod 21 is hard, stiff, non-elastic and cylindrical, having an outer cylindrical surface 22. The rod 21 may be elastic, deformable and/or of a different cross-sectional geometry. The receiver 10 and the shank 4 cooperate in such a manner that the receiver 10 and the shank 4 can be secured at any of a plurality of angles, articulations or rotational alignments relative to one another and within a selected range of angles both from side to side and from front to rear, to enable flexible or articulated engagement of the receiver 10 with the shank 4 until both are locked or fixed relative to each other near the end of an implantation procedure. The two piece closure 18 allows for fixing the polyaxial mechanism of the assembly 1 and then allowing for sliding movement and manipulation of the rod 21 until the rod is fixed in place by the inner set screw 20.

With particular reference to FIGS. 1-4, the shank 4 includes is elongate, with the shank body 6 having a helically wound bone implantable thread 24 extending from near a neck 26 located adjacent to the upper portion or capture structure 8, to a tip 28 of the body 6 and extending radially outwardly therefrom. The illustrated embodiment shows an interleaved shank having a two start 24 lower portion and a four start 25 upper portion. However, other shank thread types may be used, including, but not limited to single and dual start forms as well as other multiple start combinations. During use, the body 6 utilizing the threads 24 and 25 for gripping and advancement is implanted into the vertebra 17 leading with the tip 28 and driven down into the vertebra with an installation or driving tool (not shown), so as to be implanted in the vertebra to near the neck 26, as more fully described in the paragraphs below. The shank 4 has an elongate axis of rotation generally identified by the reference letter A.

The neck 26 extends axially upward from the shank body 6. The neck 26 may be of the same or is typically of a slightly reduced radius as compared to an adjacent upper end or top 32 of the body 6 where the threaded portion 125 terminates. Further extending axially and outwardly from the neck 126 is the shank upper portion 8 that provides a connective or capture apparatus disposed at a distance from the upper end 132 and thus at a distance from the vertebra 17 when the body 6 is implanted in such vertebra.

The shank upper portion 8 is configured for a pivotable connection between the shank 4 and the receiver 10 prior to fixing of the shank 4 in a desired angular position with respect to the receiver 10. The shank upper portion 8 has an outer, convex and substantially spherical surface 34 that extends outwardly and upwardly from the neck 26. The spherical surface 34 participates in a ball and socket joint formed by the shank 4 and surfaces defining an inner cavity of the receiver 10 as will be described in greater detail below. The surface 34 defines a hemisphere 35, shown in phantom in FIGS. 1 and 23, for example, that has a diameter D1 (shown in phantom in FIG. 3) that is a greatest diameter of the spherical surface 34 running through a center of a sphere defined by the surface 34. The surface 34 terminates at a substantially planar ledge or shelf 36 that is annular and disposed perpendicular to the shank axis A. Cut in the surface 34 are two sets of grooves 37 and 38, each set winding helically about the surface 34 and cutting thereinto. The first set of grooves 37 is located above the hemisphere 35 and the second set 38 is located below the hemisphere 35. A smooth central strip or isthmus 40 extends about the hemisphere 35 and is located between the grooved portions 37 and 38. The isthmus 40 provides a slick or smooth surface for engagement with the receiver (specifically an inner edge 98 described in greater detail below) during initial loading of the shank 4 into the receiver 10 chamber or cavity during which the shank and receiver central axes are typically substantially aligned. It is foreseen that other types of grooves or apertures, or other surface treatment, such as knurling, may be utilized in lieu of the grooves 37 and 38 to provide a desired frictional engagement between the shank surface 34 and inner surfaces defining the receiver 10 inner chamber during manipulation and articulation of the shank 4 with respect to the receive 10 as well as adequate locking engagement, once a desired angle of the shank 4 with respect to the receiver 10 is obtained and a longitudinal connecting member is locked in place within the receiver 10 by a closure mechanism in mating engagement with the receiver arms.

Returning to the shank top surface 36, an annular frusto-conical surface 48 is located adjacent thereto and extends inwardly toward the axis A. A counter sunk substantially planar and annular base or seating surface 49 partially defines an internal drive feature or imprint, generally 50. The illustrated internal drive feature 50 is an aperture formed in the frusto-conical surface 48 and the top surface 36 and is sized and shaped for a positive, non-slip engagement by a shank driving tool (not shown). The drive aperture or feature 50 is a poly drive, specifically, having a hexa-lobular geometry formed by a substantially cylindrical wall 52 communicating with equally spaced radially outwardly extending (from the axis A and from the cylindrical surface 52) rounded cut-outs or lobes 53 that are formed in the surface 48 and are located near the top surface 36. The wall 52 terminates at the drive seating surface 49 and the lobes 53 each terminate at a step 54 that is raised slightly from the seating surface 49. Although the hexa-lobular drive feature 50 is preferred for torque sensitive applications as the lobes are able to receive increased torque transfer as compared to other drive systems, it is noted that other drive systems may be used, for example, a hex drive, star-shaped drive or other internal drives such as slotted, tri-wing, spanner, two or more apertures of various shapes, and the like. The seat or base 49 of the drive feature 50 is disposed perpendicular to the axis A with the drive feature 50 otherwise being coaxial with the axis A.

The shank 4 shown in the drawings is cannulated, having a small central bore 55 extending an entire length of the shank 4 along the axis A. The bore 55 is defined by an inner cylindrical wall of the shank 4 and has a circular opening at the shank tip 28 and an upper opening communicating with the internal drive 50 at the surface 49. The bore 55 is coaxial with the threaded body 6 and the upper portion 8. The bore 55 provides a passage through the shank 4 interior for a length of wire (not shown) inserted into the vertebra 17 prior to the insertion of the shank body 6, the wire providing a guide for insertion of the shank body 6 into the vertebra 17.

To provide a biologically active interface with the bone, the threaded shank body 6 may be coated, perforated, made porous or otherwise treated. The treatment may include, but is not limited to a plasma spray coating or other type of coating of a metal or, for example, a calcium phosphate; or a roughening, perforation or indentation in the shank surface, such as by sputtering, sand blasting or acid etching, that allows for bony ingrowth or ongrowth. Certain metal coatings act as a scaffold for bone ingrowth. Bio-ceramic calcium phosphate coatings include, but are not limited to: alpha-tri-calcium phosphate and beta-tri-calcium phosphate ($Ca_3(PO_4)_2$), tetra-calcium phosphate ($Ca_4PO_1$), amorphous calcium phosphate and hydroxyapatite ($Ca_{10}(PO_4)_6(OH)_2$). Coating with hydroxyapatite, for example, is desirable as hydroxyapatite is chemically similar to bone with respect to mineral content and has been identified as being bioactive and thus not only supportive of bone ingrowth, but actively taking part in bone bonding.

With particular reference to FIGS. 1 and 5-10, the receiver 10 has a generally U-shaped appearance with a partially discontinuous substantially cylindrical inner profile and a partially cylindrical and partially planar outer profile. The receiver 10 has an axis of rotation B that is shown in FIG. 1 as being aligned with and the same as the axis of rotation A of the shank 4, such orientation occurring when the shank 4 is first downloaded into the receiver 10 during initial assembly. After the receiver 10 is pivotally attached to the shank 4, the axis B is typically disposed at an angle with respect to the axis A.

Figure 30:
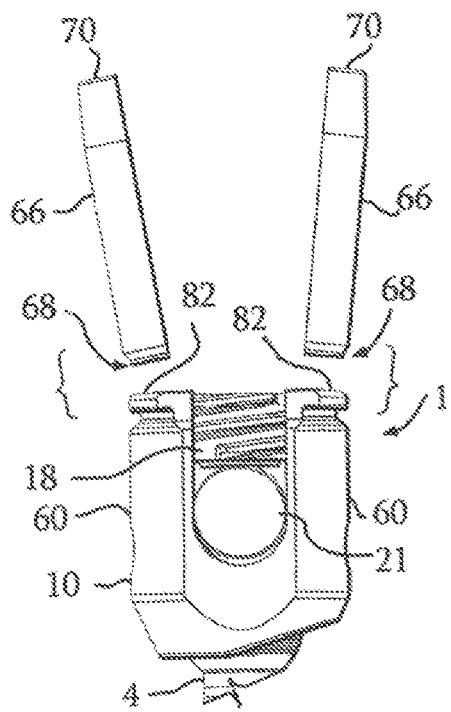
FIG. 30 is a reduced and partial front elevational view, similar to FIG. 29 further showing removal of the receiver extension tabs.

The receiver 10 includes a base portion 58 having partially frusto-conical, partially cylindrical and also partially planar 59 outer surface portions. The base 58 is integral with a pair of opposed upstanding arms 60. A cavity, generally 61, is located within the base 58. The arms 60 form a cradle and define a U-shaped channel 62 beginning at a U-shaped lower seat 64 located adjacent each of the opposed planar base portions 59, the channel 62 having a width for operably snugly receiving the rod 21 between the arms 60. The channel 62 communicates with the base cavity 61. In the illustrated embodiment, an arm tab or break-off extension 66 is connected to each arm 60 to increase an initial length of the arm 60 and thus form a rod receiving passageway 67 between opposed extensions 66, thereby increasing a length of the rod receiving channel 62 by a length of the passageway 67. A purpose of the passageway 67 is to enable capture of the rod at a greater distance from the vertebra 17 whereby the rod 21 can be captured by the closure 18 at an opening 69 near top surfaces 70 of the tabs 66 and "reduced" or urged toward a seated position within the channel 62 and toward the channel seat 64 by advancement of the closure 18. This provides effective leverage in reducing a position of the rod 21 or the vertebra 17 itself. For such purpose, inner surfaces of the tabs 66 are provided with the same closure guide and advancement structure as inner surfaces of the arms 60 as will be described in greater detail below. The tabs 66 are connected to the arms 60 by reduced or otherwise weakened regions, generally 68, that include both inner and outer surface features. In the illustrated embodiment, the arms 60 are integral with the tabs 66 at the region 68 and such region is partially weakened by an outer groove in the form of a v-cut 71 that extends around a lower perimeter of each break-off extension tab 66. The regions 68 are strong enough to enable the rod 21 to be urged toward a seated position by the closure 18, both the rod 21 and closure 18 moving past the regions 68 and into the channel 62 defined by the stronger arms 60. The weakened regions 68 allow for breaking off or separating the extensions 66 from the arms 60 at the groove or notch 71 by pivoting or bending the extensions 66 back and forth at the regions 68 while the arms 60 remain in place, typically after the closure 18 has passed between the extensions 66, resulting in a low profile implanted structure as shown in FIG. 30.

Each of the arms 60 and connected tabs 66 has an interior surface that has a cylindrical profile that further includes a partial helically wound guide and advancement structure or flange 72 extending radially inwardly toward the axis B. Each guide and advancement structure 72 begins near the tab top surface 70 and terminates at an annular run-out surface 74 located adjacent an inner discontinuous cylindrical surface 76 that partially defines a run-out area for the closure 18. The run-out area is also partially defined by a discontinuous annular surface 78 located adjacent the surface 76. Both the discontinuous annular surfaces 74 and 78 are disposed substantially perpendicular to the axis B, while the surface 76 is parallel to the axis B.

In the illustrated embodiment, the guide and advancement structures 72 are each in the form of a partial helically wound interlocking flange form configured to mate under rotation with the dual start closure structure 18. Thus, unlike single start advancement structures, the helical forms 72 on the opposing inner arm and extension surfaces that are configured to mate with the dual start closure top 18 are reverse or flipped images of one another, the structures 72 on each arm 60 being aligned with respect to the receiver axis B, so that each closure structure start (reference number 203 as described below) are simultaneously engaged and captured at each arm extension 66 and thereafter each arm 60 at the same time. Although the illustrated guide and advancement structures 72 are shown as interlocking flange forms, it is foreseen that the guide and advancement structures 72 could alternatively be of a different geometry, such as a square-shaped thread, a buttress thread, a reverse angle thread or other thread-like or non-thread-like helically wound discontinuous advancement structure for operably guiding under rotation and advancing a multi-start closure structure downward between the receiver arms 60, as well as eventual torquing when the closure structure 18 abuts against the compression insert 14. Further information on interlocking flange forms is provided, for example, in Applicant's U.S. Pat. No. 6,726,689.

Located along the flange form 72, a flange form segment, generally 79 at the weakened region 68 generally opposite the groove or notch 71 includes a substantially horizontally positioned recess 80 cut or otherwise formed in the flange form segment 79 to further weaken each region 68. Thus, the recess 80 is located mostly within the segment 79, but since it runs horizontally (i.e., substantially perpendicular to the receiver axis B), it also runs slightly counter to the helical slope of the flange form 72. Each recess 80 is curved and elongate and disposed cross-wise or substantially transverse to the flange form section 79. For example, with reference to the arm 60 shown in FIG. 8, the recess 80 cuts into the weakened region 68 where a respective arm 60 joins with an adjacent extension 66, the curved and elongate recess 80 beginning at a lower end 82 and terminating at an opposed upper end 83 of the flange form segment 79, while otherwise leaving the flange form 72 intact. Stated in another way, the recess 80 cuts into both a lead portion and a trailing portion of each of the flange form segments 79 located near and directly above the opposed arms 60 and substantially opposite the notch 71, thus further weakening portions of each of the regions 68, without destroying the flange form path, so that the closure 18 is not derailed by the recess 80 or otherwise prohibited from moving downwardly into the channel 62.

Each of the arms 60 further include a top surface 82 located directly below the weakening notch 71. A tool receiving notch or undercut 84 is formed below the top surface 82 and a remainder of each arm 60 is a substantially cylindrical surface 86. Each arm break-off extension 66 includes a lower outer cylindrical surface 87 spanning from the notch 71 to adjacent an upper frusto-conical surface 88 that terminates at the top surface 70.

Returning to the arm 60 outer surfaces 86, located substantially centrally in each arm 60 is a shallow recess 90 formed in the surface 86. The recess 90 does not extend all the way through the arm 60 but rather terminates at a crimping wall 92, the wall 92 being relatively thin for pressing against the compression insert 14 as will be described in greater detail below. In the illustrated embodiment, the wall 92 has an outer concave and conical surface. However, in other embodiments, the wall 92 may be planar or have other surface geometries. The recess 90 being sized and shaped for receiving a tool (not shown) used to press or crimp some or all of the wall 92 material inwardly toward the axis B and against portions of the compression insert 14 as will be described in greater detail below, to prohibit rotation of the insert 14 with respect to the receiver 10.

The receiver 10 is a one-piece or integral structure and is devoid of any spring tabs or collet-like structures. In some embodiments, the insert and/or receiver are configured with further structure for blocking rotation of the insert with respect to the receiver, such as the crimp walls 92, but allowing some up and down movement of the insert with respect to the receiver during the assembly and implant procedure. Some or all of the apertures and grooves described herein, including, but not limited to the grooves or notches 84 and the apertures 90 may be used for holding the receiver 10 during assembly with the insert 14 and the shank 4; during the implantation of the shank body 6 into a vertebra after the shank is pre-assembled with the receiver 10; during assembly of the bone anchor assembly 1 with the rod 21 and the closure structure 18; and during angular adjustment of the shank 4 with respect to the receiver 10 as will be described in greater detail below. It is foreseen that tool receiving grooves or apertures may be configured in a variety of shapes and sizes and be disposed at other locations on the receiver arm 60 outer and/or inner surfaces as well as surfaces defining the base 58.

Figure 8:
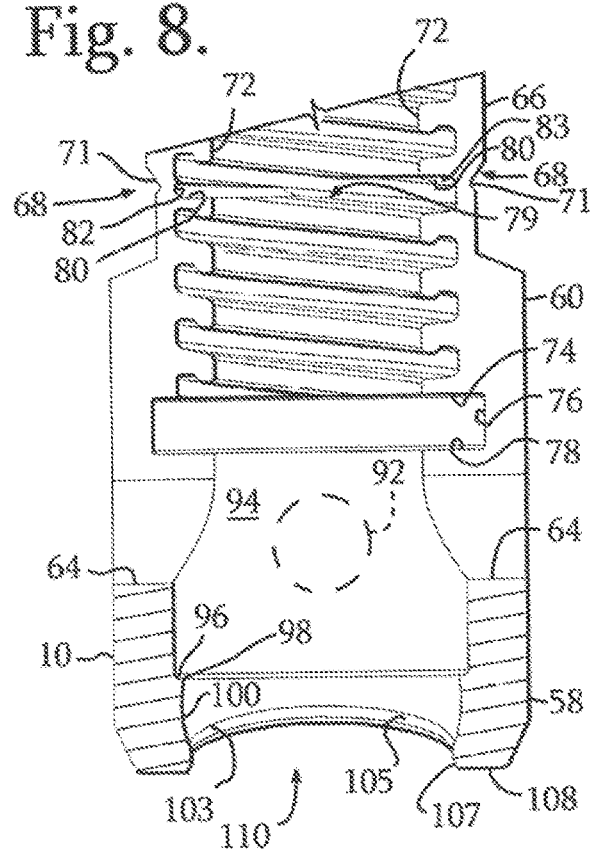
FIG. 8 is a cross-sectional view taken along the line 8-8 of FIG. 6.
Figure 9:
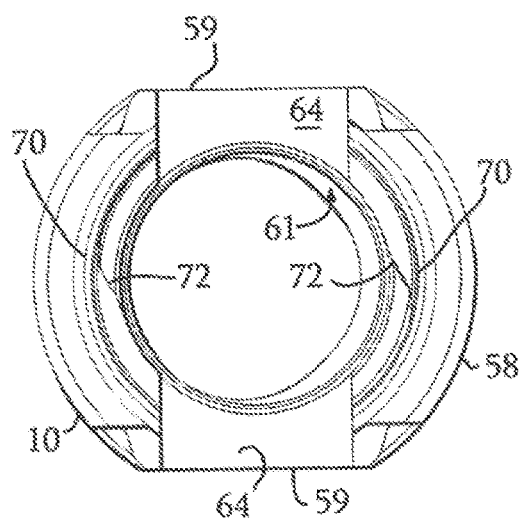
FIG. 9 is an enlarged top plan view of the receiver of FIG. 5.
Figure 10:
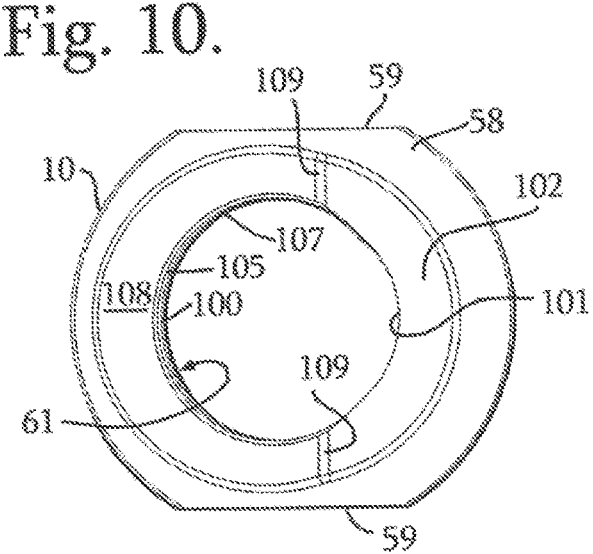
FIG. 10 is a bottom plan view of the receiver of FIG. 9.
Figure 11:
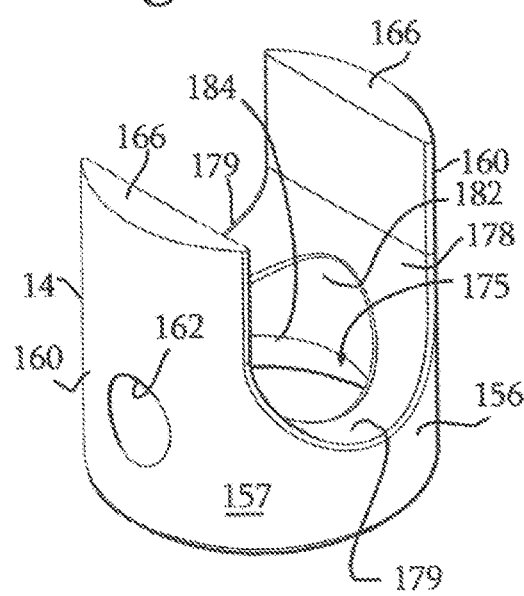
FIG. 11 is an enlarged perspective view of the compression insert of FIG. 1.
Figure 12:
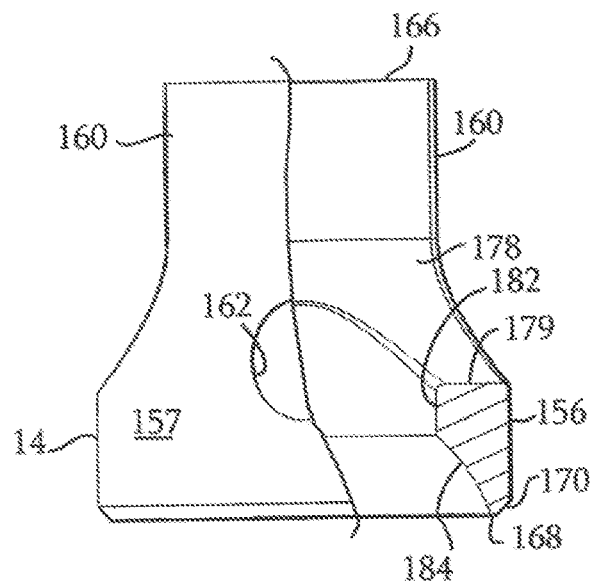
FIG. 12 is an enlarged side elevational view of the insert of FIG. 11 with portions broken away to show the detail thereof.
Figure 13:
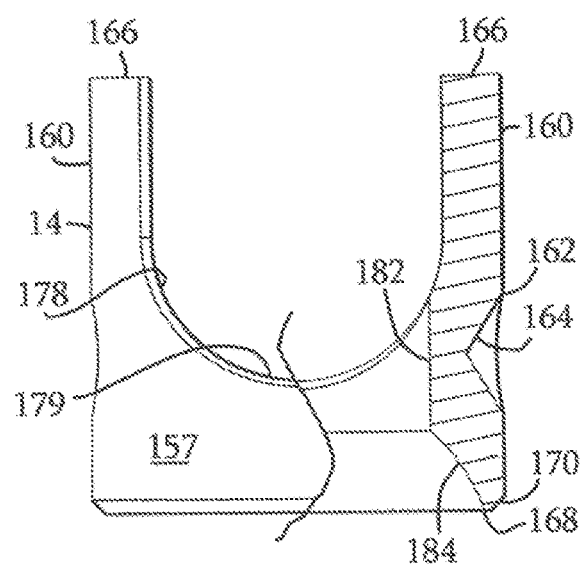
FIG. 13 is a front elevational view of the insert of FIG. 12 with portions broken away to show the detail thereof.
Figure 14:
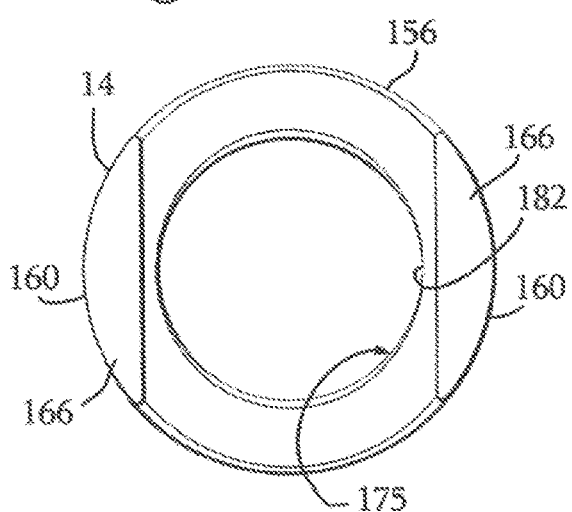
FIG. 14 is a top plan view of the insert of FIG. 12.
Figure 15:
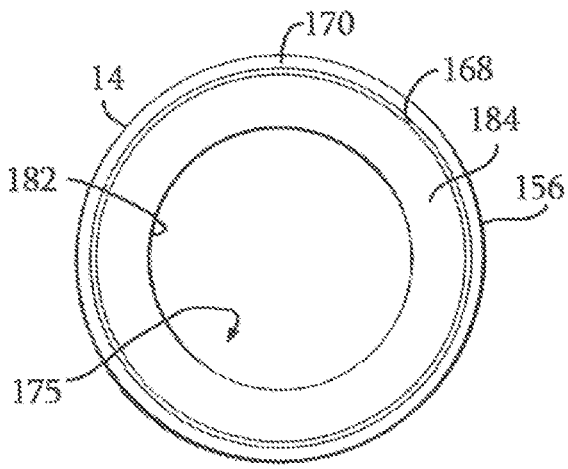
FIG. 15 is a bottom plan view of the insert of FIG. 12.
Figure 24:
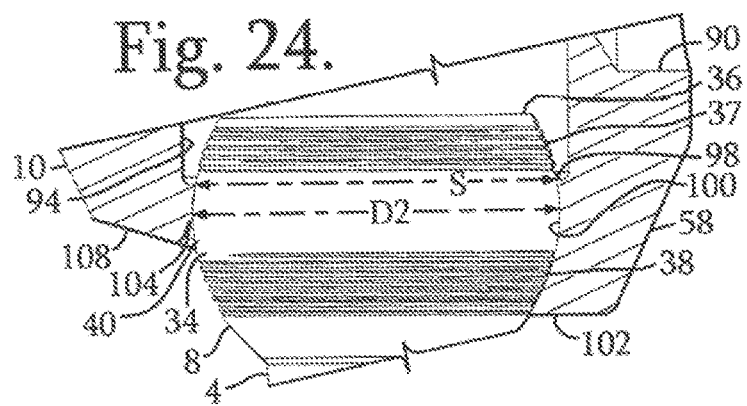
FIG. 24 is an enlarged and partial front elevational view with portions broken away of the receiver showing the shank in a stage of assembly with the receiver subsequent to what is shown in FIG. 23.

With particular reference to FIGS. 6 and 8, returning to the interior arm surfaces, and as previously described herein, located below each discontinuous guide and advancement structure 72 are the surfaces 74, 76 and 78 defining closure run-out areas. Below and adjacent to each discontinuous annular surface 78 is a cylindrical surface 94 that defines a lower portion of each arm 60 and continues downwardly, defining a portion of the base cavity 61. The surface 94, as well as the surfaces 74, 76 and 78 are coaxial with the receiver central axis B. Each of the crimp walls 92 are located centrally along the surface 94 and a general position of one of the crimp walls 92 is shown in phantom in FIG. 8. Located adjacent to and below the now continuous cylindrical wall 94 is a narrow annular ledge 96 that extends inwardly toward the axis B. The ledge 96 is substantially planar and is disposed perpendicular to the axis B. The ledge terminates at a circular edge 98 that also defines a beginning of a spherical surface 100. The spherical surface 100 defines a hemispheric void that has a large or great diameter D2 running therethrough as shown in FIG. 24, for example. Also with reference to FIG. 24, a diameter S of the circular edge 98 is less than the diameter D2 as the edge 98 defines a spheric section of the surface 100 that does not run through a center of the sphere defined by the surface 100. The spherical surface diameter D2 is the same or substantially similar to the shank upper portion diameter D1. Thus, as will be described in greater detail below, after the shank upper portion 8 is pushed or pulled past the edge 98 during assembly of the shank 4 with the receiver 10, the shank surface 34 is in tight, but movable, frictional engagement with the receiver surface 100.

A portion of the spherical surface 100 terminates at a lower edge 101 that defines a bottom surface 102 of the receiver 10. The bottom surface 102 is substantially planar and is disposed substantially perpendicular to the receiver axis B. Another portion of the spherical surface 100 terminates at a lower edge 103 that is disposed at an acute angle with respect to the lower edge 101. Thus, the edge 103 cuts upwardly into the spherical surface 100 reducing an area of the surface 100 located beneath one of the arms 60, creating clearance for an increased angle of pivot between the shank 4 and the receiver 10 when the shank 4 is pivoted toward the lower edge 103. The lower edge 103 is also defined by an undercut surface 104 that terminates at a partially cylindrical surface 105. However, unlike other cylindrical surfaces of the receiver, such as the surface 94, the surface 105 is not coaxial with the receiver axis B. Rather, a central axis of the surface 105 is disposed at an angle with respect to the axis B, such axis being perpendicular to a plane running through the lower edge 103. The surface 105 terminates at a partially circular edge 106. The edge 106 is partially defined by a partial frusto-conical surface 107 that terminates at a bottom surface 108. The bottom surface 108 is substantially parallel and runs parallel to the plane that runs through the lower edge 103. The bottom surface 108 and the bottom surface 102 join at curved transition surfaces 109. A receiver lower opening, generally 110 is defined by the bottom surfaces 102 and 108. It is noted that the illustrated lower surfaces 102, 105, 107 and 108 and corresponding edges may be greater or fewer in number and may include other geometries. Furthermore, in other embodiments, the bottom surface 102 may extend along an entire bottom of the receiver 10 when a favored extended angle of pivot is not desired or required. Additionally, the receiver cavity 61 may be defined by other additional sloped, stepped or chamfered surfaces as desired for ease in assembly of the shank and other top loaded components.

With particular reference to FIGS. 1 and 11-15, the compression insert 14 is illustrated that is sized and shaped to be received by and down-loaded into the receiver 10 at the upper opening 69. The compression insert 14 has an operational central axis that is the same as the central axis B of the receiver 10. In operation, the insert advantageously frictionally engages the bone screw shank upper portion 8 as well as the closure outer structure 19, locking the shank 4 in a desired angular position with respect to the receiver 10 that remains in such locked position even if, for example, the rod 21 is placed in and out of a slidable relation with the closure top inner threaded plug 20. Such locked position may also be released by the surgeon if desired by loosening the outer structure 19. The insert 14 is preferably made from a solid resilient material, such as a stainless steel or titanium alloy, so that portions of the insert 14 may be grasped, pinched or pressed, if necessary.

The compression insert 14 includes a body 156 with an outer substantially cylindrical surface 157 and may, in some embodiments include other surfaces, chamfers or cut-outs to provide clearance between the insert 14 and other bone anchor components. The body 156 is integral with a pair of upstanding arms 160. The cylindrical surface 157 extends upwardly and forms an outer surface of each of the arms 160. Thus, each arm outer surface is substantially cylindrical in profile but it is foreseen that in other embodiments, the surface may be made from a variety of facets or faces as well as cut-outs to provide for clearance with other components of the assembly 1. Located on the body 156 below each upstanding arm 160 is a shallow aperture 162 formed in the surface 157 that in the illustrated embodiment is a substantially conical surface 164 that extends toward the insert central axis, but does not extend completely through the respective arm 160. The aperture 162 is sized and shaped for receiving material from the receiver crimping wall 92. The apertures 162 are each substantially centered on the respective arm 160 and are opposed to one another. After the insert 14 is placed within the receiver 10 and the receiver crimp walls 92 are pressed into the insert apertures 162, rotation of the insert 15 with respect to the receiver 10 is prohibited as well as any upward movement of the insert 14 out of the receiver 10. In some embodiments of the invention, the apertures 162 are slightly elongate and designed to allow for some upward and downward movement of the insert 14 with respect to the receiver 10. The insert 14 further includes substantially planar arm top surfaces 166 located opposite a bottom surface that in the illustrated embodiment is a substantially planar, narrow annular rim 168. The surfaces 166 slope radially inwardly and downwardly at about a two degree incline. A frusto-conical surface 170 joins the rim 168 to the insert outer cylindrical surface 157.

Returning to the inner surfaces of the insert 14, a through bore, generally 175, is disposed primarily within and through the body 156 and communicates with a generally U-shaped through channel formed by a saddle surface 178 that is substantially defined by the upstanding arms 160. Near the top surfaces 166, the saddle surface 178 is substantially planar. The saddle 178 has a curved lower seat 179 sized and shaped to closely, snugly engage the rod 21 or other longitudinal connecting member. It is foreseen that an alternative embodiment may be configured to include planar holding surfaces that closely hold a square or rectangular bar as well as hold a cylindrical rod-shaped, cord, or sleeved tensioned cord longitudinal connecting member. The bore, generally 175, is substantially defined at the body 156 by an inner cylindrical surface 182 that communicates with the seat 179 and also communicates with a lower concave, radiused or otherwise curved portion 184, that in some embodiments may include shank gripping surfaces or ridges, the surface portion 184 generally having a radius for closely mating with the surface 34 of the shank upper portion 8. The portion 184 terminates at the base surface 168. It is foreseen that the lower shank engaging portion 184 may additionally or alternatively include a roughened or textured surface or surface finish, or may be scored, knurled, or the like, for enhancing frictional engagement with the shank upper portion 8.

The compression insert 14 through bore 175 is sized and shaped to receive a driving tool (not shown) therethrough that engages the shank drive feature 50 when the shank body 6 is driven into bone with the receiver 10 attached. Also, in some embodiments of the invention, the bore may receive a manipulation tool (not shown) used for releasing the insert 14 from a locked position with the receiver 10, the tool pressing down on the shank head 8 and also gripping the insert 14 at apertures or other tool receiving features (not shown). Each of the arms 160 and the insert body 156 may include more surface features, such as cut-outs notches, bevels, etc. to provide adequate clearance for inserting the insert 14 into the receiver and cooperating with other components of the assembly. The insert body 156 and arm 160 cylindrical surface 157 has a diameter slightly smaller than a diameter between crests of the guide and advancement structure 72 of the receiver 10, allowing for top loading of the compression insert 14 into the upper opening 69.

With reference to FIGS. 1 and 27-32, the illustrated elongate rod or longitudinal connecting member 21 (of which only a portion has been shown) can be any of a variety of implants utilized in reconstructive spinal surgery, but is typically a cylindrical, elongate structure having the outer substantially smooth, cylindrical surface 22 of uniform diameter. The rod 21 may be made from a variety of metals, metal alloys and deformable and less compressible plastics, including, but not limited to rods made of elastomeric, polyetheretherketone (PEEK) and other types of materials, such as polycarbonate urethanes (PCU) and polyethylenes.

Longitudinal connecting members for use with the assembly 1 may take a variety of shapes, including but not limited to rods or bars of oval, rectangular or other curved or polygonal cross-section. The shape of the insert 14 may be modified so as to closely hold the particular longitudinal connecting member used in the assembly 1. Some embodiments of the assembly 1 may also be used with a tensioned cord. Such a cord may be made from a variety of materials, including polyester or other plastic fibers, strands or threads, such as polyethylene-terephthalate. Furthermore, the longitudinal connector may be a component of a longer overall dynamic stabilization connecting member, with cylindrical or bar-shaped portions sized and shaped for being received by the compression insert 14 of the receiver having a U-shaped, rectangular- or other-shaped channel, for closely receiving the longitudinal connecting member. The longitudinal connecting member may be integral or otherwise fixed to a bendable or damping component that is sized and shaped to be located between adjacent pairs of bone screw assemblies 1, for example. A damping component or bumper may be attached to the longitudinal connecting member at one or both sides of the bone screw assembly 1. A rod or bar (or rod or bar component) of a longitudinal connecting member may be made of a variety of materials ranging from deformable plastics to hard metals, depending upon the desired application. Thus, bars and rods of the invention may be made of materials including, but not limited to metal and metal alloys including but not limited to stainless steel, titanium, titanium alloys and cobalt chrome; or other suitable materials, including plastic polymers such as polyetheretherketone (PEEK), ultra-high-molecular weight-polyethylene (UHMWP), polyurethanes and composites, including composites containing carbon fiber, natural or synthetic elastomers such as polyisoprene (natural rubber), and synthetic polymers, copolymers, and thermoplastic elastomers, for example, polyurethane elastomers such as polycarbonate-urethane elastomers.

With reference to FIGS. 1 and 16-21, the closure 18 is illustrated. The closure 18 includes two pieces: the outer structure or fastener 19 having an outer guide and advancement structure in the form of a double-start helically wound splay control flange form and an inner thread sized and shaped for cooperation with the coaxial threaded inner plug 20, the helically wound forms of both of the structures 18 and 19 being coaxial and having a central axis of rotation that is the same as the axis B of the receiver 10 when assembled with the receiver 10.

As will be described in greater detail below, the outer structure 19 of the closure top 18 mates under rotation with the receiver 10 having the central axis B, the structure 19 pressing downwardly against the insert 14 arm top surfaces 166, the insert surface 184 in turn pressing downwardly against the shank head 8 that in turn frictionally engages the receiver 10, locking the polyaxial mechanism of the bone anchor 1, (i.e., fixing the shank 4 at a particular angle with respect to the receiver 10). The closure inner plug 20 ultimately frictionally engages and presses against the longitudinal connecting member, for example, the rod 21, so as to capture, and fix the longitudinal connecting member 21 within the receiver 10 and thus fix the member 21 relative to the vertebra 17.

The multi-start closure 18 outer splay control structure 19 has a double or dual start helically wound guide and advancement structure in the form of a pair of identical helically wound forms 202, each illustrated as a flange form that operably joins with mating flange form structures 72 disposed on the arms 60 and break-off extensions 66 of the receiver 10 to result in an interlocking guide and advancement structure or arrangement. Although a particular flange form structure and relationship is shown herein, it is noted that flange forms may be of a variety of geometries, including, for example, those described in Applicant's U.S. patent application Ser. No. 11/101,859 filed Apr. 8, 2005 (US Pub. No. 2005/0182410 published Aug. 18, 2005), which is also incorporated by reference herein.

Figure 18:
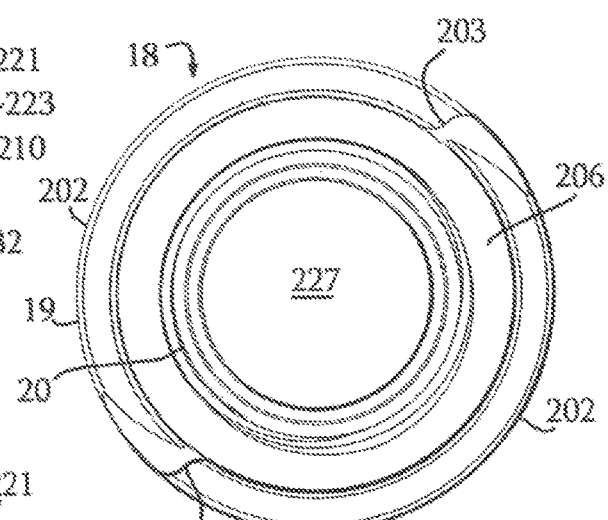
FIG. 18 is a bottom plan view of the closure of FIG. 16.

Each form 202 includes a start surface or structure 203 and thus, as shown in FIG. 18, the structure 19 includes two starts 203. Each of the forms 202 may be described more generically as being positioned as an inner flange of the overall structural arrangement as each form 202 extends helically on an inner member that in the illustrated embodiment is the closure structure 19. The flange form 72, on the other hand, extends helically within an outer member that in the illustrated embodiment is in the form of the receiver 10 arms 60 and extensions 66. The flanges 202 and 72 cooperate to helically guide the inner member or structure 19 into the outer member or receiver 10 when the inner member 19 is rotated and advanced into the arms of the outer member 10. The inner and outer flanges 202 and 72 have respective splay regulating contours to control splay of the receiver arms 60 when the inner member 19 is strongly torqued therein. In some embodiments of the invention the member 19 may be a substantially solid plug that is eventually torqued against the rod 21 to clamp the rod within the receiver 10. In the illustrated embodiment, the inner threaded plug 20 is the feature that ultimately clamps down on the rod 21 and also mates with the member 19 via a v-thread that will be described in greater detail below. It is noted that the anti-splay structure provided by the mating flange forms 202 and 72 may also be utilized on single-piece cylindrical plug-like closures as well as on other types of one and two piece nested closures, for example, those having a break-off head that separates from the closure when installation torque exceeds a selected level, such as the closures disclosed in Applicant's U.S. Pat. No. 7,967,850 (see, e.g., FIGS. 22-25 and accompanying disclosure), that is incorporated by reference herein.

With particular reference to FIGS. 16-21, the illustrated fastener structure 19 includes a through-bore 204 extending along the central axis and running completely through the fastener structure 19 from a top surface 205 to a bottom surface 206. The bottom surface 206 is substantially planar and annular and configured for being received between the receiver arms 60 and for exclusively abutting against the substantially planar top surfaces 166 of the insert arms 160, the insert 14 arms 160 being configured to extend above the rod 21 such that the closure surface 206 is always spaced from the rod 21 or other longitudinal connecting member portion received by the insert arms 160 and located within the receiver 10.

As indicated previously, the closure or fastener structure 19 is substantially cylindrical and the two flange forms 202 project substantially radially outwardly. The closure structure 18 helically wound flange form 202 start structures 203 are located on opposite sides of the closure structure and are both located adjacent the bottom surface 206. When the closure structure 19 is rotated into the receiver 10 between receiver arms 60, each having the flange form 72 guide and advancement structure, the start 203 engages mating guide and advancement structure 72 on one arm break-off extension arm 66 and the opposite start 203 simultaneously engages guide and advancement structure flange form 72 on the opposing arm extension 66, both forms 202 being simultaneously captured by the mating forms 72 on the opposed arm extensions 66. As the structure 19 is rotated, the structure advances axially downwardly between the break-off extensions 66 and then the arms 60 and then presses evenly down upon the insert 14 arm top surfaces 166. Each time the illustrated duel- or double-start closure plug 19 is rotated one complete turn or pass (three hundred sixty degrees) between the implant arm extensions or arms, the closure 19 advances axially toward and then into the receiver 10 and toward the insert 14 by a width of two helical flange forms. The closure 19 is sized for at least one complete rotation (three hundred sixty degree) of the closure 19 with respect to the receiver 10 open arms 60 to substantially receive the closure 18 between the implant arms. Multi-start closures of the invention may have two or more coarse or fine helical forms, resulting in fewer or greater forms per axial distance spiraling about the closure plug body and thus resulting in plugs that rotate less or more than one complete rotation to be fully received between the implant arms. Preferably, helically wound forms of the multi-start closure of the invention are sized so as to spiral around a cylindrical plug body thereof to an extent that the closure rotates at least ninety-one degrees to fully or substantially receive the closure 19 between the arms of the bone screw receiver or other open implant. Particularly preferred guide and advancement structures are sized for at least one complete turn or pass (three-hundred sixty degree) of the closure between the receiver 10 arms 60 and as many as two to three rotations to be fully received between implant arms.

At the closure structure base or bottom surface 206 and running to near the top surface 205, the bore 204 is substantially defined by a guide and advancement structure shown in the drawing figures as an internal V-shaped thread 210. The thread 210 is sized and shaped to receive the threaded set screw 20 therein as will be discussed in more detail below. Although a traditional V-shaped thread 210 is shown, it is foreseen that other types of helical guide and advancement structures may be used. Adjacent the closure top surface 205, the bore 204 is defined by a discontinuous cylindrical surface 212 that runs from the top surface 205 to the v-thread 210. The cylindrical surface 212 has a radius measured from the central axis that is the same or substantially similar to a radius from the central axis to a crest 214 the v-thread 210. In the illustrated embodiment, a distance from the top surface 205 to the v-thread 210 measured along the surface 212 is greater than a pitch of the v-thread 210, the surface 212 acting as a stop for the inner set screw or plug 20, preventing the screw 20 from rotating upwardly and out of the structure 19 at the top surface 205. However, it is foreseen that the surface 212 may be taller or shorter than shown, and that in some embodiments, a radially inwardly extending overhang or shoulder may be located adjacent the top surface 205 to act as a stop for the set screw 20. In other embodiments, the set screw 20 may be equipped with an outwardly extending abutment feature near a base thereof, with complimentary alterations made in the fastener 19, such that the set screw 20 would be prohibited from advancing upwardly out of the top of the structure 19 due to abutment of such outwardly extending feature of the set screw against a surface of the fastener 19. In other embodiments, the central set screw may be rotated or screwed completely through the outer ring member.

Figure 16:
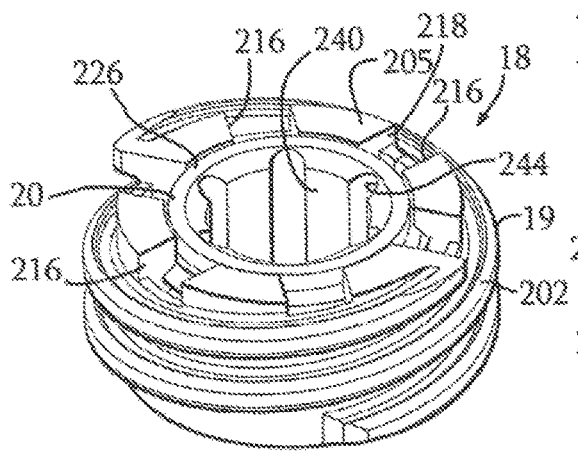
FIG. 16 is an enlarged perspective view of the two piece dual start closure of FIG. 1.
Figure 17:
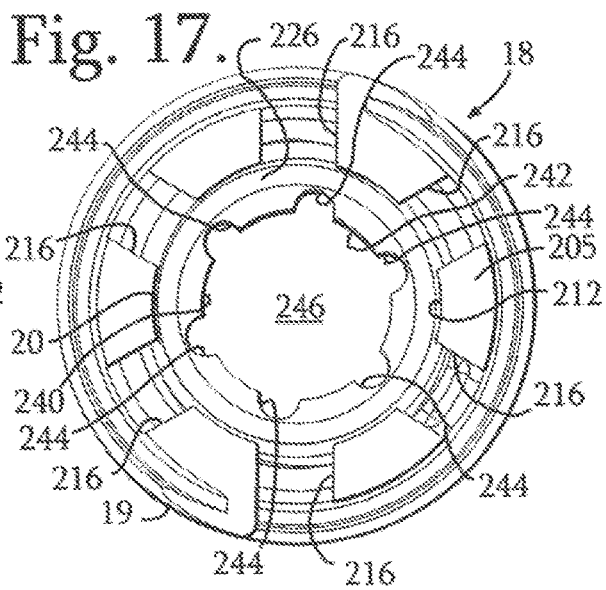
FIG. 17 is a top plan view of the closure of FIG. 16.
Figure 19:
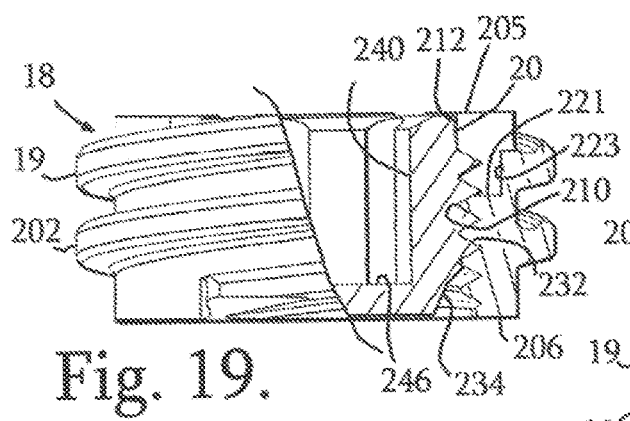
FIG. 19 is a front elevational view of the closure of FIG. 16 with portions broken away to show the detail thereof.
Figure 20:
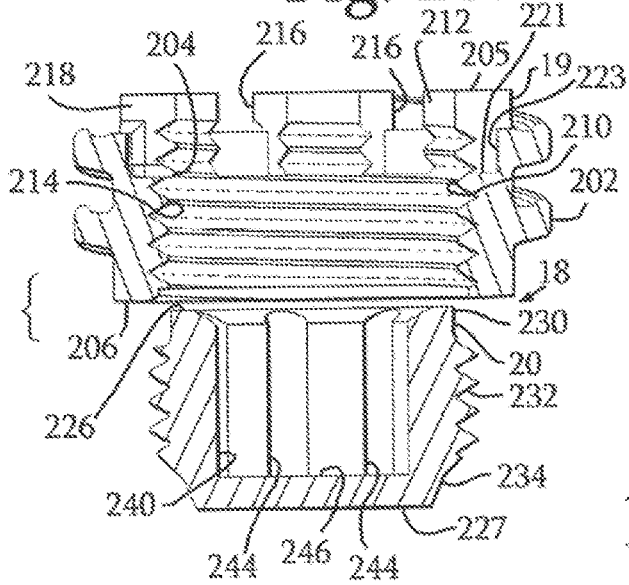
FIG. 20 is an exploded front elevational view of the closure of FIG. 16 with portions broken away to show the detail thereof.
Figure 21:
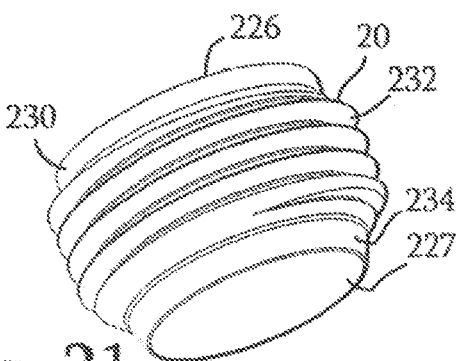
FIG. 21 is a perspective of the inner set screw of the closure of FIG. 16.

With particular reference to FIGS. 16, 17 and 20, formed in the top surface 205 of the fastener 19 is a cross-slotted internal drive, made up of three spaced cross-slots, or stated in other way, six equally spaced radial slots 216. An upper portion 218 of each slot 216 extends from the bore 204 radially outwardly to the flange form 202 root and thus completely through the top surface 205 of the structure 19, each upper portion 218 being adjacent the cylindrical surface 212 along an entire height thereof. Another, lower portion 219 of each slot 116 extends downwardly below the cylindrical surface 212 and cuts into the v-thread 210, terminating at a substantially planar base surface 221 and being partially defined by a cylindrical wall 223. The cross-slotted drive slots or grooves 216 are advantageous in torque sensitive applications: the more slots, the greater the torque sensitivity. Further, the slot lower portions 219 provide additional surfaces 221 and 223 for gripping by a cooperating drive tool (not shown) sized and shaped to be received by the slot lower portions 219.

The up-loadable set screw 20 has a substantially annular and planar top 226 and a substantially circular planar bottom 227. The screw 20 is substantially cylindrical in shape and coaxial with the outer fastener 19. The screw 20 is substantially cylindrical and includes an upper outer cylindrical surface 230 adjacent a v-thread surface portion 232 that in turn is adjacent to a lower frusto-conical surface 234 that runs to the base or bottom surface 227. The cylindrical surface 230 is sized and shaped to be received by the inner cylindrical surface 212 of the outer fastener 19. The v-thread 232 is sized and shaped to be received by and mated with the inner thread 210 of the fastener 19 in a nested, coaxial relationship. The frusto-conical surface 234 is sized and shaped to clear the insert 14 arms 160 and exclusively press upon the rod 21 as shown, for example, in FIG. 29.

As illustrated, for example, in FIGS. 16, 17, 19 and 20, the set screw 20 includes a central aperture or internal drive feature 240 formed in the top 226 and sized and shaped for a positive, non-slip engagement by a set screw installment and removal tool (not shown) that may be inserted through the bore 204 of the fastener 19 and then into the drive aperture 240. The drive aperture 240 is a poly drive, specifically, having a hexa-lobular geometry formed by a substantially cylindrical wall 242 communicating with equally spaced radially outwardly extending (from the closure central axis) rounded cut-outs or lobes 244. The wall 142 and the lobes 144 terminate at a substantially planar driving tool seating surface 246. Although the hexa-lobular drive feature 240 is preferred for torque sensitive applications as the lobes are able to receive increased torque transfer as compared to other drive systems, it is noted that other drive systems may be used, for example, a simple hex drive, star-shaped drive or other internal drives such as slotted, tri-wing, spanner, two or more apertures of various shapes, and the like. With reference to FIG. 20, the central set screw aperture 240 cooperates with the central internal bore 204 of the fastener 19 for accessing and uploading the set screw 20 into the fastener 19 prior to engagement with the bone screw receiver 10. After the closure structure 19 is inserted and rotated into the flange form 72 of the bone screw receiver 10, the set screw 20 is rotated by a tool engaging the drive feature 240 to place the set screw bottom 227 into frictional engagement with the rod 21 or other longitudinal connecting member. Such frictional engagement is therefore readily controllable by a surgeon so that the rod 21 may be readily be loosened and manipulated until late in the surgery, if desired. Thus, at any desired time, the set screw 20 may be rotated to drive the screw 20 into fixed frictional engagement with the rod 21 without varying the angular relationship between the receiver 10 and the bone screw shank 4.

It is foreseen that the set screw 20 may further include a cannulation through bore extending along a central axis thereof for providing a passage through the closure 18 interior for a length of wire (not shown) inserted therein to provide a guide for insertion of the closure top into the receiver arms 60. The base or bottom 227 of the screw 20 may further include a rim for engagement and penetration into the surface 22 of the rod 21 in certain embodiments of the invention.

Figure 22:
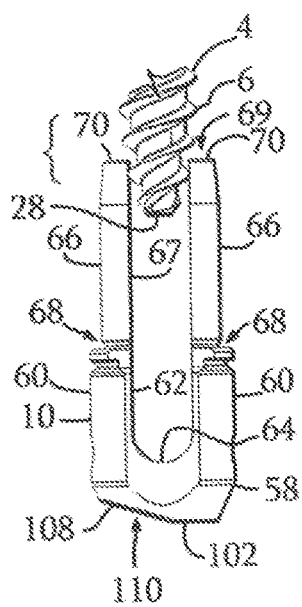
FIG. 22 is a reduced front elevational view of the receiver and shank of FIG. 1 shown in an early stage of assembly.
Figure 23:
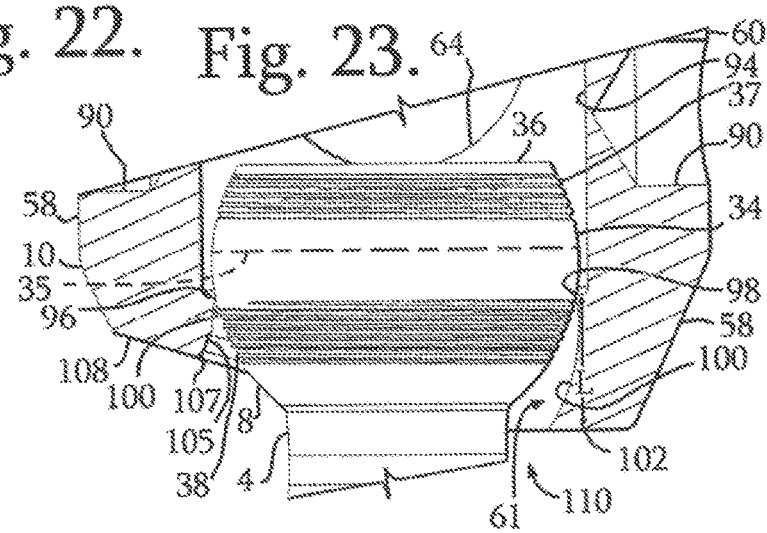
FIG. 23 is an enlarged and partial front elevational view with portions broken away of the receiver showing the shank in a stage of assembly with the receiver subsequent to what is shown in FIG. 22.

The receiver 10, the shank 4 and the compression insert 14 are typically assembled at a factory setting that includes tooling for holding, alignment and manipulation of the component pieces, as well as crimping a portion of the receiver 10 toward and against the insert 14. Pre-assembly of the receiver 10 and the shank 4 is shown in FIGS. 22-24. With particular reference to FIG. 22, the shank 4 is downloaded into the receiver by initially placing the tip 28 into a position facing the break-off extension top surfaces 70 and then lowering the shank 4 into the receiver opening 69 to a location shown in FIG. 23 with the shank head 8 hemisphere 35 located above the receiver cavity circular inner edge 98 and the shank body 6 extending downwardly out of the receiver lower opening 110. The shank upper portion or head 8 is then pressed downwardly into the receiver cavity 61 with some force as the smooth surfaced isthmus 40 that includes the shank hemisphere 35 having the diameter D2 is pushed past the receiver edge 98 having the diameter S until the shank surface 34 (both smooth 40 and ridged 38 portions) is in tight engagement with the receiver inner surface 100, but still movable in relation to the receiver spherical surface 100 as shown in FIG. 24. From such movable, but tight engagement the terminology, "non-floppy" pivotable engagement arose. Thus, at this time, the shank 4 is pivotable with respect to the receiver 10 with some force. Pivoting of the shank 4 also places some of the ridged surface portion 37 into contact with the receiver inner surface 100.

Figure 25:
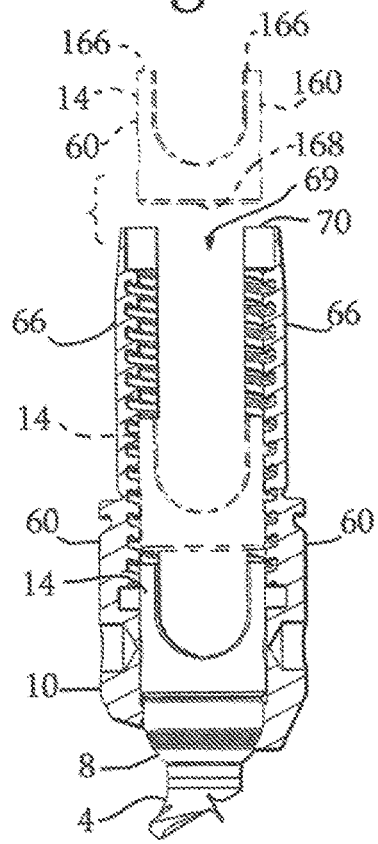
FIG. 25 is a reduced and partial front elevational view with portions broken away, further showing the insert of FIG. 1 being loaded into the assembly of FIG. 24 (intermediate loading locations shown in phantom).
Figure 26:
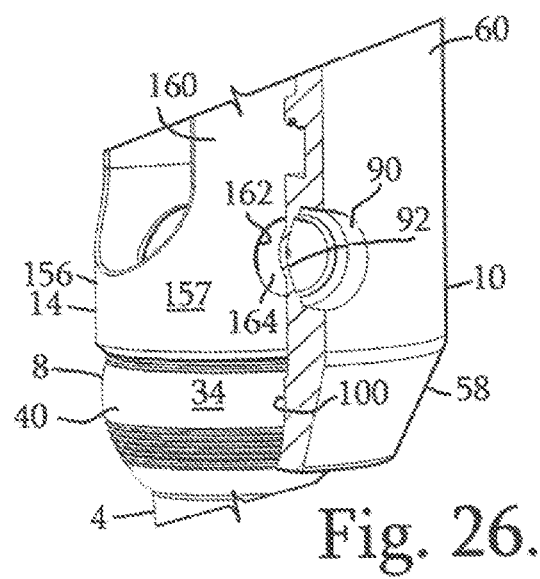
FIG. 26 is an enlarged and partial perspective view with portions broken away, showing the assembly of FIG. 25 and further showing a portion of the receiver crimped against the insert.

With reference to FIGS. 25 and 26, the compression insert 14 is then downloaded into the receiver 10 through the upper opening 169 with the insert bottom surface 168 initially facing the receiver break-off extension arm top surfaces 70 and the insert arms 160 located directly above and aligned with the extension arms 66. The insert 14 is then lowered toward the shank head 8 until the insert 14 arms 160 are adjacent the receiver arms and the insert inner surface 184 is in engagement with the shank head spherical surface 34. In some embodiments, the insert arms 160 may need to be compressed slightly during assembly to clear inner surfaces of the receiver arms 60.

With particular reference to FIG. 26, at this time, the two crimping wall portions 92 are pressed inwardly towards the insert 14 and crimping wall material thus engages the insert walls 164 defining the insert apertures 162. The crimping wall material of the wall 92 pressing against the insert 14 at two opposed locations thereby prohibits the insert 14 from rotating with respect to the receiver axis B. In the illustrated embodiment having the conical shaped recesses and crimping walls, any upward movement of the insert 14 is also prohibited by the crimping wall material of the walls 92. The resulting assembly 1 is now in a desired position for shipping.

With reference to FIG. 27, the bone screw assembly made up of the shank 4, receiver 10 and insert 14 is screwed into a bone, such as the vertebra 17, by rotation of the shank 4 using a suitable driving tool (not shown) that operably drives and rotates the shank body 6 by engagement thereof at the internal drive 50. Specifically, the vertebra 17 may be pre-drilled to minimize stressing the bone and have a guide wire (not shown) inserted therein to provide a guide for the placement and angle of the shank 4 with respect to the vertebra. A further tap hole may be made using a tap with the guide wire as a guide. Then, the bone screw assembly 1 is threaded onto the guide wire utilizing the cannulation bore 55 by first threading the wire into the opening at the shank bottom 28 and then out of the top opening at the drive feature 50. The shank 4 is then driven into the vertebra using the wire as a placement guide. It is foreseen that the shank and other bone screw assembly parts, the rod 21 (also having a central lumen in some embodiments) and the closure top 18 having the central bore can be inserted in a percutaneous or minimally invasive surgical manner, utilizing guide wires. At this time, the receiver 10 may be pivoted with respect to the implanted shank 4 using some force, the surfaces 34 with the ridges 37 and 38 in close but movable (i.e., non-floppy engagement) with the surface 100, allowing a user to manipulate the receiver 10 with some force such that once a desired angle of orientation of the receive with respect to the shank 4 is found, the receiver substantially remains in such desired position during the surgical procedure and prior to locking. With reference to FIGS. 105 and 106, for example, that show an assembly 5001 that is similar, but not identical to the assembly 1, prior to locking the insert 14 against the shank head 8, the shank 4 may be pivoted to a plurality of potentially desirable positions with respect to the receiver 10, followed by locking of the polyaxial mechanism by fully mating the multi-start closure top outer structure 19 with the receiver 10, the structure pressing down on the insert 14 that in turn presses against the shank head 8 that in turn presses against the receiver 10. Thus a variety of different angular or articulated positions of the shank 4 with respect to the receiver 10 are possible, some making full use of the sloped bottom surface 108 as shown, for example with respect to similar receivers shown in FIGS. 92 106.

With reference to FIGS. 1 and 27-29, the rod 21 is eventually positioned in an open or percutaneous manner in cooperation with the at least two bone screw assemblies 1. The closure structure 18, with the inner threaded plug 20 already threadably mated with the outer structure 19 as best shown in FIG. 28, is then inserted into and advanced between the arms 66 of the break-off extensions of each of the receivers 10. The closure structure 18 is rotated, using a tool engaged with the drive slots 216 of the outer closure structure 19 until a selected pressure is reached at which point the outer structure bottom surface 206 engages the upper arms surfaces 166 of the insert 14 and presses the insert 14 spherical surface 184 into locking engagement with the shank head outer surface 34. As was noted earlier, the two starts 203 of the flange form 202 advantageously simultaneously engage the flange form 72 on each break-off extension 66 in the early assembly stage shown in phantom in FIG. 27, providing some stability during a very difficult stage of the assembly process. Also beneficial, the two start closure 19 simultaneously engages the flange forms 72 at the weakened regions 68. As the closure structure 19 presses downwardly on the compression insert further pressing and then locking the insert spherical surface 184 against the shank spherical surface 34 and the shank spherical surface 34 against the receiver spherical surface 100, the outer structure 19 presses the rod 21 cylindrical surface 22 to a location at or near the insert saddle seat 179 as shown in FIG. 28. With reference to FIG. 29, after the rod 21 is manipulated to a desired location and orientation, the inner plug 20 is then rotated into locking engagement with the rod 21 by rotating a tool (not shown) inserted in the plug inner drive feature 240.

Figure 31:
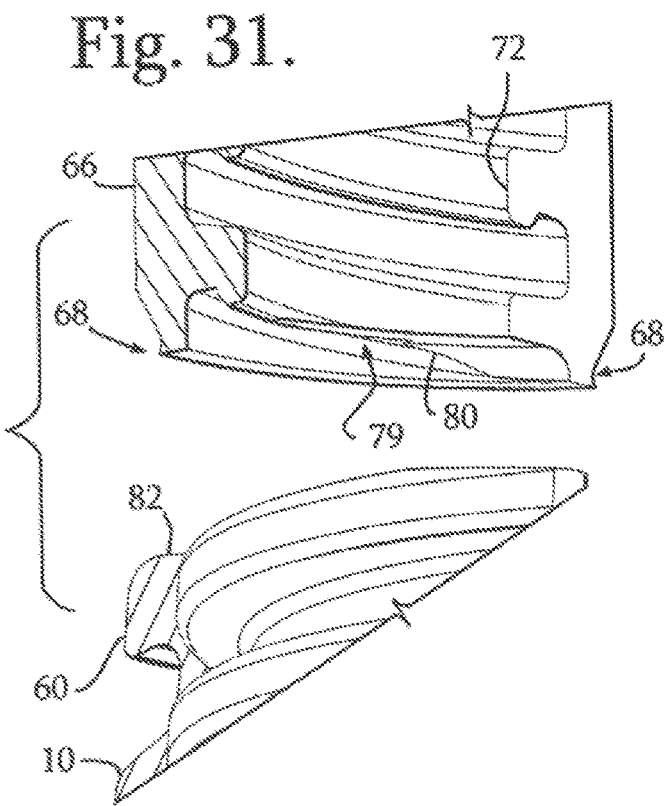
FIG. 31 is an enlarged and partial front elevational view of the assembly of FIG. 30 with portions broken away to show the detail thereof.
Figure 32:
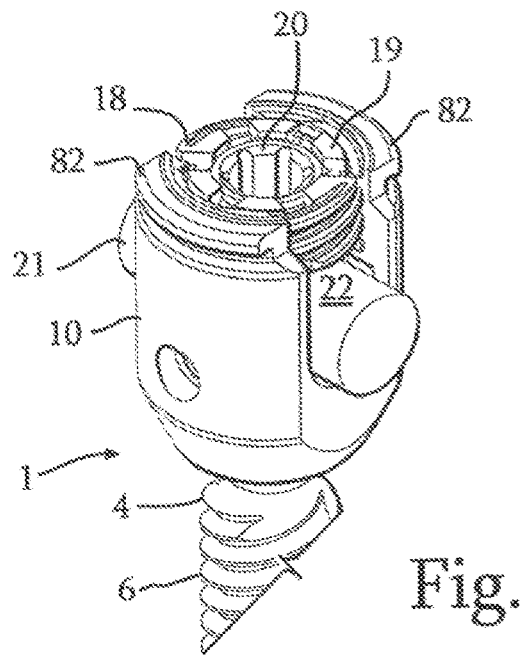
FIG. 32 is a reduced and partial perspective view of the assembly of FIG. 30 with the receiver extension tabs removed.

With reference to FIGS. 30 and 31, the break-off extensions 66 are then removed by pivoting or bending the extensions 66 back and forth at the weakened regions 68 and 79 formed by the outer groove or notch 71 and the inner recess 80. During outward and inward manipulation of the extensions 66 the receiver arms 60 are held firmly in place by the closure structure 18 already mated and in locking engagement with the receiver 10, insert 14 and the rod 21. The resulting low-profile implanted structure is shown in FIG. 32.

If removal of the rod 21 from any of the bone screw assemblies 1 is necessary, or if it is desired to release the rod 21 at a particular location, disassembly is accomplished by using the driving tool (not shown) that mates with the internal drive 240 on the closure inner plug 20. This may be all that is required to loosen and manipulate the rod 21 without unlocking the polyaxial mechanism. However, if the rod 21 is to be removed, the structure 19 may be rotated utilizing a tool engaged in the slots 216 to rotate and remove such closure structure 19 from the cooperating receiver 10. Disassembly is then accomplished in reverse order to the procedure described previously herein for the assembly. Because the surfaces 34 and 100 remain in tight physical contact, the receiver will not readily move out of a previously set angular relationship with the shank 4. However, if desired, some force may be used to adjust the angle of the receiver 10 with respect to the shank 4 at this time.

With reference to FIGS. 33-54, an alternative bone anchor embodiment or assembly 1001 is illustrated. The assembly 1001 is substantially similar to the assembly 1 with a few exceptions that include bone shank upper portion or head surface treatment, an alternative top, drop and rotate insert and a two-piece closure with break-off head. These features are described in greater detail below.

Figure 33:
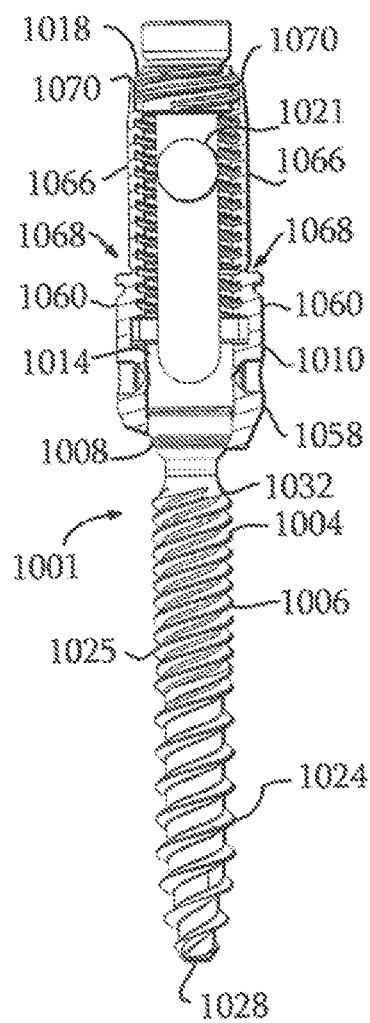
FIG. 33 is a front elevational view of an alternative polyaxial bone screw assembly, shown partially assembled with a longitudinal connecting member in the form of a rod, the assembly including a shank having an integral substantially spherical head, a receiver with break-off extensions or tabs (with portions broken away to show the detail thereof), a top, drop and rotate compression insert and a two piece dual start closure top having both an outer portion with a break-off head and an inner set screw.

With reference to FIG. 33, the open implant in the form of a polyaxial bone screw apparatus or assembly 1001 includes a shank 1004, that further includes a body 1006 integral with an upwardly extending substantially spherical upper portion or head 1008; a receiver 1010; a compression or pressure insert 1014; and a two piece multi-start closure structure or top 1018 that includes an outer structure 1019 having a double-start helically wound flange-form and a threaded inner plug 1020. Similar to what has been described above with respect to the assembly 1, the outer structure 1019 mates with the receiver 1010 and presses downwardly against the insert 1014 that in turn presses against the shank head 1008 while the inner plug 1020 ultimately presses against a longitudinal connecting member, for example, a rod 1021, so as to capture, and fix the longitudinal connecting member 1021 within the receiver 1010 and thus fix the member 1021 relative to a vertebra, such as the vertebra 17 shown with respect to the assembly 1. The receiver 1010 and shank 1004 are initially assembled and then assembled with the insert 1014 prior to implantation of the shank body 1006 into the vertebra 1017.

Figure 34:
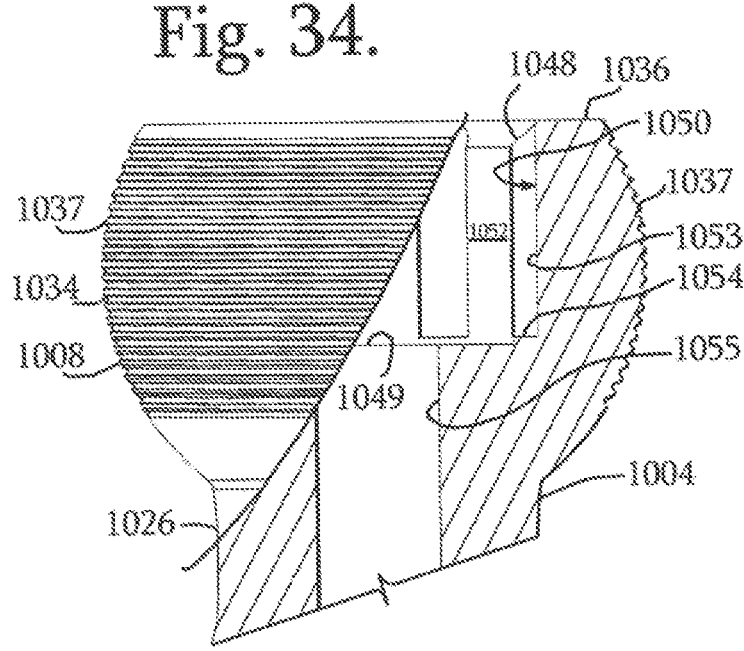
FIG. 34 is an enlarged and partial front elevational view of the shank shown in FIG. 33 with portions broken away to show the detail thereof.
Figure 35:
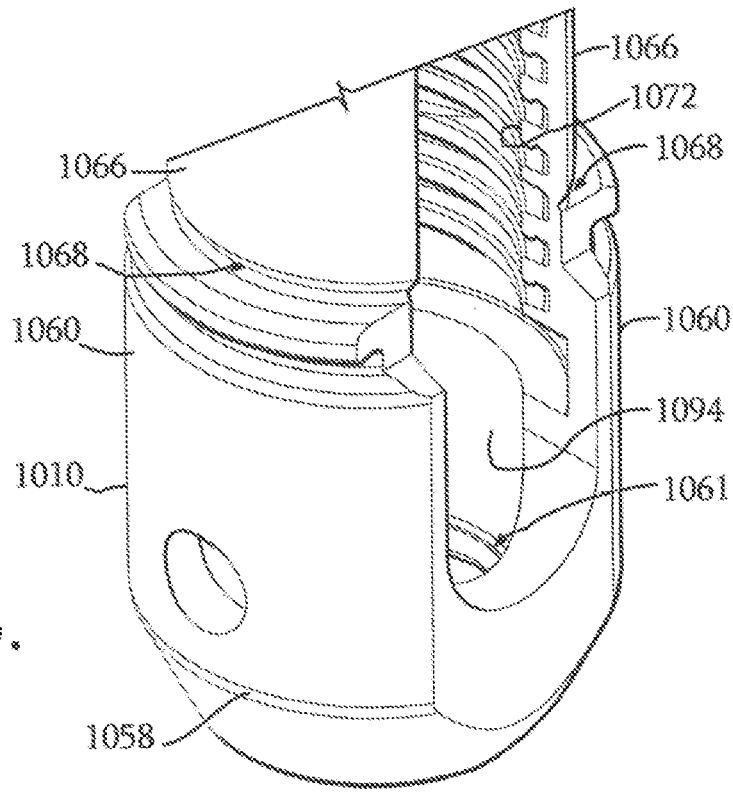
FIG. 35 is an enlarged and partial perspective view of the receiver of FIG. 33.

With particular reference to FIGS. 33 and 34, the shank 1004 is almost identical to the shank 4 previously described herein, having lower and upper thread portions 1024 and 1025, a neck 1026, a tip 1028, a shank top 1032 a shank head spherical surface 1034, upper portion or head hemisphere (not shown), a planar top 1036 and a drive 1050 with an upper frusto-conical surface 1048, a drive annular planar base 1049, a drive cylindrical wall 1052, driving lobes 1053, a drive step 1054 and a cannulation bore 1055 the same or substantially similar in form and function to the respective lower and upper thread portions 24 and 25, neck 26, tip 28, shank top 32, shank head spherical surface 34, upper portion or head hemisphere 35, planar top 36 and drive 50 with upper frusto-conical surface 48, drive annular planar base 49, drive cylindrical wall 52, driving lobes 53, drive step 54 and cannulation bore 55 of the shank 4 previously described herein with respect to the assembly 1. However, rather than having upper and lower ridged or otherwise treated surfaces on the shank head, the shank head 1008 spherical surface 10034 is substantially covered with ridges 1037 from near the top surface 1036 to near the neck 2026.

With particular reference to FIGS. 33 and 35-37, the receiver 1010 is substantially similar in form and function to the receiver 10 previously described herein with respect to the assembly 1 with the exception of some inner geometry that differs from the receiver 10, the inner geometry being sized and shaped for receiving the insert 1014 that includes outer arm extension or wings as described more fully below. Thus, the receiver 1010 includes a base 1058 and integral arms 1060, a base cavity 1061, arm extensions 1066, inner flange forms 1072 extending along each arm 1060 and arm extension 1066, a weakened region 1068 on each arm that includes an outer notch or v-cut 1071 and an inner recess 1080, extension top surfaces 1070, crimp recesses 1090 and crimping walls 1092 that are the same or substantially similar in form and function to the receiver 10 respective base 58, integral arms 60, base cavity 61, arm extensions 66, inner flange forms 72 extending along each arm 60 and arm extension 66, the weakened region 68 on each arm that includes the outer notch or v-cut 71 and the inner recess 80, extension top surfaces 70, crimp recesses 90 and crimping walls 92, as well as many other features shown in the receiver 10 and previously described herein.

Figure 36:
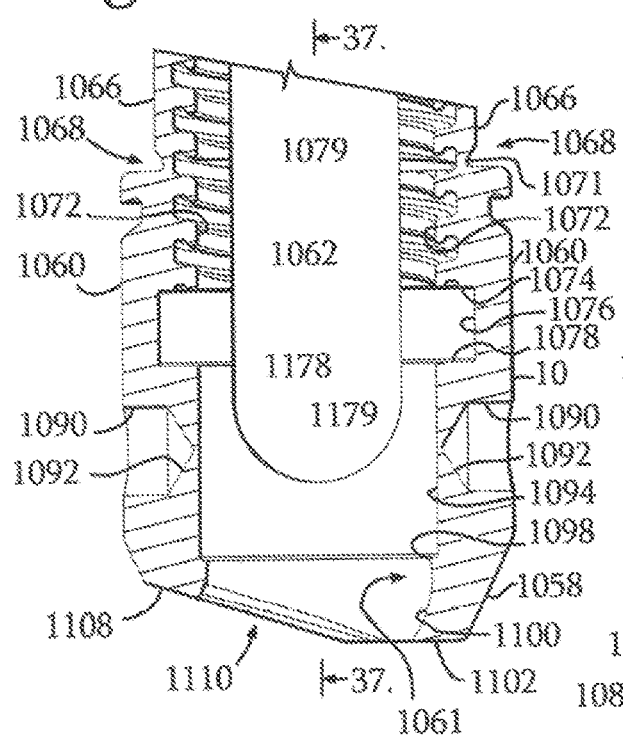
FIG. 36 is a front elevational view of the receiver of FIG. 35 with portions broken away to show the detail thereof.
Figure 38:
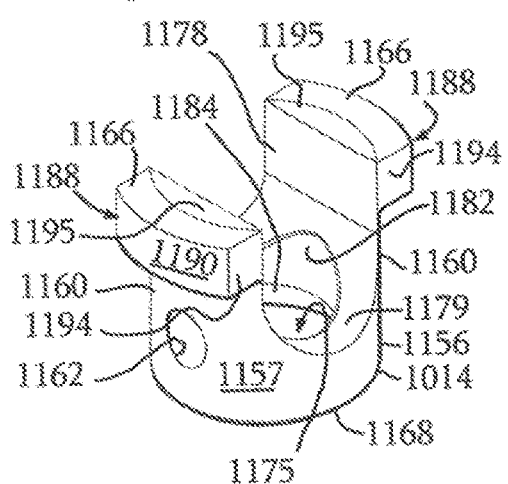
FIG. 38 is an enlarged perspective view of the compression insert of FIG. 33.
Figure 37:
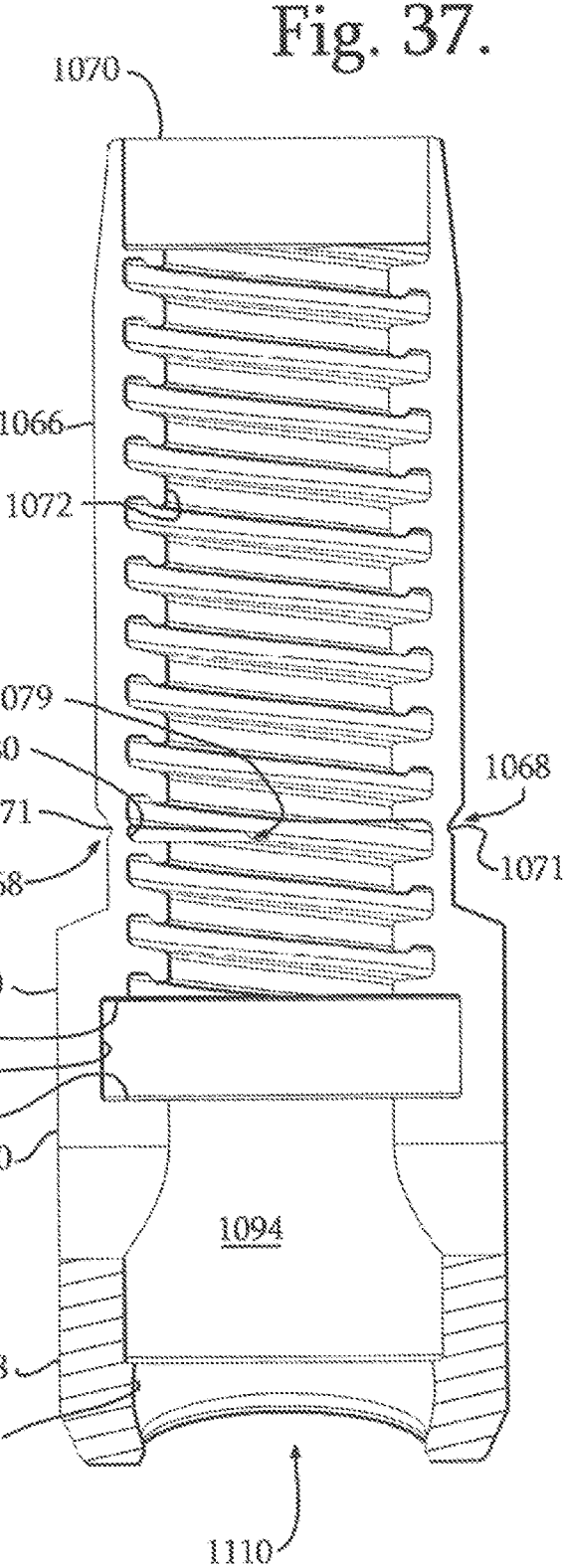
FIG. 37 is an enlarged cross-sectional view taken along the line 37-37 of FIG. 36.
Figure 47:
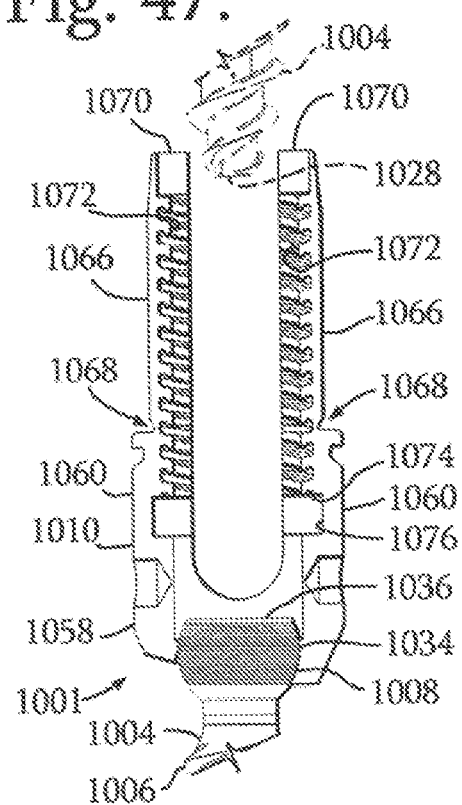
FIG. 47 is a reduced front elevational view with portions broken away of the receiver and shank of FIG. 33 shown in a stage of assembly (an earlier stage of assembly shown in phantom).

With respect to inner surfaces of the receiver 1010, shown for example, in FIGS. 36 and 37, an annular run out surface 1074 and inner cylindrical surface 1076 and an annular surface or ledge 1078 form a run-out area and receiving area for the insert 1014. The surfaces 1074, 1076 and 1078 are similar in form to the surfaces 74, 76 and 78 of the receiver 10, but they function in a different manner and encompass a larger inner area of the receiver 1010 with the surface 1076 being taller than the surface 76.

With respect to the base cavity 1061, the receiver 1010 includes a cylindrical surface 1094, a circular spheric edge 1098, an inner spherical surface 1100 and other cavity 1061 features that are identical or substantially similar to the cylindrical surface 94, circular spheric edge 98, inner spherical surface 100 and other features of the base cavity 61 previously described herein with respect to the assembly 1. The receiver 1010 further includes planar bottom surfaces 1102 and 1108 and other features defining a lower opening 1110 that are the same or substantially similar in form and function to the surfaces 102 and 108 and other features defining the lower opening 110 of the receiver 10 previously described herein.

With reference to FIGS. 38-42, the insert 1014 is substantially similar to the insert 14 in form and function with the exception of outer extensions or wings located on each arm that provide greater surface area for contact with the closure outer portion 19. Thus, the insert 1014 otherwise includes an insert body 1156, an outer substantially cylindrical surface 1157, opposed upstanding arms 1160 each with a crimp aperture 1162 having a substantially conical wall 1164, arm top surfaces 1166, a bottom annular planar rim surface 1168 terminating at a frusto-conical chamfer 1170, a through bore 1175, a saddle 1178 a lower saddle seat 1179, an inner cylindrical surface 1182 and a lower curved or radiused surface portion 1184 the same or substantially similar to the respective body 156, outer substantially cylindrical surface 157, opposed upstanding arms 160 each with crimp apertures 162 having substantially conical walls 164, arm top surfaces 166, the bottom annular planar rim surface 168 terminating at the frusto-conical chamfer 170, the through bore 175, saddle 178, lower saddle seat 179, inner cylindrical surface 182 and lower curved or radiused surface portion 184 of the insert 14 previously discussed herein. Furthermore, the insert 1014 includes a pair of opposed extensions or wings, generally, 1188 that are integral with and extend outwardly from each arm 1160. Each wing 1188 is partially defined by the respective arm top surface 1166 that extends outwardly and away from the cylindrical surface 1157, terminating at a substantially cylindrical outer surface 1190. Each cylindrical surface 1190 is adjacent to a substantially planar lower or bottom wing surface 1192 that extends substantially from the cylindrical surface 1157 to the cylindrical surface 1190. One or more curved surfaces may form a transition between the cylindrical arm surface 1157 and the planar bottom surface 1192. Each arm top surface 1166 and wing bottom surface 1192 are substantially parallel and evenly spaced and the cylindrical surface 1190 is substantially perpendicular to both the top surface 1166 and the wing bottom surface 1192. Each wing 1188 is sized and shaped to be closely received within the run-out area of the receiver 1010 defined by the surfaces 1074, 1076 and 1078. As will be discussed in greater detail below, during assembly, the insert 1014 is rotated into place within the receiver 1010 with the cylindrical surface 1190 closely received by the receiver cylindrical surface 1076. Each wing 1188 further includes opposed substantially planar front and back surfaces 1194 and a slightly downwardly and inwardly sloping upper surface 1195 that spans between each top surface 1166 and the respective inner saddle surface 1178. The illustrated surface 1195 slopes downwardly at about a two degree angle with respect to the surface 1166. The surface 1195 is sized and shaped for frictionally engaging the closure 1018 outer structure 1019.

With reference to FIGS. 43-46, the two-piece closure 1018 is shown having an outer structure 1019 and an inner plug 1029 that is substantially similar to the closure 18 previously described herein having the outer structure 19 and inner plug 20. However, the closure 1018 outer structure 1019 further includes a break-off head 1201 designed to twist off and break away from the structure 1019 once a desired torque is reached (for example, 70 to 140 inch pounds) when the structure 1019 is rotated within the receiver 1010 and tightened into locking frictional engagement with the insert 1014. Thus, because of the break-off head 1201, a drive feature 1216 of the outer closure structure 1019 differs from the slotted drive feature 216 of the closure structure 19 previously described herein. As will be described in greater detail below, the drive feature 1216 is similar to the multi-lobular drive feature of the insert plug or set screw 1020 (that is similar to the set screw 20 previously described herein), but the lobes are in a position slightly advanced or rotated with respect to the lobes of the screw 1020 (when the screw 1020 is fully received within the closure 1019 and cannot be rotated upwardly any further as shown in FIG. 44) so that a user cannot access the inner plug driving lobes until the break-off head 1201 is removed.

As stated above, the closure 1018 includes two pieces: the outer structure or fastener 1019 having an outer guide and advancement structure in the form of a double-start helically wound splay control flange form and an inner thread sized and shaped for cooperation with the coaxial threaded inner plug 1020, the helically wound forms of both of the structures 1018 and 1019 being coaxial and having a central axis of rotation that is the same as the central axis of the receiver 1010 when assembled with the receiver 10. The outer structure 1019 of the closure top 1018 mates under rotation with the receiver 1010, the structure 1019 pressing downwardly against the insert 1014 arm top surfaces 1166, the insert surface 1184 in turn pressing downwardly against the shank head 1008 that in turn frictionally engages the receiver 1010, locking the polyaxial mechanism of the bone anchor 1001, (i.e., fixing the shank 1004 at a particular angle with respect to the receiver 1010). The closure inner plug 1020 ultimately frictionally engages and presses against the longitudinal connecting member, for example, the rod 1021, so as to capture, and fix the longitudinal connecting member 1021 within the receiver 1010 and thus fix the member 1021 relative to the vertebra 17.

The multi-start closure 1018 outer splay control structure 1019 has a double or dual start helically wound guide and advancement structure in the form of a pair of identical helically wound forms 1202, each illustrated as a flange form that operably joins with mating flange form structures 1072 disposed on the arms 1060 and break-off extensions 1066 of the receiver 1010 to result in an interlocking guide and advancement structure or arrangement as described above with respect to the receiver 10 and the closure 18. Each form 1202 includes a start surface or structure 1203 and thus, as shown in FIG. 46, the structure 19 includes two starts 1203. The closure and receiver flanges 1202 and 1072 have respective splay regulating contours to control splay of the receiver arms 1060 when the inner member 1019 is strongly torqued therein.

With particular reference to FIGS. 43 and 44, the illustrated fastener structure 1019 includes a through-bore 1204 extending along the central axis and running completely through the fastener structure 1019 from a planar and substantially annular top surface 1205 of the break-off head 1201 to a bottom surface 1206 of the fastener 1019. The break-off head 1201 is substantially cylindrical in outer contour from the top surface 1205 to a weakened region, generally 1027. The illustrated break-off head 1201 is integral with the closure outer structure 1019 at the weakened region 1207 that is also located near a top substantially annular and planar surface 1208 of the structure 1019, the weakened region 1207 being primarily defined by a notch or groove 1209 cut into the cylindrical surface of the break-off head 1201.

The closure structure 1019 bottom surface 1206 is substantially planar and annular and configured for being received between the receiver arms 1060 and for exclusively abutting against the substantially planar top surfaces 1166 of the insert arms 1160. The insert 1014 arms 1160 are configured to extend above the rod 1021 such that the closure surface 1206 is always spaced from the rod 1021 or other longitudinal connecting member portion received by the insert arms 1160 and located within the receiver 1010. When the closure structure 1019 is rotated into the receiver 1010 between receiver arms 1060, each having the flange form 1072 guide and advancement structure, the start 1203 engages mating guide and advancement structure 1072 on one arm break-off extension 1066 and the opposite start 1203 simultaneously engages the guide and advancement structure flange form 1072 on the opposing arm extension 1066, both forms 1202 being simultaneously captured by the mating forms 1072 on the opposed arm extensions 1066. As the structure 1019 is rotated, the structure advances axially downwardly between the break-off extensions 1066 and then the arms 1060 and then presses evenly down upon the insert 1014 arm top surfaces 1166.

At the closure structure base or bottom surface 1206 and running to near the top surface 1208, the bore 1204 is substantially defined by a guide and advancement structure shown in the drawing figures as an internal V-shaped thread 1210. The thread 1210 is sized and shaped to receive the threaded set screw 1020 therein as will be discussed in more detail below. Although a traditional V-shaped thread 1210 is shown, it is foreseen that other types of helical guide and advancement structures may be used. Adjacent the closure top surface 1208, the bore 1204 is defined by a cylindrical surface 1212 that runs from the v-thread 1210, past the surface 1208 and joins with an upwardly and inwardly directed frusto-conical surface 2013 located on the break-off head 1201. The cylindrical surface 1212 has a radius measured from the closure central axis that is the same or substantially similar to a radius from the central axis to a crest 1214 of the v-thread 1210. In the illustrated embodiment, when the break-off head 1201 is removed, a distance from the top surface 1208 to the v-thread 1210 measured along the surface 1212 is greater than a pitch of the v-thread 1210, the surface 1212 acting as a stop for the inner set screw or plug 1020, preventing the screw 1020 from rotating upwardly and out of the structure 1019 at the top surface 1205.

The frusto-conical surface 1213 extends between the cylindrical surface 1212 and an upper multi-lobular drive feature, generally 1215, of the break-off head 1201. With particular reference to FIG. 44, the drive feature 1215 is formed in the top surface 1206 and sized and shaped for a positive, non-slip engagement by a closure installment and removal tool (not shown) that may be inserted through the bore 1204 of the fastener 1019 and then into the drive aperture 1215. The drive aperture 1215 is a poly drive, specifically, having a hexa-lobular geometry formed by a substantially cylindrical wall 1216 communicating with equally spaced radially outwardly extending (from the closure central axis) rounded cut-outs or lobes 1217 (see FIGS. 44 and 45). The wall 1216 and the lobes 1217 terminate at the frusto-conical surface 1213. The hexa-lobular drive feature 1215 is preferred for torque sensitive applications as the lobes are able to receive increased torque transfer as compared to other drive systems. However, it is noted that other drive systems may be used for a closure inner drive, for example, a simple hex drive, star-shaped drive or other internal drives such as slotted, tri-wing, spanner, two or more apertures of various shapes, and the like.

With reference to FIGS. 43 and 44, the up-loadable set screw 1020 has a substantially annular and planar top 1226 and a substantially circular planar bottom 1227. The screw 1020 is substantially cylindrical in shape and coaxial with the outer fastener 1019. The screw 1020 includes an upper outer cylindrical surface 1230 adjacent a v-thread surface portion 1232 that in turn is adjacent to a lower frusto-conical surface 1234 that runs to the base or bottom surface 1227. The cylindrical surface 1230 is sized and shaped to be received by the inner cylindrical surface 1212 of the outer fastener 1019. The v-thread 1232 is sized and shaped to be received by and mated with the inner thread 1210 of the fastener 1019 in a nested, coaxial relationship. The frusto-conical surface 1234 is sized and shaped to clear the insert 1014 arms 1160 and exclusively press upon the rod 1021 as shown, for example, in FIG. 53.

As illustrated, for example, in FIGS. 44 and 45, the set screw 1020 includes a central aperture or internal drive feature, generally 1240, formed in the top 1226 and sized and shaped for a positive, non-slip engagement by a set screw installment and removal tool (not shown) that may be inserted into the drive aperture 1240 after the break-off head 1201 is removed. The drive aperture 1240 is a poly drive, specifically, having a hexa-lobular geometry formed by a substantially cylindrical wall 1242 communicating with equally spaced radially outwardly extending (from the closure central axis) rounded cut-outs or lobes 1244. The wall 1242 and the lobes 2144 terminate at a substantially planar driving tool seating surface 1246. Although the hexa-lobular drive feature 1240 is preferred for torque sensitive applications as the lobes are able to receive increased torque transfer as compared to other drive systems, it is noted that other drive systems may be used, for example, a simple hex drive, star-shaped drive or other internal drives such as slotted, tri-wing, spanner, two or more apertures of various shapes, and the like. With reference to FIGS. 43 and 44, the plug or set screw 1020 is inserted into the central internal bore 1204 of the fastener 1019 and rotated to upload the set screw 1020 into the fastener 1019 prior to assembly of the two-piece closure 1018 with the bone screw receiver 1010. As indicated above, the two drives 1215 and 1240 are preferably aligned as shown in FIG. 45 during assembly with the receiver 1010 such that the lobes 1217 of the drive 1215 of the outer fastener 1019 are not in alignment with the lobes 1244 of the set screw drive 1240. When in such position, the set screw bottom surface 1227 is desirably located within the outer closure structure 1019 such that the outer structure bottom surface 1206 is the only surface that initially bears down on the rod, but that allows the rod clearance and freedom of movement within the receiver when the bottom surface 1206 engages the insert arm top surfaces 1166. Thus, when the outer fastener 1019 is rotated into the receiver 1010 break-off extensions 1066 and receiver arms 1060, the driving tool is not engaged with the set screw drive 1240 so that at a preferred torque, the break-off head 1201 will twist off of the closure 1018 and then removed with the driving tool. It is foreseen that in other embodiments of the invention, the outer closure structure 1019 drive feature and the inner plug or set screw 1020 drive feature may be of different geometries to ensure that a driving tool does not engage the inner set screw until the break-off head is removed. In the illustrated closure 1018, however, if desired, a user could align the lobes 1217 with the lobes 1244, if desired, in order to rotate both parts of the closure 1018 at the same time.

In the illustrated embodiment, after the closure structure 1019 is inserted and rotated into the flange form 1072 of the bone screw receiver 1010 and the break-off head 1201 has twisted off and removed, the set screw 1020 is rotated by a tool engaging the drive feature 1240 to place the set screw bottom 1227 into frictional engagement with the rod 1021 or other longitudinal connecting member. Such frictional engagement is therefore readily controllable by a surgeon so that the rod 1021 may be readily be loosened and manipulated until late in the surgery, if desired. Thus, at any desired time, the set screw 1020 may be rotated to drive the screw 1020 into fixed frictional engagement with the rod 1021 without varying the angular relationship between the receiver 1010 and the bone screw shank 1004 that is already in locked frictional engagement by pressure from the closure outer structure 1019 on the insert 1014 that presses against the bone screw shank 1008 that in turn presses against the receiver 1010.

It is foreseen that the set screw 1020 may further include a cannulation through bore extending along a central axis thereof for providing a passage through the closure 1018 interior for a length of wire (not shown) inserted therein to provide a guide for insertion of the closure top into the receiver arm extensions 1066 and then the arms 1060. The base or bottom 1227 of the screw 1020 may further include a rim for engagement and penetration into the surface 1022 of the rod 1021 in certain embodiments of the invention.

The receiver 1010, the shank 1004 and the compression insert 1014 are typically assembled at a factory setting that includes tooling for holding, alignment and manipulation of the component pieces, as well as crimping a portion of the receiver 1010 toward and against the insert 1014. Pre-assembly of the receiver 1010 and the shank 1004 by downloading the shank 1004 into the receiver 1010 is shown, for example, in FIG. 47 and is accomplished in a manner identical to that previously described herein with respect to the shank 4 and receiver 10 and shown in FIGS. 22-24.

Figure 48:
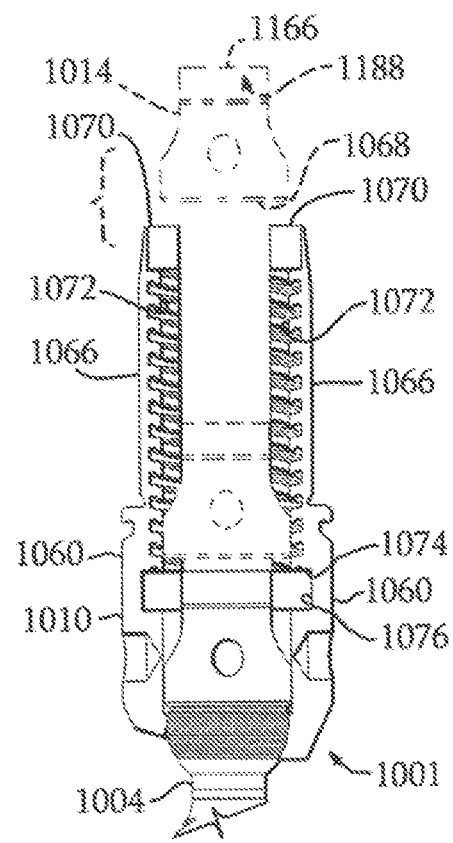
FIG. 48 is a front elevational view with portions broken away, further showing the insert of FIG. 33 being down loaded into the assembly of FIG. 47 (intermediate loading locations shown in phantom).
Figure 49:
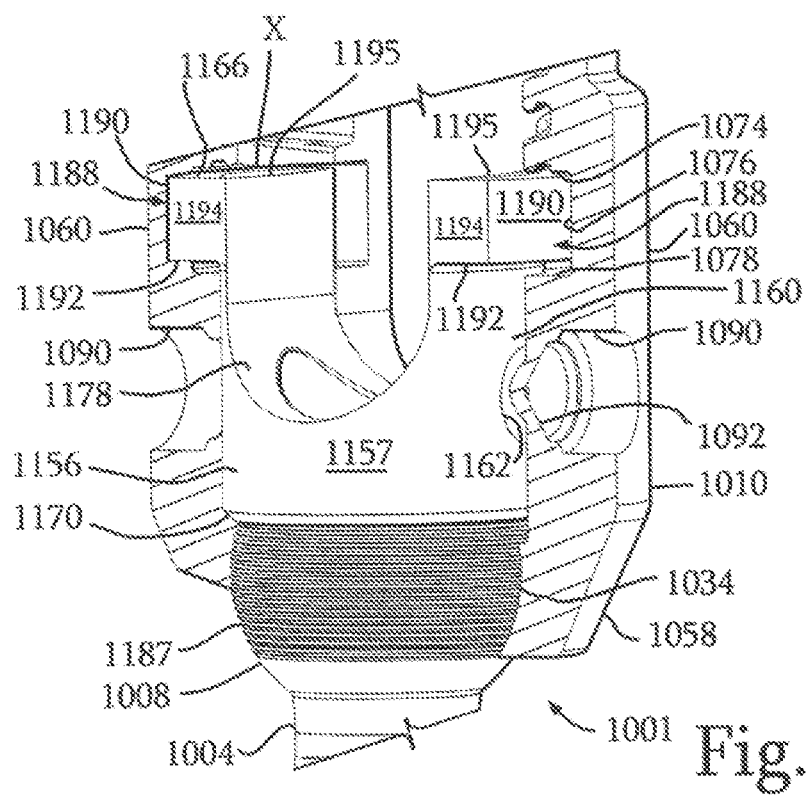
FIG. 49 is an enlarged and partial perspective view with portions broken away, showing the assembly of FIG. 48 after rotation of the insert into an operative position and further showing a portion of the receiver crimped against the insert.
Figure 50:
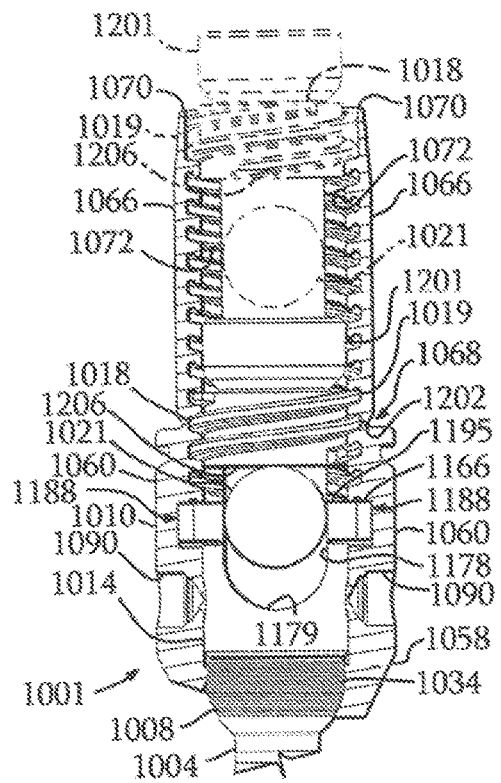
FIG. 50 is a reduced and partial front elevational view of the of assembly as shown in FIG. 49 with portions broken away to show the detail thereof, further showing the rod and closure top of FIG. 33, also in front elevation, in a stage wherein the closure top is being wound downwardly in mating relationship with the receiver extension tabs and reducing the rod into the receiver, an earlier stage of loading of the rod and closure top shown in phantom.
Figure 51:
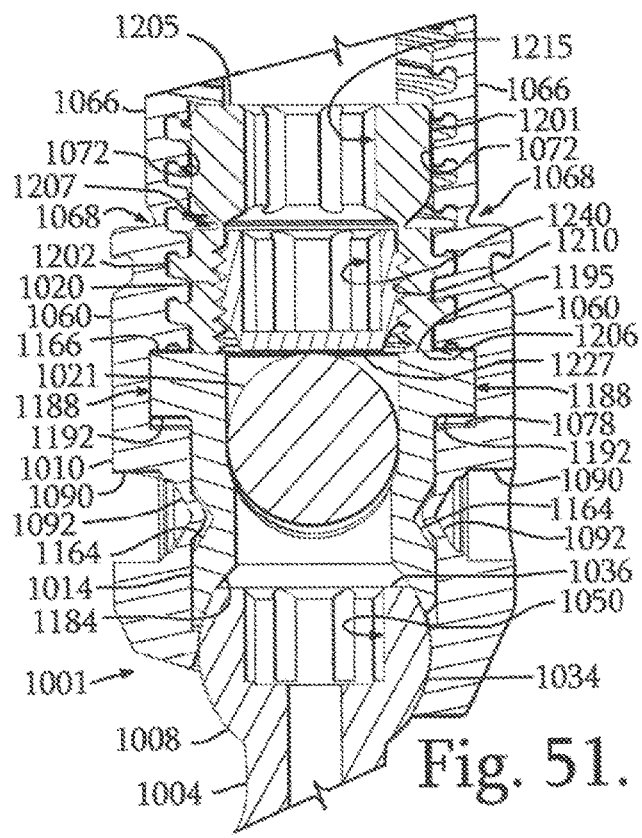
FIG. 51 is an enlarged and partial front elevational view with portions broken away, similar to FIG. 50, showing the outer portion of the closure top pressing the insert downwardly into locking relationship with the shank head.

With reference to FIGS. 48 and 49, the compression insert 1014 is then downloaded into the receiver 1010 through the receiver upper opening with the insert bottom surface 1168 initially facing the receiver break-off extension arm top surfaces 1070 and the insert arms 1160 located above and between the extension arms 1066 as shown in phantom in FIG. 48. The insert 1014 is then lowered toward the shank head 1008 until the insert 1014 arms 1160 are located below the receiver annular surface 1074. At that time, the insert 1014 is rotated about the receiver central axis either clockwise or counter-clockwise until the insert arms 1160 are adjacent the receiver arms and the insert wings 1188 are located directly beneath each of the surfaces 1074 with the wing outer surfaces 1190 being closely received and adjacent to the receiver inner cylindrical surfaces 1076. In some embodiments, the insert arms 1160 may need to be compressed slightly during assembly to clear all of the inner surfaces of the receiver arms 1060.

With particular reference to FIG. 49, at this time, the two crimping wall portions 1092 are pressed inwardly towards the insert 1014 and crimping wall material thus engages the insert walls 1164 defining the insert apertures 1162. The crimping wall material of the wall 1092 pressing against the insert 1014 at two opposed locations thereby prohibits the insert 1014 from rotating with respect to the receiver central axis. In the illustrated embodiment having the conical shaped recesses and crimping walls, any upward movement of the insert 1014 is prohibited by the receiver guide and advancement structure 1072 and also by the crimping wall material of the walls 1092. The resulting assembly 1001 is now in a desired position for shipping and for implanting into a vertebra, such as the vertebra 17 as previously described herein with respect to the assembly 1. As with the assembly 1, prior to locking the insert 1014 against the shank head 1008, the shank 1004 may be pivoted (using some force to overcome the friction fit between the shank head and the receiver) to a plurality of potentially desirable positions with respect to the receiver 1010, followed by locking of the polyaxial mechanism by mating and rotating the multi-start closure top outer structure 1019 with respect to the receiver 1010, the structure 1019 pressing down on the insert 1014 that in turn presses against the shank head 1008 that in turn presses against the receiver 1010. Thus a variety of different angular or articulated positions of the shank 1004 with respect to the receiver 1010 are possible, some making full use of the sloped bottom surface 1108 as shown, for example in FIGS. 92 and 106.

Figure 52:
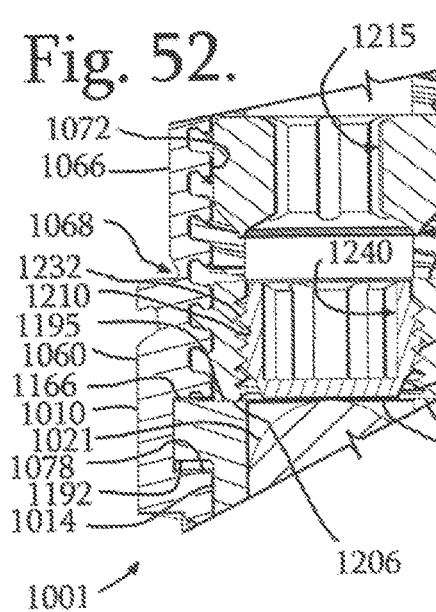
FIG. 52 is an enlarged and partial front elevational view with portions broken away, similar to FIG. 51 and further showing removal of the closure top break-off head.
Figure 53:
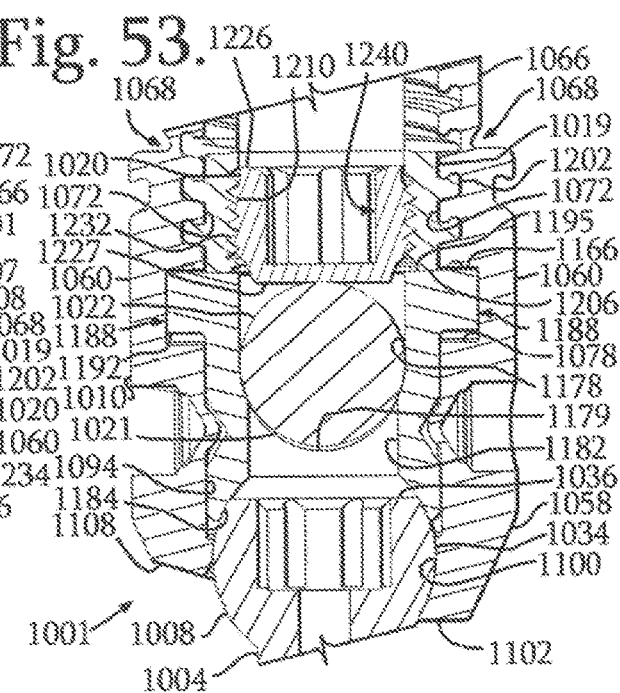
FIG. 53 is a partial front elevational view with portions broken away, similar to FIG. 52 and further showing the closure top inner set screw locking down on the rod.

With reference to FIGS. 50-53, the rod 2021 is eventually positioned in an open or percutaneous manner in cooperation with the at least two bone screw assemblies 1001 (or 1). The closure structure 1018, with the inner threaded plug 1020 already threadably mated with the outer structure 1019 as shown, for example, in FIG. 44, is then inserted into and advanced between the arms 1066 of the break-off extensions of each of the receivers 1010. The closure structure 1018 is rotated, using a tool engaged with the break-off head drive feature 1215 of the outer closure structure 1019 until a selected pressure is reached at which point the outer structure bottom surface 1206 engages the insert 1014 arm tops 1166 substantially at the inwardly and slightly downwardly sloping surfaces 1195 and presses the insert 1014 spherical surface 1184 into locking frictional engagement with the shank head outer surface 1034. The two starts 1203 of the flange form 1202 advantageously simultaneously engage the flange form 1072 on each break-off extension 1066 in the early assembly stage shown in phantom in FIG. 50, providing some stability during a very difficult stage of the assembly process. Also beneficial, the two start closure 1019 simultaneously engages the flange forms 1072 at the weakened regions 1068. As the closure structure 1019 presses downwardly on the compression insert further pressing and then locking the insert spherical surface 1184 against the shank spherical surface 1034 and the shank spherical surface 1034 against the receiver spherical surface 1100, the outer structure 1019 presses the rod 1021 cylindrical surface 1022 to a location at or near the insert saddle seat 1179. As shown in FIG. 52, at such time the break-off head 1201 twists off of the fastener 1019 at the weakened region 1207 and is then removed from the receiver arm extensions 1066 and out the top of the channel partially defined by the guide and advancement structure 1072. With reference to FIG. 53, after the rod 21 is manipulated to a desired location and orientation, the inner plug 1020 is then rotated into locking frictional engagement with the rod 1021 by rotating the driving tool (not shown) inserted in the plug inner drive feature 1240.

Figure 54:
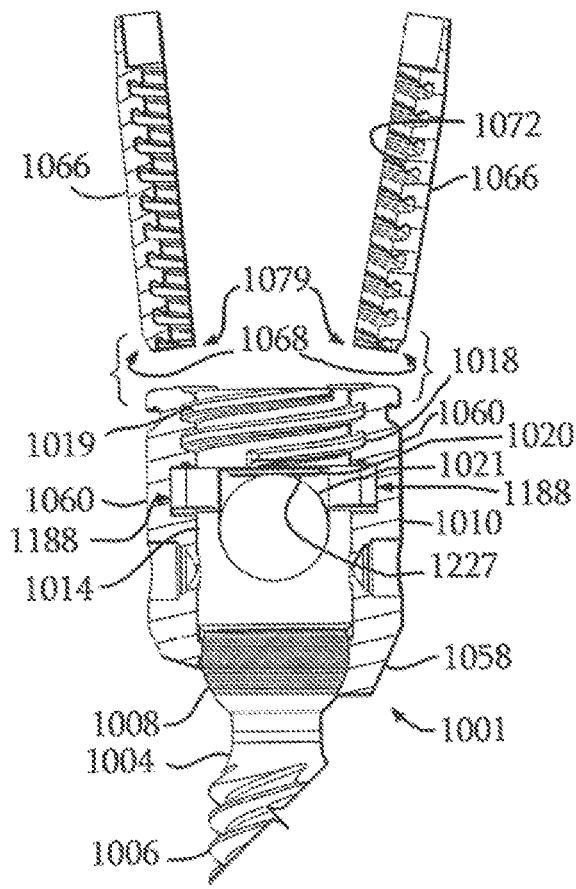
FIG. 54 is a reduced and partial front elevational view with portions broken away, similar to FIG. 53 further showing removal of the receiver extension tabs.

With reference to FIG. 54, the break-off extensions 1066 are then removed by pivoting or bending the extensions 1066 back and forth at the weakened regions 1068 and 1079 formed by the respective outer groove or notch 1071 and inner recess 1080. During outward and inward manipulation of the extensions 1066, the receiver arms 1060 are held firmly in place by the closure structure 1018 already mated and in locking engagement with the receiver 1010, insert 1014 and the rod 1021. The resulting low-profile implanted structure is also shown in FIG. 54.

If removal of the rod 1021 from any of the bone screw assemblies 1 or 1001 is necessary, or if it is desired to release the rod 1021 at a particular location, disassembly is accomplished by using the driving tool (not shown) that mates with the internal drive 1240 on the closure inner plug 1020. This may be all that is required to loosen and manipulate the rod 21 without unlocking the polyaxial mechanism. However, if the rod 1021 is to be removed, the inner plug 1020 and attached outer structure 1019 may be rotated by continued rotation of the driving tool mated with the internal drive 1240. Disassembly is then accomplished in reverse order to the procedure described previously herein for assembly. Because the surfaces 1034 and 1100 remain in tight physical contact, the receiver will not readily move out of a previously set angular relationship with the shank 1004. However, if desired, some force may be used to adjust the angle of the receiver 1010 with respect to the shank 1004 at this time.

With reference to FIGS. 55-67, an alternative cam surface insert 1014' is illustrated that is assembled with the shank 1004 and a receiver 1010' in lieu of the insert 1014, resulting in an alternative bone anchor embodiment or assembly 1001'. The receiver 1010' is identical to the receiver 1010 previously described herein with the exception of a slight adjustment to the position of the flange forms on the receiver and break-off extension arms to provide clearance for portions of the insert 1014' as will be described in greater detail below. Thus, the receiver 1010' will not be described in detail herein and all of the numbered features for the receiver 1010' are the same in form and function as the numbered features of the receiver 1010, but are referenced with an added "'" at the end of each number to make clear that the insert 1010' is slightly different from the insert 1010.

Thus, the assembly 1001' is substantially similar to the assembly 1001 previously described herein with the exception of the alternative insert 1014'. Only the insert 1014' and the cooperation of the insert 1014' with the shank 1004, receiver 1010' and closure 1018 will be described with respect to FIGS. 55-67 as all other features have been discussed in the previously described assemblies 1 and 1001. Upper sloping or "camming" surfaces of the insert 1014' advantageously cooperate with the receiver closure run-out surfaces 1074' to aid in the top, drop and rotate loading of insert 1014' with respect to the receiver 1010'. As will be described in greater detail below, when the insert 1014' is rotated into a desired operational position, the closure run-out surfaces 1074' function as a block to any further rotation of the insert 1014', the insert being placed in a desired position with each insert arm aligned centrally with the adjacent receiver arm. Although the illustrated embodiment also includes crimping walls that aid in centering and alignment of the insert as previously discussed with regard to the assemblies 1 and 1001, in certain situations, crimping walls alone may or may not withstand the extreme torque placed on an insert during tightening of a closure top, causing the insert to rotate out of the desired centered position. The ramped or camming surfaces of the illustrated insert 1014' are designed to abut against the receiver 1010' run-out surfaces so that the receiver run-out surfaces act as an abutment to any further rotation in the direction of rotation. Thus, eventual tightening of a closure top against top surfaces of the insert 1014' in the same rotational direction cannot rotate the insert 1014' out of the desired centered and aligned position with respect to the receiver 1010'. The crimp walls aid in keeping the insert centered when the insert is pushed in an opposite direction, such as, for example, when the closure is removed for any reason.

Furthermore, it is noted that in some embodiments of the invention, the friction fit between the shank upper portion 1008 and the receiver inner spherical surface 1100' is increased or further supported by the engagement of the camming insert 1014' with the shank head or upper portion 1008, even when a rod or closure is not yet placed in the receiver or has been removed from the receiver. In such embodiments, rotation of the insert 1014' helically sloping surfaces against the closure run-out surfaces 1074' moves the insert 1014' downwardly during rotation thereof into a friction or press fit engagement with the shank head 1008. Thus, in situations where the shank head is loose or more easily slidable with respect to the receiver when the insert 1014' is not yet loaded (either by design or because of tolerances), once the insert 1014' is rotated into place and such rotation lowers the insert into frictional contact with the shank upper portion 1008, the shank 1004 is then only pivotable with respect to the receiver 1010' in a "non-floppy" manner by using a force to move the shank upper portion with respect to the insert.

It is foreseen that in other embodiments (such as an embodiment having a uploaded shank), upper cam or ramped surfaces of the insert may be modified such that rotation of the insert with respect to a receiver presses the insert downwardly on the shank head 1008 with enough force to frictionally lock the polyaxial mechanism of the bone screw. Thus, such action frictionally locks the shank in a desired angular relationship with the receiver prior to insertion of a rod or other longitudinal connecting member, resulting in a bone screw assembly that performs like a mono-axial screw during manipulation of the individual components during surgery.

With particular reference to FIGS. 56-62, the insert 1014' is substantially similar to the insert 1014 in form and function with the exception of upper surfaces 1166' of the arms thereof that include opposed sloping or ramp surfaces 1167' formed thereon. Each of the ramped surfaces 1167' include contours complimentary to and thus closely received but cleared by adjacent receiver flange form 1072' lower surfaces that make up a lower toe or load flank thereof as shown, for example, in FIG. 65. As will be described in greater detail below, as the insert 1014' is rotated into an operating position within the receive 1010', the ramped surfaces 1167' engage the receiver surfaces 1074' and thus the insert 1014' acts as a cam, making initial sliding contact with the surface 1074' while rotating the insert and thus moving the insert 1014' downwardly in the receiver toward the receiver base 1058'. The insert ramped surfaces 1167' are sized and shaped to fully frictionally engage and be stopped from further rotation by the cooperating receiver surfaces 1074 when the insert is located at a desired central location with the insert arms aligned with the receiver arms and the receiver crimp walls being adjacent the insert crimp apertures. As stated above, the ramped surfaces 1167' may also be sized and shaped so that when the insert is stopped, it is also in a non-floppy, frictional or press fit engagement with the shank upper portion 1008 wherein the upper portion 1008 can be pivoted with respect to the insert by using some force.

The insert 1014' thus otherwise includes an insert body 1156', an outer substantially cylindrical surface 1157', opposed upstanding arms 1160' each with a crimp aperture 1162' having a substantially conical wall 1164', a bottom annular planar rim surface 1168' terminating at a frusto-conical chamfer 1170', a through bore generally 1175', a saddle 1178' a lower saddle seat 1179', an inner cylindrical surface 1182' and a lower curved or radiused surface portion 1184' the same or substantially similar to the respective body 1156, outer substantially cylindrical surface 1157, opposed upstanding arms 1160 each with crimp apertures 1162 having substantially conical walls 1164, bottom annular planar rim surface 1168 terminating at the frusto-conical chamfer 1170, the through bore 1175, saddle 1178, lower saddle seat 1179, inner cylindrical surface 1182 and lower curved or radiused surface portion 1184 of the insert 1014 previously described herein (also as previously described herein with respect to the insert 14). Furthermore, similar to the insert 1014, the insert 1014' includes a pair of opposed extensions or wings, generally, 1188', each wing 1188' partially defined by the respective arm top surface 1166'. Each wing 1188' also extends outwardly and away from the cylindrical surface 1157' and terminates at a substantially cylindrical outer surface 1190'. Each cylindrical surface 1190' is adjacent to a substantially planar lower or bottom wing surface 1192' that extends substantially from the cylindrical surface 1157' to the cylindrical surface 1190'. One or more curved surfaces may form a transition between the cylindrical arm surface 1157' and the planar bottom surface 1192'. Each wing 1188' further includes opposed substantially planar front and back surfaces 1194' and a slightly downwardly and inwardly sloping upper surface 1195' that spans between each of the top surface portions 1166' and 1167' and the respective inner saddle surface 1178'. The insert arm surfaces 1195' are sized to receive and engage the annular bottom surface of the closure structure 1019. During assembly, the insert 1014 is rotated into place within the receiver 1010' with the cylindrical surface 1190' closely received by the receiver cylindrical surface 1076' and the insert top surfaces 1166' and 1167' cooperating with and engaging the receiver surfaces 1074' while clearing the receiver flange forms 1072'.

The receiver 1010', the shank 1004 and the compression insert 1014' are typically assembled at a factory setting that includes tooling for holding, alignment and manipulation of the component pieces, as well as crimping a portion of the receiver 1010' toward and against the insert 1014'. Pre-assembly of the receiver 1010' and the shank 1004 is accomplished in a manner identical to that previously described herein with respect to the shank 4 and receiver 10 and shown in FIGS. 22-24.

Figure 55:
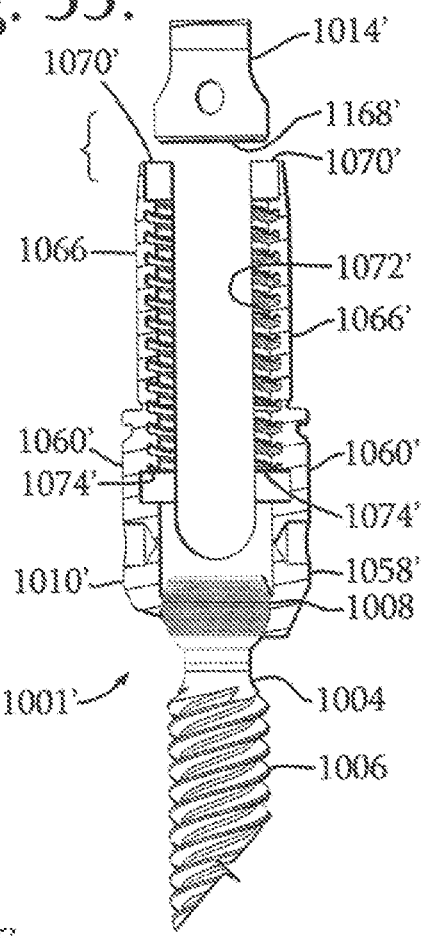
FIG. 55 is a partially exploded front elevational view of another alternative polyaxial bone screw assembly including a shank having an integral substantially spherical head, a receiver with break-off extensions or tabs (shown with portions broken away to show the detail thereof), and a compression insert with cam upper surface.
Figure 56:
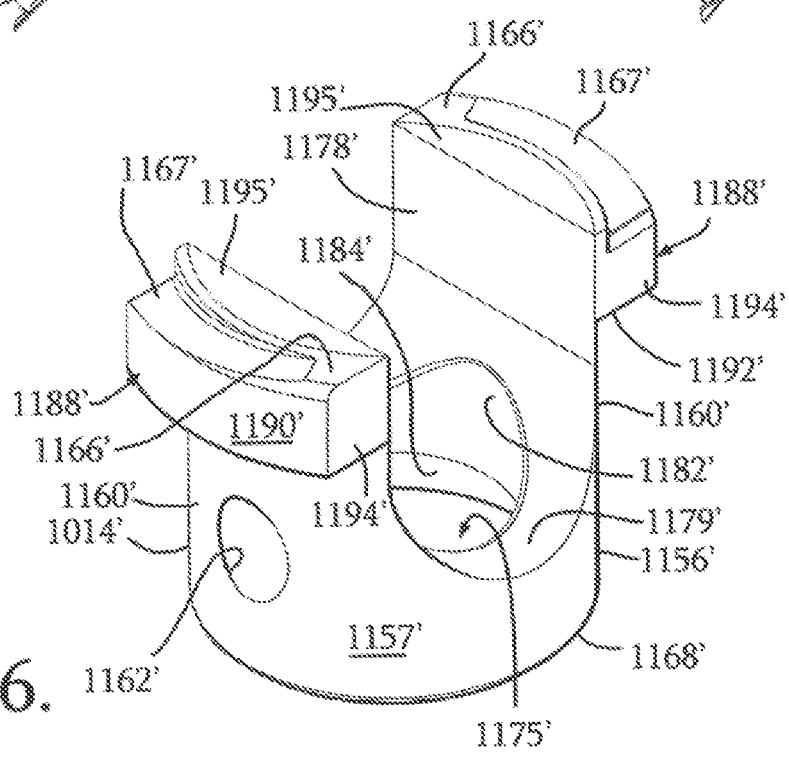
FIG. 56 is an enlarged perspective view of the compression insert of FIG. 55.
Figure 63:
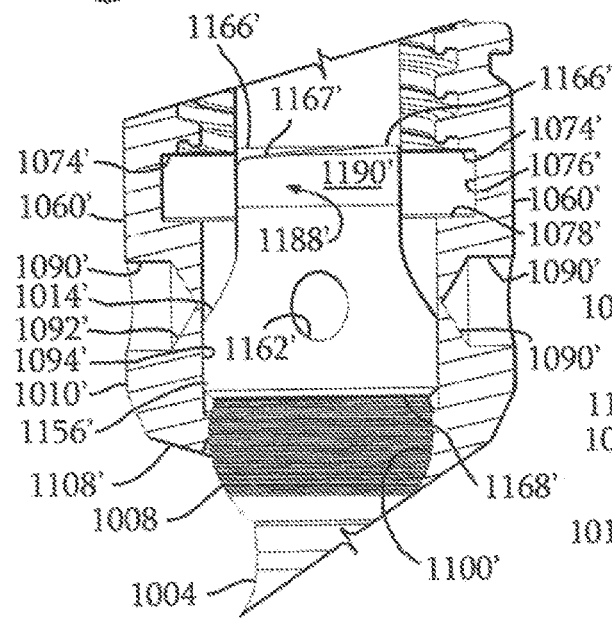
FIG. 63 is an enlarged and partial front elevational view with portions broken away of the receiver, shank and insert of FIG. 55 shown in a stage of assembly wherein the insert is top loaded into the receiver to a location of the shank spherical head.
Figure 64:
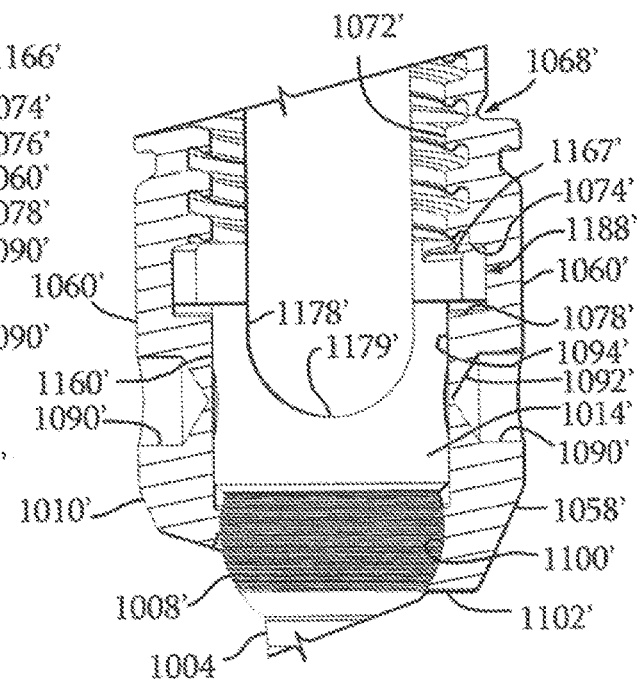
FIG. 64 is an enlarged and partial front elevational view with portions broken away of the assembly of FIG. 63, further showing the insert after being rotated into an operative position.
Figure 65:
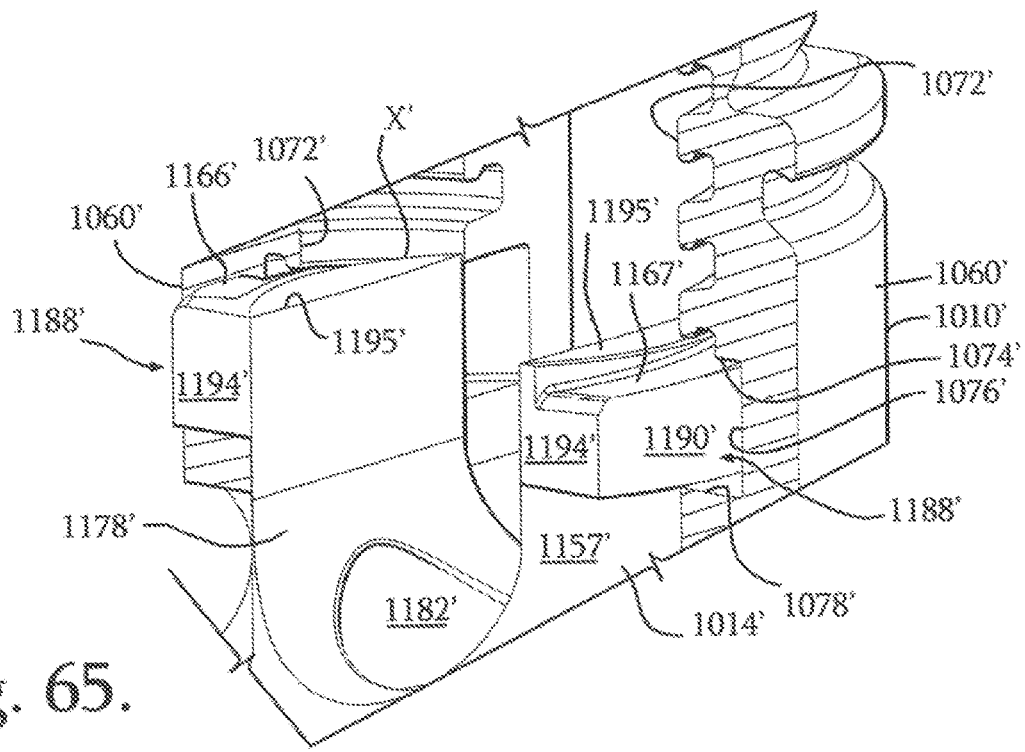
FIG. 65 is a further enlarged and partial perspective view of the insert and receiver as shown in FIG. 64 with portions broken away to show the detail thereof.

With reference to FIGS. 55 and 63, the compression insert 1014' is then downloaded into the receiver 1010' through the receiver upper opening with the insert bottom surface 1168' initially facing the receiver break-off extension arm top surfaces 1070' and the insert arms 1160' located above and between the extension arms 1066'. The insert 1014' is then lowered toward the shank head 1008 until the insert 1014' arms 1160' are located near the receiver annular surface 1074' and the insert bottom rim 1168' is seated on the shank head 1008. With further reference to FIG. 63, at such time lower portions of the ramp surfaces 1167' are located below the surfaces 1074' and the upper un-ramped arm portions 1166' are located slightly above the surfaces 1074'. With reference to FIGS. 63-65, thereafter, the insert 1014' is rotated about the receiver 1010' central axis in a clock-wise direction. Each of the ramp surfaces 1166' initially are relatively easily slidingly received under each surface 1074' and the wings 1188 are slidingly received by the cylindrical surfaces 1076'. Then, as rotation continues, the ramp surfaces 1166' begin to frictionally engage the respective surfaces 1074' until the frictional engagement is such that the ramp surfaces 1166' are wedged against the annular surfaces 1074' and the insert arms 1160' are adjacent the receiver arms 1060' and aligned therewith, with the wing outer surfaces 1190' being closely received and adjacent to the receiver inner cylindrical surfaces 1076', as shown, for example in FIGS. 64-66.

As noted previously, the receiver 1010' flange forms 1072' are positioned to provide adequate clearance between such flange forms and the insert 1014' upper surfaces 1166' and 1167'. With particular reference to FIG. 65, the receiver flange form 1072' terminates at a location X' that allows for a run or helical slope of the flange form 1072' that provides adequate clearance between the flange form 1072' lower contour or toe where the ramp surface 1166' joins with the higher un-ramped portion 1166'. In comparison, reference is made to the location X of the flange form 1072 of the receiver 1010 shown in FIG. 49 that indicates where the receiver flange form 1072 lower contour or toe terminates. The location X' is shifted to the right as compared to the location X of the flange form 1072 toe run-out of the receiver 1010, providing for greater clearance between the flange form 1072' toe near the juncture of the surfaces 1166' and 1167' than between the flange form toe of the form 1072 and the surface 1166.

Figure 66:
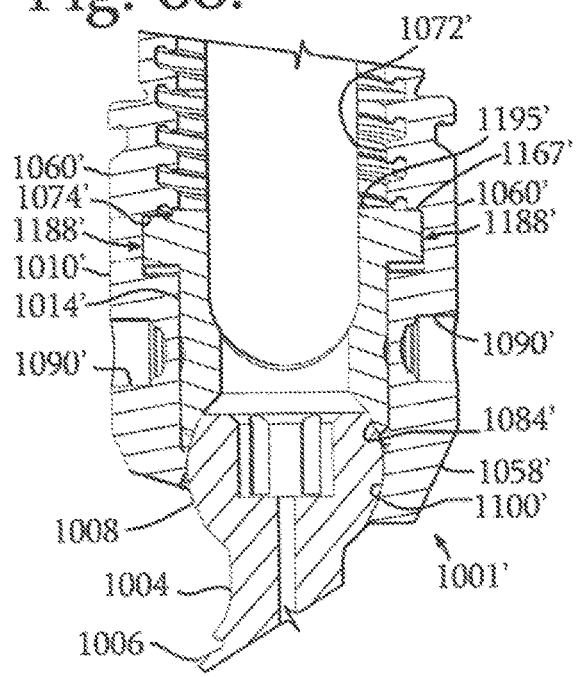
FIG. 66 is a reduced and partial front elevational view of the assembly as shown in FIG. 65 with portions broken away and further showing portions of the receiver crimped against the insert.

After the insert 1014' is rotated into the position shown in FIGS. 64-66, the two crimping wall portions 1092' are pressed inwardly towards the insert 1014' and crimping wall material thus engages the insert walls 1164' defining the insert apertures 1162'. The crimping wall material of the wall 1092' presses against the insert 1014' at two opposed locations thereby prohibiting the insert 1014' from rotating back out of the receiver, in a counter-clockwise direction. The resulting assembly 1001' is now in a desired position for shipping and for implanting into a vertebra, such as the vertebra 17 as previously described herein with respect to the assembly 1 and 1001, prior to locking the insert 1014' against the shank head 1008, the shank 1004 may be pivoted (using some force to overcome the friction fit between the shank head and the receiver) to a plurality of potentially desirable positions with respect to the receiver 1010', followed by locking of the polyaxial mechanism by mating and rotating the multi-start closure top outer structure 1019 with respect to the receiver 1010', the structure 1019' pressing down on the insert 1014' that in turn presses against the shank head 1008 that in turn presses against the receiver 1010'. Thus a variety of different angular or articulated positions of the shank 1004 with respect to the receiver 1010' are possible, some making full use of the sloped bottom surface 1108' as shown, for example in FIGS. 92 and 106.

Figure 67:
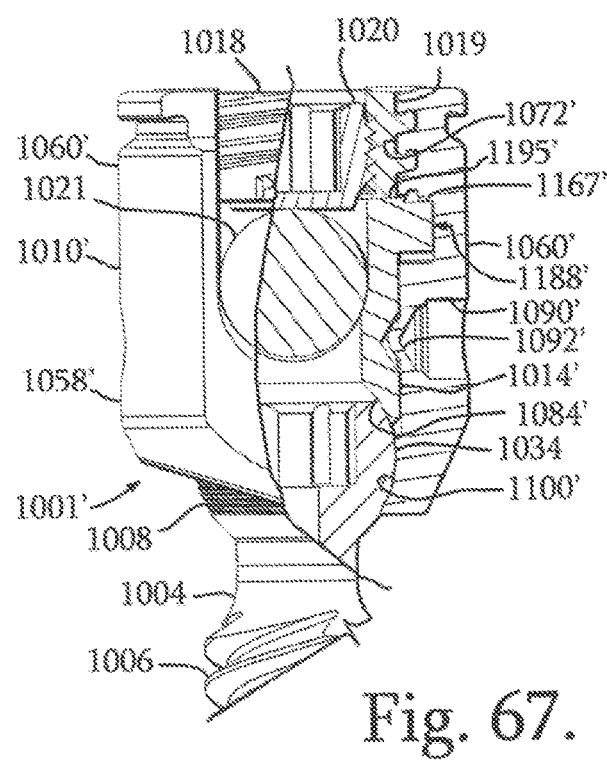
FIG. 67 is a partial front elevational view of the assembly of FIG. 66 with portions broken away and further shown with a rod and a two piece dual start closure top.

With reference to FIG. 67, the rod 1021 is positioned in an open or percutaneous manner in cooperation with the at least two bone screw assemblies 1001' (or 1001 or 1). The closure structure 1018, with the inner threaded plug 1020 already threadably mated with the outer structure 1019 as shown, for example, in FIG. 44, is then inserted into and advanced between the arms 1066' of the break-off extensions of each of the receivers 1010'. The closure structure 1018 is rotated, using a tool engaged with the break-off head drive feature 1215 of the outer closure structure 1019 until a selected pressure is reached at which point the outer structure bottom surface 1206 engages the upper arms surfaces 1195' of the insert 1014' and presses the insert 1014' spherical surface 1184' into locking frictional engagement with the shank head outer surface 1034. As the closure structure 1019 presses downwardly on the compression insert further pressing and then locking the insert spherical surface 1184' against the shank spherical surface 1034 and the shank spherical surface 1034 against the receiver spherical surface 1100', the outer structure 1019 presses the rod 1021 cylindrical surface 1022 to a location at or near the insert saddle seat 1179'. Also, at such time the break-off head 1201 twists off of the fastener 1019 at the weakened region 1207 and is then removed from the receiver arm extensions 1066' and out the top of the channel partially defined by the guide and advancement structure 1072'. After the rod 1021 is manipulated to a desired location and orientation, the inner plug 1020 is then rotated into locking frictional engagement with the rod 1021 by rotating the driving tool (not shown) inserted in the plug inner drive feature 1240.

With reference to FIG. 67, the break-off extensions 1066' are then removed by pivoting or bending the extensions 1066' back and forth at the weakened regions 1068' and 1079' formed by the respective outer groove or notch 1071' and inner recess 1080'. The resulting low-profile implanted structure is also shown in FIG. 67.

Figure 68:
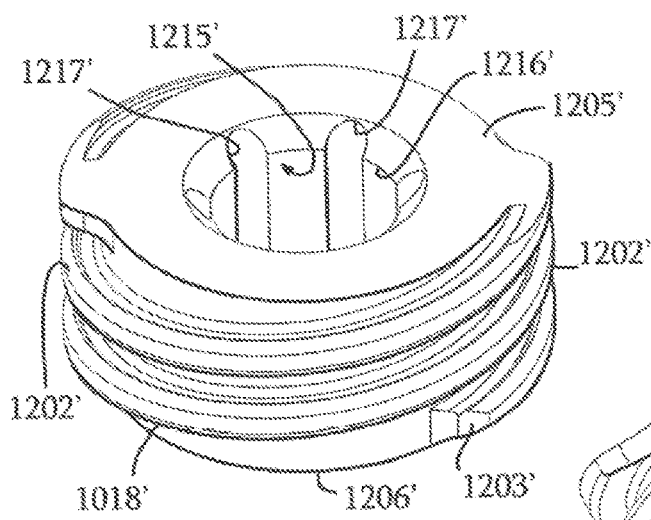
FIG. 68 is a perspective view of an alternative single piece dual start closure top.
Figure 69:
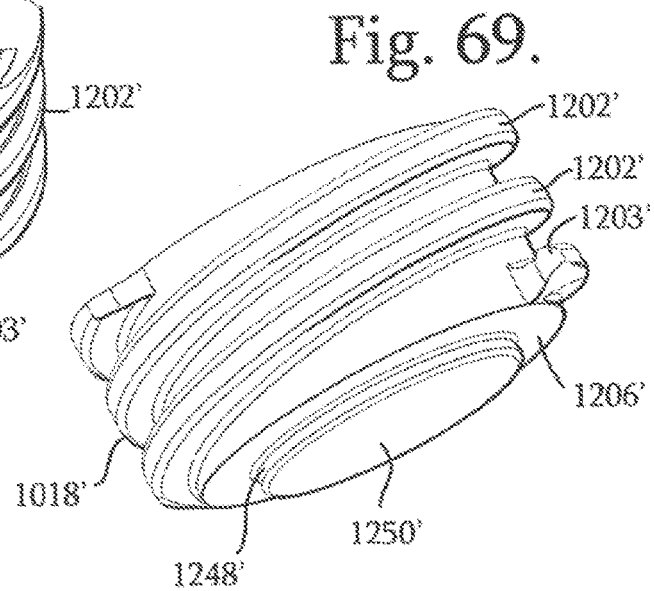
FIG. 69 is another perspective view of the alternative closure top of FIG. 68.
Figure 70:
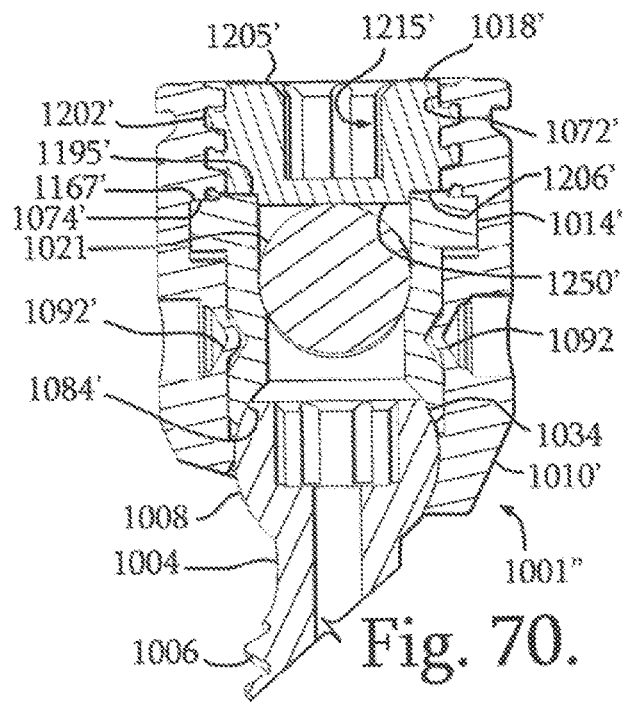
FIG. 70 is a partial front elevational view of the assembly of FIG. 66 with portions broken away and shown with a rod and the alternative singe piece closure top of FIG. 68, shown in reduced front elevation and with portions broken away to show the detail thereof.

With reference to FIGS. 68-70, an alternative multi-start one piece closure 1018' is illustrated for use with the assembly 1001' in lieu of the two piece closure 1018. The alternative closure 1018' is shown assembled with the assembled shank 1008, receiver 1010' and cam insert 1014' in FIG. 70, resulting in an alternative bone screw assembly 1001". The alternative closure 1018' includes a dual start flange form 1202', two starts 1203', a top surface 1205', a bottom surface 1206', an inner drive 1215' that includes an inner cylindrical surface 1216' and driving lobes 1217' that are substantially similar to the respective dual start flange form 1202, two starts 1203, top surface 1205, bottom surface 1206, inner drive 1215 that includes the inner cylindrical surface 1216 and driving lobes 1217 previously described herein with respect to the two-piece closure 1018. The closure 1018' further includes an extended portion defined by a lower substantially cylindrical surface 1248' adjacent and substantially perpendicular to the bottom surface 1206' and a planar base surface 1250' perpendicular to the cylindrical surface 1248' and substantially parallel to the surface 1206'. As shown in FIG. 70, the cylindrical surface 1248' and the base 1250' are sized and shaped such that when the surfaces 1248' and 1250' are received between the arms of the insert 1014', the base or bottom 1250' frictionally engages and fixes against the rod 1021, locking the rod in place against the insert, the rod in turn pressing the insert 1014' into locking engagement with the shank head 1008 at the surface 1034. Thus, the illustrated components are sized so that there is a space between the annular lower surface 1206' and the insert arm surfaces 1195' to ensure adequate locking of the rod 1021 between the closure 1018' and the insert 1014'. However, in some embodiments, the cylindrical surface 1248' may be sized and shaped such that the surfaces 1248' and 1250' are received between the arms of the insert 1014' and the base or bottom surface 1250' simultaneously frictionally engages and fixes against the rod 1021 when the annular lower surface 1206' presses the insert 1014' at the arm surfaces 1195' that in turn presses the insert surface 1084' into locking engagement with the shank head 1008 at the surface 1034.

With reference to FIGS. 71-92, another embodiment of a polyaxial bone anchor is shown that is identified generally as 2001. In addition to components that are similar to the receiver, cam surface insert and two-piece dual start closure previously described herein, the assembly 2001 includes an upload-able shank that cooperates with an open, resilient retainer that is located within the receiver and allows for a snap-on or pop-on assembly of the shank with the receiver either before or after the shank as been implanted in a vertebra, such as the vertebra 17.

Specifically, With reference to FIGS. 71 and 90-92, the open implant in the form of a polyaxial bone screw apparatus or assembly 2001 includes a shank 2004, that further includes a body 2006 integral with an upwardly extending partially spherical and partially cylindrical upper portion or head 2008; a receiver 2010; a resilient open retainer 2012; a cam-top compression or pressure insert 2014; and a two piece multi-start closure structure or top 2018 that includes an outer structure 2019 having a double-start helically wound flange-form and a threaded inner plug 2020. Similar to what has been described above with respect to the assembly 1001, the outer structure 2019 mates with the receiver 2010 and presses downwardly against the insert 2014 that in turn presses against the shank head 2008 (and also against the retainer 2012 when the shank is pivoted in certain positions) while the inner plug 2020 ultimately presses against a longitudinal connecting member, for example, a rod 2021, so as to capture, and fix the longitudinal connecting member 2021 within the receiver 2010 and thus fix the member 2021 relative to a vertebra, such as the vertebra 17 shown with respect to the assembly 1. The receiver 2010, shank 2004 and retainer 2012 are typically initially assembled and then assembled with the insert 1014 prior to implantation of the shank body 1006 into the vertebra 1017. It is foreseen that in some embodiments, another alternative insert may be initially assembled with the receiver and the retainer and then the shank may be assembled with the other components either before or after implanting the shank into a vertebra.

With particular reference to FIGS. 71-74, the shank 2004 is similar to the shanks 4 and 1004 previously described herein with the exception of some of the surfaces of the shank upper portion 2008 that will be described in greater detail below. Thus, the shank 2004 includes lower and upper thread portions 2024 and 2025, a neck 2026, a tip 2028, a shank body top 2032, a substantially planar shank head top 2036 and a drive 2050 with an upper frusto-conical surface 2048, a drive annular planar base 2049, a drive cylindrical wall 2052, driving lobes 2053, a drive step 2054 and a cannulation bore 2055 the same or substantially similar in form and function to the respective lower and upper thread portions 1024 and 1025, neck 1026, tip 1028, shank body top 1032, planar top 1036 and drive 1050 with upper frusto-conical surface 1048, drive annular planar base 1049, drive cylindrical wall 1052, driving lobes 1053, drive step 1054 and cannulation bore 1055 of the shank 1004 previously described herein with respect to the assembly 1001 (that has the same or similar features previously described herein with respect to the shank 4).

Figure 72:
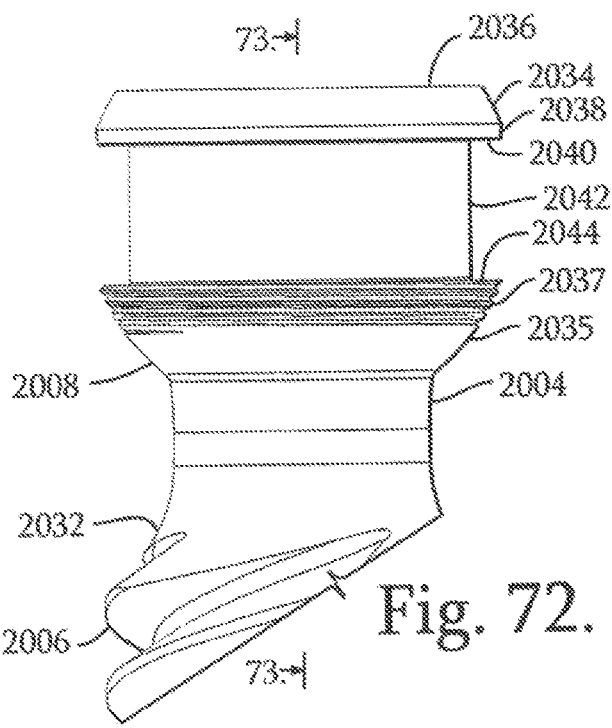
FIG. 72 is an enlarged and partial front elevational view of the shank of FIG. 71.
Figure 73:
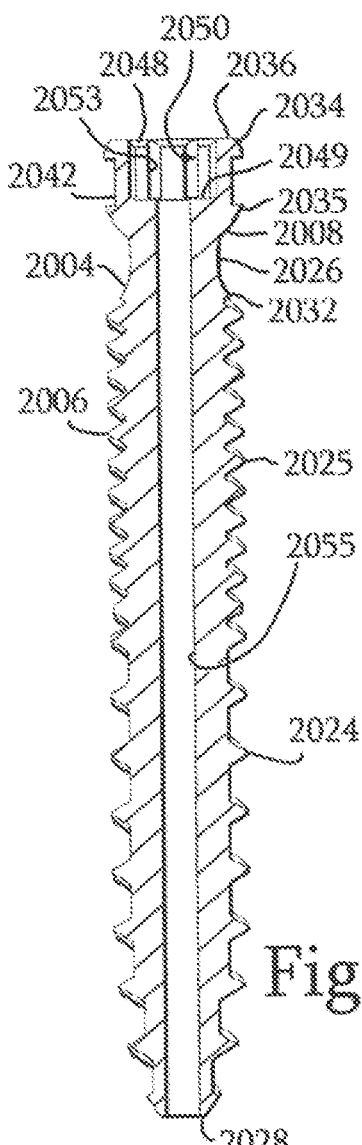
FIG. 73 is a reduced cross-sectional view taken along the line 73-73 of FIG. 72.
Figure 74:
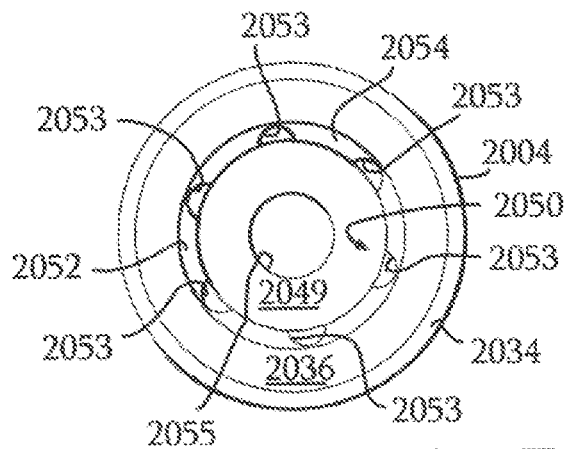
FIG. 74 is a reduced top plan view of the shank of FIG. 72.

However, as compared to the shank head 1004 substantially spherical surface 1034 having ridges 1037, the shank head or upper portion 2008 includes an upper substantially spherical portion 2034 located near the top surface 2036 and a separated lower spherical portion 2035, the surfaces 2034 and 2035 having an identical or substantially similar radius, the illustrated lower portion 2035 having ridges 2037 formed thereon as best shown, for example, in FIG. 72. Extending downwardly from the top spherical surface 2034 is a substantially cylindrical surface 2038. Extending inwardly from the surface 2038 is a substantially planar annular lip surface 2040 that runs inwardly to a substantially cylindrical surface 2042. Located below and adjacent to the cylindrical surface 2042 is another annular surface or ledge 2044 that faces upwardly toward the lip surface 2040 and is parallel thereto. Both the annular surfaces 2040 and 2044 are perpendicular to a central axis of the shank 2004, while the cylindrical surface 2042 runs parallel to the central axis. As will be discussed in greater detail below, the upper lip or ledge 2040, cylindrical surface 2042 and lower ledge 2044 cooperate to capture and fix the resilient open retainer 2012 to the shank upper portion 2008, prohibiting movement of the retainer 2012 along the shank central axis once the retainer 2012 is located between the ledges 2040 and 2044. The cylindrical surface 2038 that extends upwardly from the ledge 2040 has a radius smaller than the radius of the spherical surface 2034 but larger than the radius of the cylindrical surface 2042. The spherical surface 2034 radius is configured for sliding cooperation and ultimate frictional mating with a substantially spherical concave surface of the compression insert 2014 that has the same or substantially similar radius as the surface 2034.

With particular reference to FIGS. 71 and 78-81, the receiver 2010 is substantially similar in form and function to the receiver 1010 previously described herein with respect to the assembly 1001 with the exception of some inner geometry for receiving and capturing the resilient open retainer 2012. Thus, the receiver 2010 includes a base 2058 and integral arms 2060, a base cavity 2061, arm extensions 2066, inner flange forms 2072 extending along each arm 2060 and arm extension 2066, a weakened region, generally 2068 on each arm that includes an outer notch or v-cut 2071 and an inner weakened region, generally 2079 that includes an inner recess 2080, extension top surfaces 2070, crimp recesses 2090 and crimping walls 2092 that are the same or substantially similar in form and function the to the respective receiver 1010 base 1058, integral arms 1060, base cavity 1061, arm extensions 1066, inner flange forms 1072 extending along each arm 1060 and arm extension 1066, the weakened region 1068 on each arm that includes the outer notch or v-cut 1071 and weakened inner region 1079 that includes the inner recess 1080, extension top surfaces 1070, crimp recesses 1090 and crimping walls 1092, as well as many other features shown in the receiver 1010 and also the receiver 10 previously described herein.

With respect to inner surfaces of the receiver 2010 arms 2060, shown for example, in FIGS. 78 and 79, an annular run out surface 2074 and inner cylindrical surface 2076 and an annular surface or ledge 2078 form a run-out area and receiving area for the insert 2014. The surfaces 2074, 2076 and 2078 are similar in form to the respective surfaces 1074, 1076 and 1078 of the receiver 1010. With respect to the base cavity 2061, the receiver 2010 includes a cylindrical surface 2094, a circular spheric edge 2098, an inner spherical surface 2100 and other lower cavity features that are identical or substantially similar to the cylindrical surface 1094, circular spheric edge 1098, inner spherical surface 1100 and other features of the base cavity 1061 previously described herein with respect to the assembly 1001. The receiver 2010 further includes planar bottom surfaces 2102 and 2108 and other features defining a lower opening 2110 that are the same or substantially similar in form and function to the respective surfaces 1102 and 1108 and other features defining the lower opening 1110 of the receiver 1010 previously described herein. However, the receiver 2010 inner cavity 2061 further includes surfaces located between the cylindrical surface 2094 and the spherical surface 2100 that are sized and shaped for receiving and retaining the retainer 2012 and such surfaces include an outwardly extending substantially annular surface or lip 2095 located adjacent the cylindrical surface 2094 that is also adjacent to a second substantially spherical surface 2096. The surface 2096 has a radius that is larger than the radius of the surface 2100 and is sized and shaped to provide an expansion chamber to receive an expanded retainer 2012 and the shank head 2008 as will be described in greater detail below. A lower annular ledge 2097 extends inwardly from the spherical surface 2096 and joins with the spherical surface 2100 at the circular spheric edge 2098. Furthermore, two opposed recesses 2111 are cut or otherwise formed in the surface 2096. The recesses 2111 are sized and shaped for receiving tooling to hold the retainer 2012 within the receiver surface 2096 during expansion of the retainer 2012 and up or bottom loading of the shank 2004 into the receiver 2010 as will be described in greater detail below.

Figure 75:
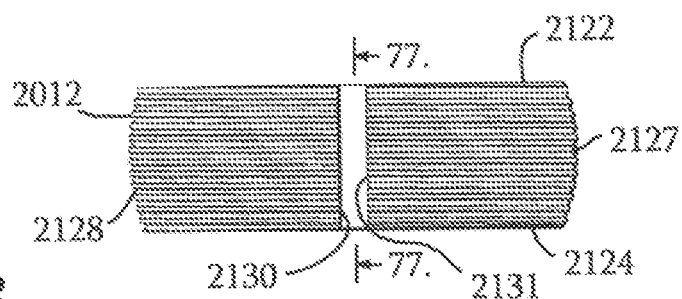
FIG. 75 is an enlarged front elevational view of the retainer of FIG. 71.
Figure 76:
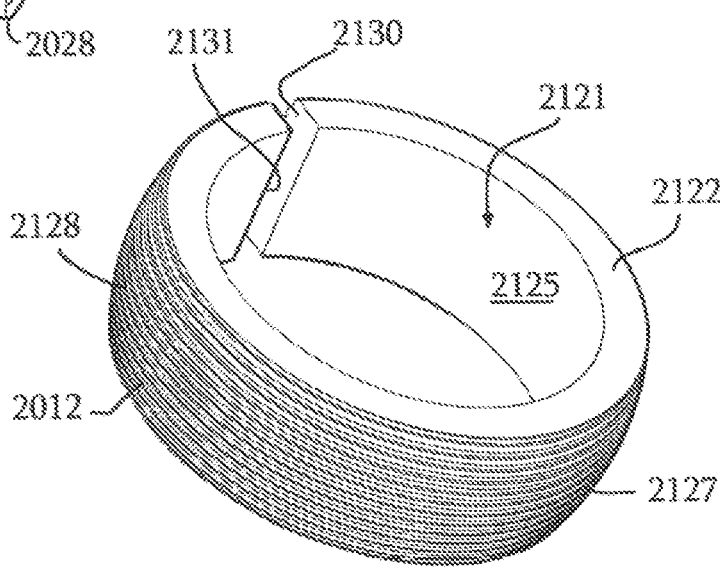
FIG. 76 is an enlarged perspective view of the retainer of FIG. 75.

With particular reference to FIGS. 71 and 75-77, the open retainer 2012 that operates to capture the shank upper portion 2008 within the receiver 2010 has a central axis that is operationally the same as the central axis associated with the shank 2004 when the shank upper portion 2008 and the retainer 2012 are installed within the receiver 2010. The retainer 2012 is preferably made from a resilient material, such as a stainless steel or titanium alloy, so that the retainer 2012 may be expanded during assembly as will be described in greater detail below. The retainer may also be made from cobalt-chrome. Because there is no need to compress the retainer 2012 during assembly, the opening or slit that allows for expansion of the retainer 2012 may be designed to be narrow, advantageously providing substantial surface contact between the retainer 2012 and the shank upper portion 2008 and also between the retainer 2012 and the receiver seating surface 2100. The retainer 2012 has a central channel or hollow through bore, generally 2121, that passes entirely through the structure 2012 from a top surface 2122 to a bottom surface 2124 thereof. The bore 2121 is primarily defined by a discontinuous inner cylindrical surface 2125 that runs from the top surface 2122 to the bottom surface 2124. In some embodiments of the invention, notches or grooves may be formed in the inner, outer, top and/or bottom surfaces of the retainer 2012 to more evenly distribute stress across the entire retainer during expansion thereof. The retainer 2012 further includes an outer substantially spherical surface 2127 running between the top surface 2122 and the bottom surface 2124, the surface 2127 having the same or similar radius as the receiver seating surface 2100 and the shank upper spherical surface 2034 and lower spherical surface 2035. In the illustrated embodiment, a helically wound groove 2128 extends over the entire surface 2127. It is foreseen that in other embodiments, part or all of the surface 2127 may have a groove or grooves, ridges or other surface treatment or may be smooth. The retainer 2012 further includes first and second end surfaces, 2130 and 2131 disposed in spaced relation to one another when the retainer is in a neutral state. Both end surfaces 2130 and 2130 are disposed substantially perpendicular to the top surface 2122 and the bottom surface 2124. The embodiment shown in FIGS. 75-77 illustrates the surfaces 2130 and 2131 as substantially parallel and vertical, however, it is foreseen that it may be desirable to orient the surfaces obliquely or at a slight angle with respect to the top and bottom surfaces.

With reference to FIGS. 71 and 90-92, the insert 2014 is identical or substantially similar in form and function to the insert 1014' previously described herein and shown in FIGS. 55-67. Thus, the insert 2014 includes an insert body 2156, an outer substantially cylindrical surface 2157, opposed upstanding arms 2160 each with a crimp aperture 2162 having a substantially conical wall 2164, arm tops 2166, each with a ramped surface 2167, a bottom annular planar rim surface 2168 terminating at a frusto-conical chamfer 2170, a through bore generally 2175, a saddle 2178 a lower saddle seat 2179, an inner cylindrical surface 2182, a lower curved or radiused surface portion 2184, a pair of wings 2188 extending outwardly from the insert arms, each wing having an outer cylindrical surface 2190, a bottom surface 2192, front and back surfaces 2194 and a top inwardly sloping surface 2195 located adjacent the saddle surface 2178 that are the same or substantially similar in form and function to the respective body 1156', outer substantially cylindrical surface 1157', opposed upstanding arms 1160' each with crimp apertures 1162' having substantially conical walls 1164', arm top surfaces 1166' with ramped surface portions 1167', the bottom annular planar rim surface 1168' terminating at the frusto-conical chamfer 1170', the through bore 1175', saddle 1178', lower saddle seat 1179', inner cylindrical surface 1182', lower curved or radiused surface portion 1184', outwardly extending wings 1188', each wing having the outer cylindrical surface 1190', bottom surface 1192', front and back surfaces 1194', and the top inwardly sloping surface 1195' located adjacent the saddle surface 1178' of the insert 1014' previously described herein (most of the components of which were also previously described herein with respect to the insert 14).

With reference to FIGS. 71 and 90-92, the closure 2018 having the outer structure 2019 and the inner set screw 2020 is identical or substantially similar to the closure 1018 previously described herein. The illustrations show the closure 2018 after the break-off head has been removed. As the closure 1018 has been fully described above, the closure 2018 will not be further described herein with the exception of identifying some of the features that are the same or substantially similar to the closure 1018 features to facilitate further description of the assembly and operation of the bone screw 2001. Thus, the closure 2018 includes an outer structure dual start flange form 2202, an outer structure top surface 2205 (not shown), an outer structure bottom surface 2206, an outer structure inner v-thread 2210, an outer structure multi-lobular drive 2215 (not shown), an inner set screw top 2226, a set screw bottom 2227, a set screw v-thread 2232 and a set screw multi-lobular drive feature 2240, such features being the same or substantially similar in form and function to the respective outer structure dual start flange form 1202, outer structure top surface 1205, outer structure bottom surface 1206, outer structure inner v-thread 1210, outer structure multi-lobular drive 1215, inner set screw top 1226, set screw bottom 1227, set screw v-thread 1232 and set screw drive feature 1240 of the closure 1018 previously described herein.

Figure 82:
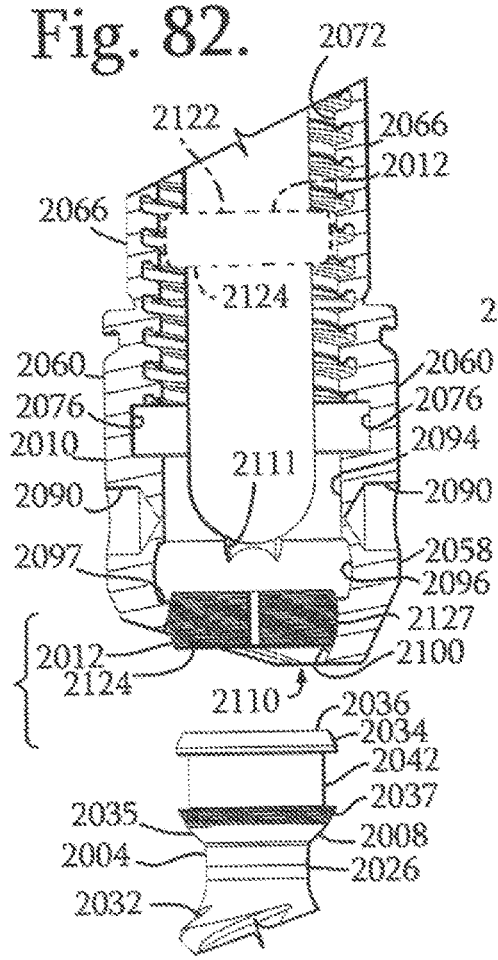
FIG. 82 is an enlarged and partial front elevational view with portions broken away of the receiver, retainer and shank of FIG. 71 showing the retainer loaded in the receiver (top loading stage shown in phantom) and the shank just prior to being loaded in the receiver.

With reference to FIGS. 82-92, the bone screw assembly 2001 may be assembled as follows: With particular reference to FIG. 82, first the retainer 2012 is inserted into the upper receiver opening, leading with the bottom surface 2124, the retainer outer surface 2127 facing the opposing arm extensions 2066. The retainer 2012 is then lowered into the receiver 2010 as shown in phantom in FIG. 82 until the surface 2127 seats on the receiver surface 2100. The retainer 2012 may need to be compressed slightly with the surfaces 2130 and 2131 being moved toward one another as the retainer passes by the receiver ledge 2097 having the inner spheric edge 2098.

Figure 83:
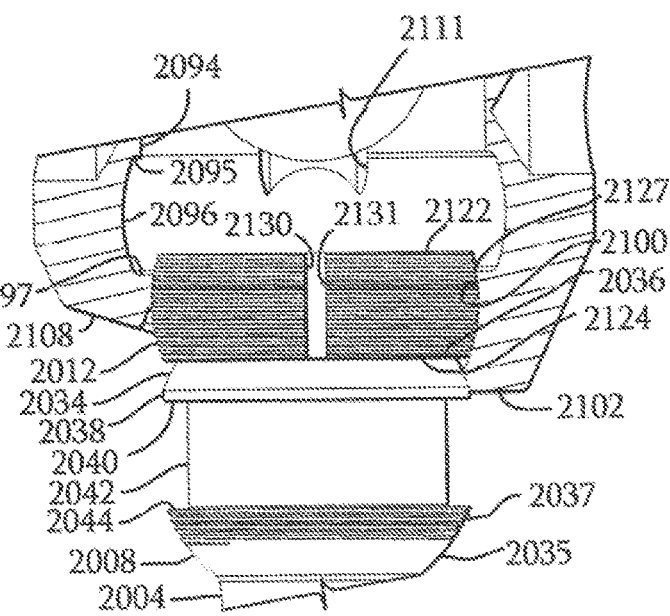
FIG. 83 is an enlarged and partial front elevational view with portions broken away of the assembly of FIG. 82 showing the shank in a first stage of assembly with the retainer.
Figure 84:
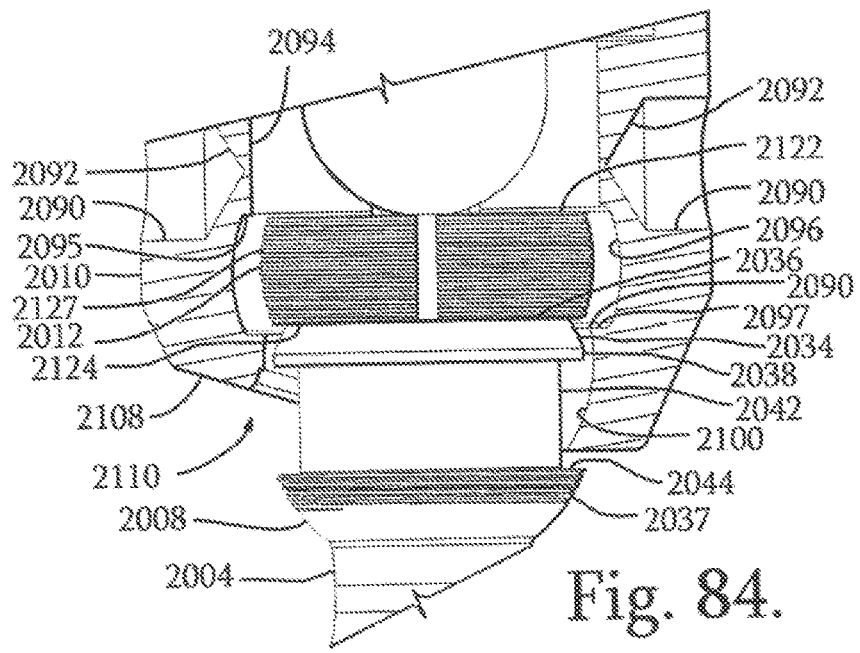
FIG. 84 is an enlarged and partial front elevational view with portions broken away of the assembly of FIG. 83 showing a subsequent stage of assembly wherein the shank enters the receiver and presses upwardly on the retainer.
Figure 85:
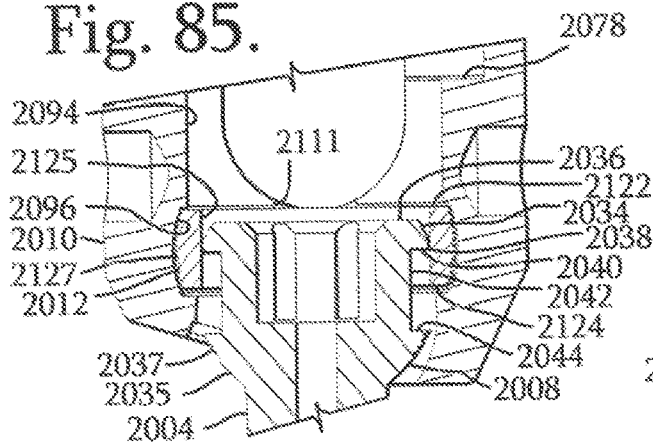
FIG. 85 is a reduced and partial front elevational view with portions broken away of the assembly of FIG. 84 showing a further stage of assembly wherein the retainer is expanded about the shank.
Figure 86:
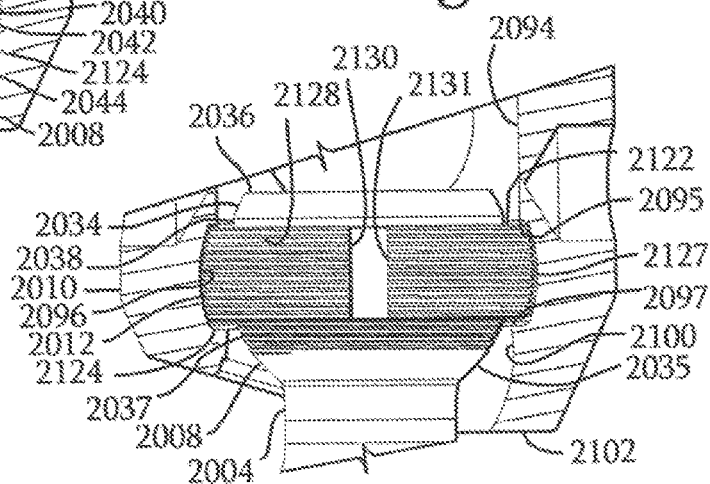
FIG. 86 is an enlarged and partial front elevational view with portions broken away of the assembly of FIG. 85 showing the expanded retainer just prior to being positioned at a cylindrical surface of the shank.
Figure 87:
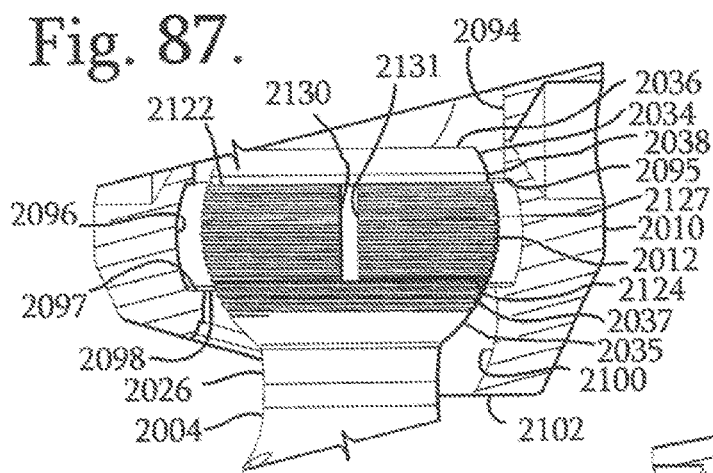
FIG. 87 is a partial front elevational view with portions broken away of the assembly of FIG. 86 wherein the retainer contracts to a neutral or nominal position about the cylindrical surface of the shank.

With reference to FIG. 83, at this time a blocking tool (not shown) is inserted into the receiver 2010 from the top opening thereof and is slid along the opposed apertures 2111 until a bottom surfaces of the tool engage the top surface 2122 of the retainer 2012. As the shank head top surface 2036 is moved into the receiver at the lower opening 2110 thereof and into the retainer central bore 2121, the tool (not shown) keeps the retainer top surface 2122 at a location illustrated in FIG. 84, the retainer top surface 2122 being slightly beneath the receiver surface 2095 placing the retainer 2012 within the receiver expansion chamber defined by the surface 2096. With further reference to FIG. 84 and also with reference to FIG. 85, as the shank upper portion surface 2034 moves upwardly and abuts against the retainer inner surface 2125, the shank upper portion 2008 pushes the retainer outwardly until the retainer outer surface 2127 reaches to or near the receiver spherical surface 2096 and the retainer top surface 2122 abuts against the receiver surface 2095. Thereafter, as best shown in FIGS. 86 and 87, the resilient retainer 2012 stays expanded as the shank surface 2038 slides along the retainer inner cylindrical surface 2125 and the retainer contracts to a neutral or near neutral position after the retainer inner cylindrical surface 2125 fully aligns with the shank upper portion cylindrical surface 2040. With further reference to FIG. 87, now the retainer 2012 is affixed to the shank upper portion 2008 with the retainer top surface 2122 located below the shank annular surface 2040 and the retainer bottom surface 2124 located above the shank annular surface 2044 and with the retainer inner cylindrical surface 2125 engaging the shank cylindrical surface 2042. The now fully assembled shank and retainer combination is shown in FIGS. 87 and 88 and it can be seen that the retainer outer surface 2127 has the same radius as the shank surfaces 2034 and 2035. Thereafter the shank and affixed retainer are pulled downwardly into friction fit engagement with the receiver surface 2100 as described previously herein with respect to the single piece shank head 8 and the receiver 10, the shank 2004 and attached retainer 2012 being pivotable with respect to the receiver 2010 when some force is used to slide the retainer surface 2127 with groove 2128 as well as the shank surface 2035 with groove 2037 along the receiver surface 2100.

With reference to FIG. 89, the cam-top insert 2014 is then loaded and rotated into an operational position in a manner described previously with respect to the cam-top insert 1014' and the receiver 1010' and shown in FIGS. 63-66. With reference to FIG. 90, eventually the rod 2021 or other longitudinal connecting member and the closure 2018 are positioned and tightened in a manner identical to that described previously herein with respect to the rod 1021 and the closure 1018 and shown in FIG. 67. As shown in FIG. 90, the closure outer structure 2019 bottom surface 2206 engages the insert 2014 arm top surfaces 2195, pressing the insert downwardly into locking engagement with the shank upper portion surface 2034, the retainer surface 2127 and the shank surface 2035 being placed in locked frictional engagement with the receiver inner spherical surface 2100. As shown in FIGS. 91 and 92, if the shank 2004 has been pivoted with respect to the receiver 2010 prior to locking, portions of the retainer surface 2127 may also be in fixed frictional engagement with the insert lower spherical surface 2184. FIG. 91 illustrates a fifty degree medial angulation of the shank 2004 with respect to the receiver 2010 made possible by the receiver geometry that includes the bottom angled surface 2108. FIG. 92 illustrates a ten degree lateral angulation of the shank 2004 with respect to the receiver 2010. Also with respect to FIGS. 90-92, the rod is eventually fixed against the insert 2014 by direct pressure from the closure set screw 2020, the set screw bottom surface 2227 in frictional engagement with the rod cylindrical surface 2022. The inner set screw 2020 is rotated and moved downwardly into engagement with the rod 2021 in the manner described previously with respect to the closure set screw 1020 and the rod 1021 and shown in FIG. 67.

With reference to FIGS. 93-99, another embodiment of a polyaxial bone anchor is shown that is identified generally as 3001. In addition to components that are similar to the receiver and insert of the bone screw assembly 1 and two-piece dual start closure previously described herein with respect to the bone screw assembly 1001 (and 2001), the assembly 3001 includes an upload-able shank that cooperates with a closed, threaded retainer that is located within the receiver and allows for uploading the shank into the receiver.

Specifically, with reference to FIGS. 93 and 99, the open implant in the form of the polyaxial bone screw apparatus or assembly 3001 includes a shank 3004, that further includes a body 3006 integral with an upwardly extending partially spherical and partially threaded upper portion or head 3008; a receiver 3010; a closed retainer or ring 3012; a compression or pressure insert 3014; and a two piece multi-start closure structure or top 3018 that includes an outer structure 3019 having a double-start helically wound flange-form and a threaded inner plug 3020. Similar to what has been described above with respect to the assembly 1001, the outer structure 3019 mates with the receiver 3010 and presses downwardly against the insert 3014 that in turn presses against the shank head 3008 (and also against the retainer 3012 when the shank is pivoted in certain positions) while the inner plug 3020 ultimately presses against a longitudinal connecting member, for example, a rod 3021, so as to capture, and fix the longitudinal connecting member 3021 within the receiver 3010 and thus fix the member 3021 relative to a vertebra, such as the vertebra 17 shown with respect to the assembly 1. The receiver 3010, shank 3004 and retainer 3012 are typically initially assembled and then assembled with the insert 3014 prior to implantation of the shank body 3006 into the vertebra, such as the vertebra 17. It is foreseen that in some embodiments, the insert 3014 may be initially assembled with the receiver 3010 and the retainer 3012 and then the shank 3004 may be assembled with the retainer 3012 that is already in the receiver 3010 either before or after implanting the shank body 3006 into a vertebra.

With particular reference to FIGS. 93-94, the shank 3004 is similar to the shanks 4 and 1004 previously described herein with the exception of some of the surfaces of the shank upper portion 3008 that will be described in greater detail below. Thus, the shank body 3006 includes lower and upper thread portions 3024 and 3025, a neck 3026, a tip 3028, a shank body top 3032, a substantially planar shank head top 3036, a multi-lobular drive 3050 and a cannulation bore 3055 the same or substantially similar in form and function to the respective lower and upper thread portions 24 and 25, neck 26, tip 28, shank body top 32, planar top 36, drive 50 and cannulation bore 55 of the shank 4 previously described herein with respect to the assembly 1.

However, as compared to the shank head 4 substantially spherical surface 34 having ridges 37 and 38, the shank head or upper portion 3008 includes only a lower spherical surface portion 3035 adjacent the neck 3026, the lower portion 3035 having ridges 3037 formed thereon as best shown, for example, in FIG. 94. Extending downwardly from the top surface 3036 is a substantially cylindrical surface 3038. Extending downwardly from the surface 3038 is a helically wound v-thread 3040 that terminates near a lower annular surface or ledge 3044 that faces upwardly and is substantially perpendicular to a central axis of the shank 3004. As will be discussed in greater detail below, the shank upper portion thread 3040 cooperates and mates under rotation with an inner threaded portion of the retainer 3012 to fix the retainer 3012 to the shank 3004.

With particular reference to FIGS. 71 and 78-81, the receiver 3010 is substantially similar in form and function to the receiver 10 previously described herein with respect to the assembly 1. Thus, the receiver 3010 includes a receiver base 3058, a pair of opposed arms 3060, a cavity 3061 formed in the base 3058, a pair of opposed break-off extensions 3066 having weakened regions 3068, extension top surfaces 3070, a guide and advancement structure 3072 for cooperating with a dual start flange form of the closure 3018, an annular run-out surface 3074, an inner cylindrical surface 3076, an annular surface 3078 at a bottom of the run out, a pair of crimp recesses 3090 and corresponding crimping walls 3092, a cylindrical surface 3094 partially defining the arms and partially defining the receiver cavity, an edge 3098 partially defining a spherical surface 3100 of the receiver cavity, a bottom surface 3102 substantially perpendicular to a central axis of the receiver 3010, a bottom angled surface 3108 and a lower opening 3110 that are identical or substantially similar in form and function to the respective receiver base 58, pair of opposed arms 60, cavity 61 formed in the base 58, pair of opposed break-off extensions 66 having weakened regions 68, extension top surfaces 70, the guide and advancement structure 72 for cooperating with the dual start flange form of the closure 18, the annular run-out surface 74, inner cylindrical surface 76, annular surface 78 at the bottom of the run out, the pair of crimp recesses 90 and corresponding crimping walls 92, the cylindrical surface 94 partially defining the arms and partially defining the receiver cavity, the edge 98 partially defining a spherical surface 100 forming the receiver cavity, the bottom surface 102 substantially perpendicular to the central axis of the receiver 10, the bottom angled surface 108 and the lower opening 110 of the receiver 10 previously described herein. Also, other numbered features of the receiver 10 not mentioned here have an identical or substantially similar counterpart in the receiver 3010.

With particular reference to FIGS. 93 and 96, the closed retainer 3012 or ring that operates to capture the shank upper portion 3008 within the receiver 3010 has a central axis that is operationally the same as the central axis associated with the shank 3004 when the shank upper portion 3008 and the retainer 3012 are attached to one another within the receiver 3010. The retainer 3012 has a central channel or hollow through bore, generally 3121, that passes entirely through the structure 3012 from a top surface 3122 to a bottom surface 3124 thereof. The bore 3121 is primarily defined by an upper inner cylindrical surface 3125 that runs from the top surface 3122 to an inner threaded surface 3126. The illustrated surface 3126 is a single v-thread sized and shaped for mating engagement under rotation with the v-thread 3040 on the shank upper portion 3008. In some embodiments of the invention other helically wound thread or thread-like or non-threadlike guide and advancement structures may be used in lieu of the v-thread 3126 and the mating thread 3040. The retainer 3012 further includes an outer substantially spherical surface 3127 running between the top surface 3122 and the bottom surface 3124, the surface 3127 having the same or similar radius as the receiver seating surface 3100 and the shank lower spherical surface 3035. In the illustrated embodiment, the surface 3127 is smooth, but it is foreseen that the surface may include grooves or other surface features sized and shaped for frictional gripping with the receiver inner spherical surface 3100 and the insert 3014.

With reference to FIGS. 93, 98 and 99, the insert 3014 is illustrated that is identical or substantially similar in form and function to the insert 14 previously described herein with respect to the assembly 1 and is shown in greater detail in FIGS. 11-15. Thus, the insert 3014 includes an insert body 3156, an outer substantially cylindrical surface 3157, opposed upstanding arms 3160 each with a crimp aperture 3162, arm tops 3166, a bottom annular planar rim surface 3168, a through bore generally 3175, a saddle 3178 a lower saddle seat 3179, an inner cylindrical surface 3182 and a lower curved or radiused surface portion 3184 that are the same or substantially similar to the respective body 156, outer substantially cylindrical surface 157, opposed upstanding arms 160 each with crimp apertures 162, arm top surfaces 166, the bottom annular planar rim surface 168, the through bore 175, saddle 178, lower saddle seat 179, inner cylindrical surface 182 and lower curved or radiused surface portion 184 of the insert 14 previously described herein.

With reference to FIGS. 93 and 99, the closure 3018 having the outer structure 3019 and the inner set screw 3020 is identical or substantially similar to the closure 1018 previously described herein. The illustrations show the closure 3018 after the break-off head has been removed. As the closure 1018 has been fully described above, the closure 3018 will not be further described herein with the exception of identifying some of the features that are the same or substantially similar to the closure 1018 features to facilitate further description of the assembly and operation of the bone screw 3001. Thus, the closure 3018 includes an outer structure dual start flange form 3202, an outer structure top surface 3205 (not shown), an outer structure bottom surface 3206, an outer structure inner v-thread 3210, an outer structure multi-lobular drive 3215 (not shown), an inner set screw top 3226, a set screw bottom 3227, a set screw v-thread 3232 and a set screw multi-lobular drive feature 3240, such features being the same or substantially similar to the respective outer structure dual start flange form 1202, outer structure top surface 1205, outer structure bottom surface 1206, outer structure inner v-thread 1210, outer structure multi-lobular drive 1215, inner set screw top 1226, set screw bottom 1227, set screw v-thread 1232 and set screw drive feature 1240 of the closure 1018 previously described herein.

With reference to FIGS. 97-99, the bone screw assembly 3001 may be assembled as follows: With particular reference to FIG. 97, first the retainer 3012 is inserted into the upper receiver opening, leading with the bottom surface 3124, the retainer outer surface 3127 facing the opposing arm extensions 3066. The retainer 3012 is then lowered into the receiver 3010 as shown in phantom in FIG. 97 until the surface 3127 seats on the receiver surface 3100. Because the retainer surface 3127 outer radius is substantially the same of the receiver surface 3100 radius, force is required to press the retainer surface 3127 past the spheric edge 3098 of the receiver. Thereafter, the retainer 3012 is captured beneath the edge 3098 and the surface 3127 is in a tight or friction fit engagement with the receiver surface 3100, pivotable with respect to the receiver when some force is applied to move the retainer with respect to the receiver.

With reference to FIGS. 97 and 98, the shank 3004 is moved upwardly into the receiver lower opening 3110 and the shank head top surface 3036 is moved into the retainer central bore 3121. There after, the shank is rotated, mating the shank helical thread 3040 with the retainer cooperating thread form 3126 until the shank cylindrical surface 3038 is aligned with the retainer cylindrical surface 3125. With reference to FIG. 98, the shank 3004 and the retainer 3012 are now fully attached within the receiver 3010, with the retainer bottom surface 3124 abutting against the shank annular ledge surface 3044. During the mating of the retainer 3012 with the shank head 3008, the retainer is held firmly in place within the receiver cavity formed by the surface 3100 with the spheric edge 3098 prohibiting upward movement of the retainer 3012 out of the receiver 3010. It can be seen that the retainer outer surface 3127 has the same radius as the shank surface 3035 and that when the shank and attached retainer are pivoted both surfaces 3127 and 3035 are in a friction fit engagement with the receiver surface 3100 as described previously herein with respect to the single piece shank head 8 and the receiver 10, the shank 3004 and retainer 3012 being pivotable with respect to the receiver 3010 when some force is used to slide the retainer surface 3127 as well as the shank surface 3035 along the receiver surface 3100.

With further reference to FIG. 98, the insert 3014 is then loaded and positioned in a manner described previously with respect to the insert 14 and the receiver 10 and shown in FIGS. 25 and 26. At this time, the shank 3004 and attached retainer 3012 may be pivoted in a non-floppy manner to a variety angular positions with respect to the receiver, similar to that shown in FIGS. 91 and 92, for example.

With reference to FIG. 99, eventually the rod 3021 or other longitudinal connecting member and the closure 3018 are positioned and tightened in a manner identical to that described previously herein with respect to the rod 1021 and closure 1018 and with respect to FIG. 67. As shown in FIG. 99, the closure outer structure 3019 bottom surface 3206 engages the insert 3014 arm top surfaces 3166, pressing the insert downwardly into locking engagement with the retainer spherical outer surface 3127, the retainer surface 3127 and the shank surface 3035 being placed in locked frictional engagement with the receiver inner spherical surface 3100. Also with respect to FIG. 99, the rod is eventually fixed against the insert 3014 by direct pressure from the closure set screw 3020, the set screw bottom surface 3227 in frictional engagement with the rod cylindrical surface 3022. The inner set screw 3020 is rotated and moved downwardly into engagement with the rod 3021 in the same manner as described previously with respect to the closure set screw 1020 and the rod 1021 and with reference to FIG. 67.

With reference to FIG. 100, three alternative bone screw shanks are illustrated. The shanks are identical with the exception of the amount, if any of surface treatment in the form of grooves that are formed on the shank heads. For example, a shank 4004 is illustrated that is identical in form and function to the shank 4 previously described herein and shown in detail in FIGS. 2-4 with the exception of the groove coverage. Thus, the shank 4004 may be used in the assembly 1 in lieu of the shank 4. As the shank 4 has been fully described above, the shank 4004 will not be further described herein with the exception of identifying some of the features that are the same or substantially similar to the shank 4 features to facilitate further description of the assembly and operation of the shank in a bone screw 4001 shown in FIGS. 101-110. Thus, the shank 4004 includes a shank body 4006, an upper portion or head 4008, a head spherical surface 4034, a planar top surface 4036, upper ridges 4037, lower ridges 4038 and a smooth isthmus or strip 4040 between the ridges as well as a multi-lobular drive 4050 that are the same or substantially similar in form and function to the respective shank body 6, upper portion or head 8, head spherical surface 34, planar top surface 36, upper ridges 37, lower ridges 38, isthmus 40 and multi-lobular drive 50 previously described herein with respect to the shank 4 as well as other features described and shown with respect to the shank 4. The smooth isthmus 4040 of the shank 4004 is more narrow than the smooth isthmus 40 of the shank 4.

Also with reference to FIG. 100, an alternative bone screw shank 4004' is identical to the bone screw shank 4004 with the exception that an entire spherical surface 4034' is covered with grooves 4037'. An alternative bone screw shank 4004" is identical to the bone screw shank 4004 with the exception that an entire spherical surface 4034" is smooth.

With further reference to FIG. 100 and also with reference to FIGS. 101-104 and 109-110, the alternative bone screw assembly 4001 of an embodiment of the invention is shown that includes the shank 4004, a receiver 4010, and an insert 4014. With the exception of certain dimensions, the receiver 4010 is substantially similar to the receiver 10 previously described herein and shown in detail in FIGS. 5-7. The receiver 4010 differs from the receiver 10 in that the receiver 4010 has a slightly larger open channel and inner cavity than the receiver 10 allowing for a slightly lower profile of the shank 4004 within the receiver 4010 and slightly larger, stronger insert 4014 and closure 4018 than the insert 14 and closure 18 previously described herein. However, it is noted that the closure 4018 may be sized and shaped to cooperate with the assemblies 1, 1001, 2001 and 3001 previously described herein.

With particular reference to FIGS. 101-104, the receiver 4010 is substantially similar in form and function to the receiver 10 previously described herein. Thus, the receiver 4010 includes a base 4058 forming a cavity 4061, opposed arms 4060 forming a U-shaped channel 4062, a pair of opposed break-off extensions 4066, a helically wound guide and advancement structure 4072 on the on the extensions and the arms, a cylindrical inner surface 4092 starting at inner surfaces of the arms and partially defining the cavity, a ledge 4096, a spheric edge 4098 partially defining a spherical surface 4100, outer bottom surfaces 4102 and 4108, a lower opening 4110, as well as other receiver features that are the same as or substantially similar in form and function to the respective base 58 forming the cavity 61, opposed arms 60 forming the U-shaped channel 62, pair of opposed break-off extensions 66, helically wound guide and advancement structure 72 on the on the extensions and the arms, cylindrical inner surface 92 starting at inner surfaces of the arms and partially defining the cavity, the ledge 96, the spheric edge 98 partially defining the spherical surface 100, outer bottom surfaces 102 and 108, and lower opening 110 of the receiver 10 previously disclosed herein. It is noted that the guide and advancement structure 4072 is a flange form, similar to the structure 72 previously described herein. However, as the closure 4018 is a single start closure, the cooperating structure 4072 is oriented and shaped to provide a single discontinuous helical flange for mating engagement with the closure flange form.

With particular reference to FIGS. 101 and 102, as indicated above, the receiver 4010 is sized and shaped for receiving a slightly larger insert 4014 and closure 4018 than the receiver 10. However, the receiver 4010 is sized and shaped to receive and frictionally engage the shank 4004 that is the same size as the shank 4. Therefore, the cylindrical surface 4094 has a diameter greater than a diameter of the surface 94 of the receiver 10, but the receiver 4010 radiused or spherical surface 4100 has a radius that is the same as the radius of the spherical surface 100. Therefore, the receiver 4010 circular spheric edge 4098 has a edge diameter S' that is the same size as the spheric edge diameter S previously shown and discussed with respect to the receiver 10. In addition to having a larger diameter cylindrical surface 4094, the receiver 4010 also has a distance L' measured from the spheric edge 4098 to the bottom surface 4102 in a direction parallel to a central axis of the receiver 4010 that is shorter than a distance L of the receiver 10 also measured from the spheric edge 98 to the receiver bottom surface 102 in a direction parallel to the central axis of the receiver 10 (see FIG. 23). Thus, once assembled with the receiver 4010 and in frictional but movable engagement with the spherical seating surface 4100 (in a non-floppy manner), the shank head 4008 is seated relatively lower within the receiver 4010 than the shank head 8 in the receiver 10. An advantage of the resulting lower profile of the bone screw assembly 4001 is an increased angle of articulation of the shank 4004 in a direction opposite the sloping surface 4108 (i.e. towards the surface 4102) as shown, for example, in FIG. 109 that illustrates the shank 4004 disposed at a twenty-five degree angle with respect to the receiver 2010.

With reference to FIGS. 103 and 104, as stated above, the insert 4014 is almost identical to the insert 14 previously described herein with the exception that it has an outer dimension that is larger than the insert 14, thus the insert 4014 base and arms are thicker and thus stronger than the same counterparts of the insert 14. Thus, the insert 4014 includes an insert body 4156, upwardly extending opposed arms 4160, arm tops 4166, a bottom rim 4168, a through bore 4175, a saddle 4178, a lower saddle seat 4179, an inner cylindrical surface 4182 and a lower radiused or spherical surface 4184 that are the same in form and function as the respective insert body 56, upwardly extending opposed arms 60, arm tops 66, bottom rim 68, through bore 75, saddle 78, lower saddle seat 79, inner cylindrical surface 82 and lower radiused or spherical surface 84 of the insert 14 previously discussed herein with respect to the assembly 1. An outer diameter of the body 4156 and arms 4160 is sized to be closely received by the receiver arms and cylindrical surface 4094 and thus such outer diameter is greater than an outer diameter of the body 56 and arms 60 of the insert 14 of the assembly 1.

The rod 4021 having an outer cylindrical surface 4022 is identical to the rod 21 previously described herein. As with other bone anchor embodiments described herein, other types of longitudinal connecting members may be used with the assembly 4001 including, but not limited to other rods or bars of different shapes and hardness as well as longitudinal connecting members that are known in soft or dynamic stabilization techniques and apparatus.

With particular reference to FIGS. 104 to 108, the two-piece closure 4018 is somewhat similar to the closure 18 previously described herein as the closure 2018 includes an outer piece or portion 2019 and an inner piece or set screw 2020 similar in form and function to the respective outer structure 19 and inner structure 20 of the closure 18. However, as already mentioned, the closure structure 4019 has a single start flange form. Also, the closures differ somewhat with respect to driving structures. Thus, the closure 4018 will be described in greater detail below:

With particular reference to FIGS. 105-108, the illustrated outer fastener structure 4019 includes a through-bore 4204 extending along a central axis thereof and running completely through the fastener structure 4019 from a top surface 4205 to a bottom surface 4206. The bottom surface 4206 is substantially planar and annular and configured for being received between the receiver arms 4060 and for exclusively abutting against the substantially planar top surfaces 4166 of the insert arms 4160, the insert 4014 arms 4160 being configured to extend above the rod 4021 such that the closure surface 4206 is always spaced from the rod 4021 or other longitudinal connecting member portion received by the insert arms 4160 and located within the receiver 4010.

The closure or fastener structure 4019 is substantially cylindrical and has a helically sloping single flange form 4202 projecting substantially radially outwardly. The closure structure 4018 helically wound flange form 4202 thus has a single start 4203 best shown in FIG. 106. The shape of the flange form 4202 is the same or substantially similar to the shape of the form 202 previously described with respect to the closure structure 19. As the structure 4019 is rotated between the break-off extension arms of the receiver 4010, the helically wound structure 4202 advances the closure 4019 axially downwardly between the break-off extensions 4066 and then the arms 4060 and then presses the closure bottom surface 4206 firmly down upon the insert 4014 arm top surfaces 4166.

At the closure structure base or bottom surface 4206 and running to near the top surface 4205, the bore 4204 is substantially defined by a guide and advancement structure shown in the drawing figures as an internal V-shaped thread 4210. The thread 4210 is sized and shaped to receive the threaded set screw 4020 therein as will be discussed in more detail below. Although a traditional V-shaped thread 4210 is shown, it is foreseen that other types of helical guide and advancement structures may be used. Adjacent the closure top surface 4205, the bore 4204 is defined by a discontinuous cylindrical surface 4212 that runs from the top surface 4205 to a lower ledge or over-hang surface or surfaces 4213. In the illustrated embodiment the over-hang 4213 is a stepped surface that spans between the cylindrical surface 4212 and the v-thread 4210. The over hang surfaces 4213 act as a stop or abutment for the inner set screw 4020, preventing the screw 4020 from rotating upwardly and out of the structure 4019 at the top surface 4205.

With particular reference to FIGS. 105 and 107, formed in the top surface 4205 of the fastener 4019 is a tri-slotted internal drive 4215 made up of three evenly spaced radially outwardly extending slots 4216. Each of the slots 4216 extends outwardly from the cylindrical surface 4212 and runs to near the flange form 4202.

The up-loadable set screw 4020 has a substantially annular and planar top 4226 and a substantially annular planar bottom 4227 with a through bore, generally 4228, running through both the top and bottom thereof. The screw 4020 is substantially cylindrical in shape and coaxial with the outer fastener 4019. The screw 4020 includes an upper outer cylindrical surface 4230 adjacent a v-thread surface portion 4232 that runs substantially to the base or bottom surface 4227. The v-thread 4232 is sized and shaped to be received by and mated with the inner thread 4210 of the fastener 4019 in a nested, coaxial relationship. The bottom surface 4227 is sized and shaped to clear the insert 4014 arms 4160 and exclusively press upon the rod 4021 as shown, for example, in FIG. 104.

As illustrated, for example, in FIGS. 105-108, the set screw 4020 includes an internal drive feature 4240 that defines the through bore 4228 from near the top surface 4226 to near the bottom surface 4227 and is sized and shaped for a positive, non-slip engagement by a set screw installment and removal tool (not shown) that is inserted into the bore 4228. The drive feature 4240 is a poly drive, specifically, having a hexa-lobular geometry formed by a substantially cylindrical wall 4242 communicating with equally spaced radially outwardly extending (from the closure central axis) rounded cut-outs or lobes 4244. Although the hexa-lobular drive feature 4240 is preferred for torque sensitive applications as the lobes are able to receive increased torque transfer as compared to other drive systems, it is noted that other drive systems may be used, for example, a simple hex drive, star-shaped drive or other internal drives such as slotted, tri-wing, spanner, two or more apertures of various shapes, and the like. With reference to FIGS. 104, 107 and 108, the central set screw drive 4240 cooperates with the central internal bore 4204 of the fastener 4019 for accessing and uploading the set screw 4020 into the fastener 4019 prior to engagement with the bone screw receiver 4010. After the closure structure 4019 is inserted and rotated into the flange form 4072 of the bone screw receiver 4010, the set screw 4020 is rotated by a tool engaging the drive feature 4240 to place the set screw bottom 4227 into frictional engagement with the rod 4021 or other longitudinal connecting member such as shown in FIGS. 104, 109 and 110. Such frictional engagement is therefore readily controllable by a surgeon so that the rod 4021 may be readily be loosened and manipulated until late in the surgery, if desired. Thus, at any desired time, the set screw 4020 may be rotated to drive the screw 4020 into fixed frictional engagement with the rod 4021 without varying the angular relationship between the receiver 4010 and the bone screw shank 4004. The drive 4215 of the outer structure 4019 and the drive 4240 of the set screw 4020 are sized and shaped such that both drives can be accessed and driven individually by different drive tools at any time during the surgical procedure and also during any subsequent manipulation or removal of the rod or subsequent adjustment of an angle of inclination of the shank with respect to the receiver.

The receiver 4010, the shank 4004 and the compression insert 4014 are typically assembled in a manner identical to what has been described herein with respect to the receiver 10, shank 4 and compression insert 14. Thereafter, as previously described herein with respect to the bone screw assembly 1, the screw assembly 4001 made up of the shank 4004, receiver 4010 and insert 4014 is screwed into a bone, such as the vertebra 17, also as previously described with respect to the assembly 1. A variety of different angular or articulated positions of the shank 4004 with respect to the receiver 4010 are possible, some making full use of the sloped bottom surface 4108 as shown, for example in FIGS. 109 and 110. As shown in FIG. 104, after insertion of the rod 4021 and two-piece closure 2018, the break-off tabs 4066 are removed, details of which are also described with respect to the assembly 1.

With reference to FIGS. 111-125 an alternative embodiment of a two-piece, single start closure, generally 5018 according to the invention is shown with an open implant in the form of a polyaxial bone screw apparatus or assembly, generally 5001 (see, e.g., FIGS. 122, 123) that includes a shank 5004, that further includes a threaded body 5006 integral with an upwardly extending substantially spherical upper portion or head 5008; a receiver 5010 having a cavity or inner chamber for receiving the shank head 5008 communicating with an upper channel formed between opposed arms 5011 having top surfaces 5012, the receiver cavity further defined by a spherical seating surface 5013; and a compression or pressure insert 5014 having a lower curved or partially spherical surface 5015 engaging the shank head 5008 within the receiver cavity, the illustrated insert 5014 also defining an inner channel between opposed upright arms 5016, each having a top surface 5017.

The illustrated closure 5018 includes two pieces: an outer substantially cylindrical plug or fastener 5019 having an outer guide and advancement structure in the form of a single-start helically wound flange form and an inner v-thread sized and shaped for cooperation with a coaxial threaded inner plug or set screw 5020, the helically wound forms of both of the structures 5018 and 5019 having an axis of rotation A. The closure top 5018 is illustrated alone in FIGS. 111-116.

The outer structure 5019 of the closure top 5018 mates under rotation with the receiver 5010 having a central axis with the axis A being aligned with the receiver central axis, the structure 5019 pressing downwardly against the insert 5014 arm top surfaces 5017, the insert surface 5015 in turn pressing downwardly against the shank head 5008 that in turn frictionally engages the receiver 5010, locking the polyaxial mechanism of the bone anchor 5001, (i.e., fixing the shank 5004 at a particular desired angle with respect to the receiver 5010). A longitudinal connecting member such as a rod 5021 is captured within the receiver 5010 by the outer fastener 5019 but not fixed thereby and thus may be moved by sliding or rotation with respect to the receiver 5010, even when the outer fastener 5019 is pressed against the insert 5014, locking the polyaxial mechanism and thus allowing the screw 5001 to function as a mono-axial screw. The closure inner plug 5020 ultimately frictionally engages and presses against the rod 5021 so as to frictionally engage and fix the longitudinal connecting member 5021 against the insert 5014 and thus fix the member 5021 relative to a vertebra 5023.

The illustrated rod 5021 is hard, stiff, non-elastic and cylindrical, having an outer cylindrical surface 5022. However, a longitudinal connecting member for use with the assembly 5001 may take the form of an elastic or deformable rod or have a different cross-sectional geometry. The longitudinal connecting member may also be a part of a soft or dynamic system that may include hard or soft structure for attaching to the assembly 5001 and may further include a tensioned cord, elastic bumpers and spacers located between bone screws, for example. In the illustrated embodiment, the receiver 5010 and the shank 5004 cooperate in such a manner that the receiver 5010 and the shank 5004 can be secured at any of a plurality of angles, articulations or rotational alignments relative to one another and within a selected range of angles both from side to side and from front to rear, to enable flexible or articulated engagement of the receiver 5010 with the shank 5004 until both are locked or fixed relative to each other near the end of an implantation procedure.

Returning to FIGS. 111-116, the single-start closure outer fastener 5019 outer guide and advancement structure has a single helically wound form 5052 illustrated as a flange form that operably joins with a mating flange form structure 5053 disposed on the arms 5011 of the receiver 5010 to result in an interlocking guide and advancement structure or arrangement. Although a particular flange form structure and relationship is shown herein, it is noted that flange forms may be of a variety of geometries, including, for example, those described in Applicant's U.S. patent application Ser. No. 11/101,859 filed Apr. 8, 2005 (US Pub. No. 2005/0182410 published Aug. 18, 2005), which is incorporated by reference herein. The form 5052 includes a start surface or structure X as shown in FIG. 115, for example. The flanges 5052 and 5053 cooperate to helically guide the structure 5019 into the outer member or receiver 5010 when the structure 5019 is rotated and advanced into the arms of the outer member 5010. The inner and outer flanges 5052 and 5053 have respective splay regulating contours to control splay of the receiver arms 5011 when the fastener 5019 is strongly torqued therein. It is noted that the anti-splay structure provided by the mating flange forms 5052 and 5053 and the closure drive systems disclosed herein, such as the outer fastener drive pockets, may also be utilized on single-piece cylindrical plug-like closures as well as on other types of one and two piece nested closures, for example, those having a break-off head that separates from the closure when installation torque exceeds a selected level, similar to the closures disclosed in Applicant's U.S. Pat. No. 7,967,850 (see, e.g., FIGS. 22-25 and accompanying disclosure).

The illustrated fastener structure 5019 includes a through-bore, generally 5054, primarily defined by an inner v-thread extending along the fastener central axis and running completely through the fastener structure 5019 from a top surface 5055 to a bottom surface 5056. The bottom surface 5056 is substantially planar and annular and configured for being received between the receiver arms 5011 and for exclusively abutting against the substantially planar top surfaces 5017 of the insert arms 5016, the insert 5014 arms 5016 being configured to extend above the rod 5021 such that the closure surface 5056 is always spaced from the rod 5021 or other longitudinal connecting member portion received by the insert arms 5016 and located within the receiver 5010. With particular reference to FIG. 123, in the illustrated embodiment, the fastener bottom 5056 slopes slightly downwardly running in a direction towards the through bore 5054. Also with reference to FIGS. 122-124, the insert 5014 arm top surfaces 5017 are substantially planar and also slope downwardly slightly or gently (about two degrees) toward the insert central axis of rotation. The two-piece closure 5018 and bone screw 5001 components 5004, 5010 and 5014 may be made from a variety of materials, including, but not limited to, titanium, titanium alloys, stainless steel and cobalt chrome alloys.

In certain embodiments according to the invention, for example, as shown in FIG. 125, a fastener 5019' is shown that is identical to the fastener 5019 with the exception that a bottom surface 5056' is disposed substantially perpendicular to the fastener 5019' central axis and likewise, an alternative insert 5014' of an alternative bone anchor 5001' has arm top surfaces 5017' that are planar and positioned substantially perpendicular to the insert 5014' axis of rotation, the insert 5014' otherwise being identical to the insert 5014 previously described herein. In such embodiments, a preferable material for the insert 5014' is a cobalt chrome alloy. It has been found that when both the outer fastener 5019 and the insert 5014 are made from titanium, for example, twisting, grabbing, buckling and splaying may occur, believed to be caused at least in part due to the coefficient of friction of the fastener and insert materials (e.g., a surface of one titanium component grabbing or sticking to a surface of another titanium component). Therefore, when materials such as stainless steel and titanium alloys are desired for the insert 5014 because of other desirable attributes of those materials (e.g., flexibility, ductile nature, easily machinable, cut-able), the insert top surface 5017 may desirably include one ore more sloping or curving or contoured surfaces with cooperating sloping, curving or contoured surfaces on the fastener 5019 that control the insert arms 5016 and thus guard against unwanted splaying and buckling. On the other hand, it has been found that an insert 5014' made from a cobalt chrome alloy or other metal alloy that is harder than titanium or stainless steel does not twist, buckle grab a cooperating insert 5019' bottom surface 5056', even when the fastener 5019' is made from a softer material such as a titanium alloy. Therefore, in embodiments wherein the insert is made from a cobalt chrome alloy, a sloping, contoured or curved insert arm top surface may not be desired or required.

Returning again to FIGS. 111-116, at the closure structure base or bottom surface 5056 and running to near the top surface 5055, the bore 5054 is substantially defined by a guide and advancement structure shown in the drawing figures as an internal V-shaped thread 5060. The thread 5060 is sized and shaped to receive the threaded set screw 5020 therein as will be discussed in more detail below. Although a traditional V-shaped thread 5060 is shown, it is foreseen that other types of helical guide and advancement structures may be used for helically guiding and advancing the set screw 5020 into the outer fastener 5019. A preferred v-thread 5060 is relatively fine (more threads per axial distance) as compared to the outer flange form 5052. Furthermore, it has been found that the more fine the thread 5060, the better the thrust of the set screw 5020 and thrust rather than torque is a more relevant feature for such a small inner set screw as required by the dual screw design in order to keep the overall bone anchor a desirably small size. As will be discussed in greater detail below with respect to the inner set screw 5020, for dual closures of such a small size, if the set screw drive tool generates too much torque, often either the tool breaks or the tool strips the drive of the set screw. However, by increasing the number of threads per axial distance (in other words moving towards a thread form that is more fine and thus has a lower pitch) as compared to dual closures already known in the art, a desirable thrust results when the set screw/fastener combination has a very fine thread form connection even though this also means that the torque is relatively low.

Adjacent the closure top surface 5055, the thread 5060 is made discontinuous at four locations by a drive system, generally 61 made up of four evenly spaced driving pockets or apertures 5062 formed in the fastener top surface 5055. However, as the illustrated thread 5060 includes at least a portion thereof that extends all the way to the surface 5055 and also terminates at the bottom surface 5056, the set screw 5020 may be uploaded into the fastener 5019 at the bottom surface 5056 or downloaded into the fastener 5019 at the top surface 5055. In other embodiments of the invention, an overhang or other discontinuous cylindrical surface may be located near the top surface 5055, replacing some of the threaded surface 5060 and having a radius measured from the central axis A that is the same or less than a radius from the central axis to a crest the v-thread 5060. In such embodiments, such an overhang or cylindrical surface would act as a stop for the inner set screw or plug 5020, preventing the screw 5020 from rotating upwardly and out of the structure 5019 at the top surface 5055. In the illustrated embodiment, the central set screw 5020 may be rotated or screwed completely through the outer ring member or fastener 5020 in either direction.

Returning to the internal drive pockets 5062 best shown in FIGS. 111, 112, 114 and 116, the pockets 5062 may also be described as two cross-slots that extend through or across the bore 5054 and thus through the thread form 5060, but do not extend through the outer flange form 5052. The hollows or apertures 5062 may also be described as driving sockets that are each open in a radial direction. In other embodiments of the invention, greater or fewer numbers of pockets or cross-slots may be formed in the top surface 5055. For example, the outer fastener drive 5061 could be made up of three spaced cross-slots that terminate near the flange form 5052, or stated in other way, six equally spaced radial slots or pockets. With particular reference to FIG. 114, each pocket 5062 includes a substantially planar base or bottom tool abutment surface 5065, opposed and parallel planar driving faces or surfaces 5066 disposed perpendicular to the abutment surface 5065 and an outer wall 5067 that is also perpendicular to the abutment surface 5065 and is substantially cylindrical, the surface 5067 located near and substantially evenly spaced from the flange form 5052 and extending between the opposed driving faces 5066. Furthermore, in the illustrated embodiment, an additional lobe or recess defined by a curved wall 5070 is formed in the fastener top surface 5055, the wall 5070 terminating at the tool abutment surface 5065 and disposed perpendicular thereto, the wall enlarging and extending each of the drive pockets 5062 in a radially outwardly direction that is also located centrally along the pocket outer wall 5067 and thus substantially midway between the driving surfaces 5066. In the illustrated embodiment (see, for example, FIG. 112), each curved lobe wall 5070 extends to and partially through a root surface 5072 of the fastener flange form 5052, but does not extend through a crest surface 5073 or adjacent splay control surfaces thereof or even substantially into a driving flank 5074 or trailing flank 5074' thereof. Thus, the flange form anti splay surfaces and driving flanks that cooperate with surfaces of the receiver flange form 5053 are continuous and are not cut, broken or otherwise compromised. Similarly, if the outer fastener 5019 would have another type of form, such as an outer square thread form in lieu of the flange form 5052, the square thread form crest and driving flanks making contact with a cooperating square thread form of the receiver would also be continuous with only portions of the square thread form root being removed. In the illustrated embodiment, the centrally located lobes formed by the curved walls 5070 allow for an increased mass and thus increased strength of a fastener driver tool 5076 shown in FIGS. 113 and 117-121 and described in greater detail below. The walls 5070 provide for an increased contact between the driver 5076 and the fastener pockets 5062. Increased contact between the driver 5076 and the pockets 5062 may reduce the tendency of the driver 5076 to cam out of the fastener 5019 drive feature and provides for an improved fit, placement and secure engagement of the driver 5076 with respect to the drive pockets 5062. In some embodiments of the invention, the curved lobe walls 5070 may be placed closer to one or the other of the drive surfaces 5066 and thus may also further aid in rotation and driving the fastener 5019 into the receiver 5010. It is also noted that in other embodiments of the invention, the drive pockets 5062 do not include an outer lobe, such as the pockets shown in Applicant's provisional patent application Ser. No. 61/849,514 filed Jan. 28, 2013.

The up-loadable set screw 5020 has a substantially annular downwardly and outwardly sloping top 5086 and a substantially circular planar bottom 5087. The screw 5020 is substantially cylindrical in shape and coaxial with the outer fastener 5019. Originating at the top surface 5086 is a v-thread surface portion 5089 that terminates at a lower frusto-conical surface 5090 that runs to the base or bottom surface 5087. The v-thread 5089 is sized and shaped to be received by and mated with the inner thread 5060 of the fastener 5019 in a nested, coaxial relationship. The frusto-conical surface 5090 is sized and shaped to clear the insert 5014 arms 5016 and exclusively press upon the rod 5021 as indicated, for example, in FIG. 123.

As illustrated, for example, in FIGS. 111, 112, 114 and 116, the set screw 5020 includes a central aperture or internal drive feature, generally 5091, formed in the top 5086 and sized and shaped for a positive, non-slip engagement by a set screw installment and removal tool (not shown) that may be inserted through the bore 5054 of the fastener 5019 and then into the drive aperture 5091. The drive aperture 5091 is a poly drive, specifically, having a hexa-lobular geometry formed by a substantially cylindrical wall 5092 communicating with equally spaced radially outwardly extending (from the closure central axis) rounded cut-outs or lobes 5094. The wall 5092 and the lobes 5094 terminate at a substantially planar bottom driving tool seating or abutment surface 5096 having a central divot 5097 formed therein. Although the hexa-lobular drive feature 5091 is illustrated as it is currently preferred for torque sensitive applications as the lobes are able to receive increased torque transfer as compared to some other drive systems, it is noted that other drive systems may also be used in other embodiments, for example, a simple hex drive, star-shaped drive or other internal drives such as slotted, tri-wing, spanner, two or more apertures of various shapes, and the like.

The central set screw drive aperture 5091 cooperates with the central internal bore 5054 of the fastener 5019 for accessing and uploading or downloading the set screw 5020 into the fastener 5019 prior to or after engagement of the fastener 5019 with the bone screw receiver 5010. After the outer closure structure or fastener 5019 is inserted and rotated into the flange form 5053 of the bone screw receiver 5010, the set screw 5020 is rotated by a tool engaging the drive feature 5091 to place the set screw bottom 5087 into frictional engagement with the rod 5021 or other longitudinal connecting member. Such frictional engagement is therefore readily controllable by a surgeon so that the rod 5021 may be loosened and manipulated until late in the surgery, if desired. Thus, at any desired time, the set screw 5020 may be rotated to drive the screw 5020 into fixed frictional engagement with the rod 5021 without varying the angular relationship between the receiver 5010 and the bone screw shank 5004.

It is foreseen that the set screw 5020 may further include a cannulation through bore extending along a central axis thereof for providing a passage through the closure 5018 interior for a length of wire (not shown) inserted therein to provide a guide for insertion of the closure top into the receiver arms 5011. The base or bottom 5087 of the screw 5020 may further include a rim for engagement and penetration into the surface 5022 of the rod 5021 in certain embodiments of the invention.

As described above with respect to the inner thread 5060 of the fastener 5019, the outer thread 5089 of the set screw is a very fine v-thread sized and shaped to provide adequate thrust of the set screw 5020 against the rod 5021 without the torque requirements found in larger set screws of other dual or two piece closures. Because the outer fastener drive pockets 5062 are advantageously spaced inwardly from the outer fastener flange form 5052 and do not cut into or otherwise compromise the continuity and strength of the flange form 5052, the set screw 5020 is advantageously sized smaller than other known set screws in order to allow for the same or increased driving surface area for the driving surfaces 5066 of the pockets 5062 of the outer fastener 5019. In other known drive systems where the outer fastener drive consists of through slots, for example, there is adequate surface area for driving the outer fastener but the continuity and strength of the fastener outer flange form (or other type of outer helical guide and advancement structure) is compromised. Such is not desirable as the outer fastener typically includes some sort of splay control outer guide and advancement structure that keeps the receiver arms 5011 from splaying outwardly which results in unwanted loosening of the entire closure from the bone screw receiver 5010. It has been found by sizing the thread 5089 to be more fine, the smaller set screw 5020 performs as well as larger counterparts in other closure systems that include thread forms having a larger pitch than the pitch of the thread form 5089 and inner set screws having a diameter larger than a diameter of the set screw 5020.

With particular reference to FIGS. 113 and 117-121, the drive system 5061 that includes the pockets 5062 of the outer closure portion or fastener 5019 further includes the cooperating driver 5076. The driver 5076 is elongate and includes a shaft 5101 having a handle (not shown) at one end thereof and a drive feature, generally 5102 at an opposite end thereof. The drive feature 5102 includes four evenly spaced outer fastener drive prongs or extensions 5104 and a centrally located substantially cylindrical split extension portion 5106. The prongs 5104 and the extension 5106 are integral with the driver shaft 5101, the prongs 5104 each extending from a substantially planar shaft bottom or abutment surface 5108. Each of the prongs 5104 has a bottom substantially planar surface 5115, opposed side driving faces 5116 and a curved outer wall 5117, each outer wall further including an outer lobed surface 5120, the wall spanning between the driving faces 5116. Also spanning between the opposed, substantially planar and parallel driving faces 5116 is an inner cylindrical wall 5122. The inner extension portion 5106 is substantially cylindrical and has a discontinuous bottom surface 5125, the surface 5125 being split in half by a longitudinal slit, generally 5126 that terminates at and is partially defined by a rounded, key-hole-like surface 5127. An outer discontinuous cylindrical surface 5130 of the central extension is substantially evenly spaced from each prong inner cylindrical surface 5122 and terminates at an upper curved surface 5132 partially defining an annular groove, generally 5133, that is sized and shaped to receive and extend about the inner set screw 5020 structure located between the set screw drive feature 5091 and the outer v-thread 5089. The annular groove 5133 is also partially defined by each of the driving prong 5104 inner cylindrical walls 5122. As shown in FIG. 121, the groove 5132 extends upwardly beyond the driver abutment surface 5108 to provide adequate clearance for the inner set screw 5020 that initially may have the top surface 5086 thereof located above the top surface 5055 of the outer fastener 5019 as shown, for example, in FIG. 121. As best shown in FIGS. 120 and 121, the four prongs 5104 are sized and shaped to fit closely within the four fastener drive pockets 5062 with the outer lobes 5120 being closely received by the curved pocket walls 5070. The prong bottom surfaces 5115 abut against the pocket seating surfaces 5065 when the driver planar and annular surface 5108 abuts against the fastener top surface 5055. Thereafter, prong driving faces 5116 are placed into driving engagement with pocket surfaces 5066 when the driver 5076 is rotated by a user. Also during use, the flexible driver extension 5106 is received by the set screw drive aperture 5091, readily flexing inwardly at the slit 5126 during insertion and removal of the driver 5076 from the closure top 5018. Although the driver central extension 5106 is shown having an annular bulge or bump 5135 at a lower portion of the cylindrical surface 5130 located near the split bottom surface 5125, the bulge 5135 at most resiliently abuts against the cylindrical surface 5092 of the set screw 5020, but is not received into the set screw driving lobes 5094.

With reference to FIGS. 122 and 123, the receiver 5010, the shank 5004 and the compression insert 5014 are typically assembled at a factory setting that includes tooling for holding, alignment and manipulation of the component pieces, as well as crimping a portion of the receiver 5010 toward and against the insert 5014. In the illustrated embodiment, the shank 5004 is downloaded into the receiver followed by pressing the shank upper portion or head 5008 downwardly into the receiver cavity with some force. At this time, the shank 5004 is pivotable with respect to the receiver 5010 with some force. The compression insert 5014 is then downloaded into the receiver 5010 and lowered toward the shank head 5008 until the insert 5014 arms 5016 are adjacent the receiver arms and the insert inner surface 5015 is in engagement with the shank head spherical surface 5008. In some embodiments, the insert arms 5016 may need to be compressed slightly during assembly to clear inner surfaces of the receiver arms 5011. At this time, crimping wall portions of the receiver 5010 are pressed inwardly towards the insert 5014 and crimping wall material thus engages the insert walls at concave apertures thereof. The crimping wall material pressing against the insert 5014 at two opposed locations prohibits or reduces the degree that the insert 5014 may rotate with respect to the receiver axis. In the illustrated embodiment having the conical shaped recesses and crimping walls, any upward movement of the insert 5014 is also prohibited by the crimping wall material of the receiver walls. The resulting assembly 5001 is now in a desired position for shipping.

With reference to FIG. 122, the bone screw assembly made up of the shank 5004, receiver 5010 and insert 5014 is screwed into a bone, such as the vertebra 5023, by rotation of the shank 5004 using a suitable driving tool (not shown) that operably drives and rotates the shank body 5006 by engagement thereof at an internal drive of the body 5006. Specifically, the vertebra 5023 may be pre-drilled to minimize stressing the bone and have a guide wire (not shown) inserted therein to provide a guide for the placement and angle of the shank 5004 with respect to the vertebra. A further tap hole may be made using a tap with the guide wire as a guide. Then, the bone screw assembly 5001 is threaded onto the guide wire utilizing the bone screw cannulation bore by first threading the wire into the opening at the shank bottom and then out of the top opening at the drive feature. The shank 5004 is then driven into the vertebra using the wire as a placement guide. It is foreseen that the shank and other bone screw assembly parts, the rod 5021 (also having a central lumen in some embodiments) and the closure top 5018 having the central bore can be inserted in a percutaneous or minimally invasive surgical manner, utilizing guide wires. At this time, the receiver 5010 may be pivoted with respect to the implanted shank 5004 using some force, the bone screw head 5008 in close but movable (i.e., non-floppy engagement) with the surface 5015 of the insert 5014, allowing a user to manipulate the receiver 5010 with some force such that once a desired angle of orientation of the receive with respect to the shank 5004 is found, the receiver substantially remains in such desired position during the surgical procedure and prior to locking.

The rod 5021 is eventually positioned in an open or percutaneous manner in cooperation with the at least two bone screw assemblies 5001. The closure structure 5018, with the inner threaded plug 5020 already threadably mated either upwardly or downwardly with the outer structure 5019 as best shown in FIG. 116, is then inserted into and advanced between the arms 5011 of the receivers 5010 utilizing the tool 5076 as shown in FIGS. 119-121. The entire closure structure 5018 is rotated, mating the helical flange form 5052 with the receiver helical flange form 5053 using the tool driving portion 5102 received within and engaged with the drive pockets 5062 of the outer closure structure 5019 until a selected pressure is reached at which point the outer fastener structure bottom surface 5056 engages the upper arms surfaces 5017 of the insert 5014 and presses the insert 5014 spherical surface 5015 into locking engagement with the shank head 5008 spherical surface. As the closure structure 5019 presses downwardly on the compression insert further pressing and then locking the insert spherical surface 5015 against the shank spherical surface 5008 and the shank spherical surface 5008 against the receiver inner spherical surface 5013, the outer structure 5019 brings the rod 5021 cylindrical surface 5022 to a location at or near the insert saddle seat as shown in FIG. 123. After the rod 5021 is manipulated to a desired location and orientation, the inner set screw or plug 5020 is then rotated into locking engagement with the rod 5021 (not shown) by rotating a tool (not shown) inserted in the inner drive feature 5091.

If removal of the rod 5021 from any of the bone screw assemblies 5001 is necessary, or if it is desired to release the rod 5021 at a particular location, disassembly is accomplished by using the driving tool (not shown) that mates with the internal drive 5091 on the closure inner plug 5020. This may be all that is required to loosen and manipulate the rod 5021 without unlocking the polyaxial mechanism. However, if the rod 5021 is to be removed, the structure 5019 may be rotated utilizing the tool 5076 with the drive portion 5102 engaged in the pockets 5062 to rotate and remove the closure structure 5019 (alone or with the set screw 5020) from the cooperating receiver 5010. Disassembly is then accomplished in reverse order to the procedure described previously herein for the assembly.

It is to be understood that while certain forms of the present invention have been illustrated and described herein, it is not to be limited to the specific forms or arrangement of parts described and shown.

What is claimed is:

1. A pivotal bone anchor assembly for securing an elongate rod to a bone of a patient via a threaded closure top, the pivotal bone anchor assembly comprising:
 a receiver comprising:
  a vertical centerline axis;
  a base defining a lower portion of a central bore communicating with a bottom of the receiver through a lower opening, the lower portion including an interior seating surface extending circumferentially and continuously around the central bore above the lower opening and a lower cylindrical portion adjacent to and extending upward from the interior seating surface, with at least a portion of the bottom of the receiver being defined by a sloped planar surface oriented at a non-perpendicular angle with respect to the vertical centerline axis of the receiver and extending upward from a bottommost surface of the bottom of the receiver toward the interior seating surface to define an expanded portion of the lower opening; and
  first and second upright arms integrally formed with and extending upward from the base with opposed internal surfaces extending between a front face and a back face of the upright arms to define an open channel configured to receive the elongate rod, the central bore extending upward through the open channel to top surfaces of the upright arms and comprising the lower cylindrical portion having a first diameter, an upper wider portion above the lower cylindrical portion having a second diameter greater than the first diameter, and an upper internal thread form above the upper wider portion configured for engagement with the threaded closure top, each upright arm including:
   a side outer surface opposite the internal surface of the respective upright arm and extending downward across the base toward the bottom surface of the receiver;
   a break-off extension integrally formed with and extending upwardly from an inner edge portion on the top surface of the respective upright arm, the break-off extension having an internal thread form continuous with the upper internal thread form of the respective upright arm and an outer surface with a lower portion that tapers downwardly and inwardly toward the vertical centerline axis of the receiver and the inner edge portion; and
   a radiused non-threaded tool engagement groove extending horizontally and entirely across the side outer surface to the front face and the back face of the respective upright arm, each tool engagement groove being isolated from the central bore and being located below the top surface of each upright arm;
 a shank comprising a head having an at least partial spherical outer surface and an anchor portion opposite the head configured for attachment to the bone, the shank configured for positioning within the lower portion of the central bore with the shank extending downward through the lower opening and being pivotable with respect to the receiver in an unlocked configuration; and
 an insert having a body configured for positioning within the lower cylindrical portion of the central bore with a downwardly-opening concave surface configured to engage the head of the shank, and a pair of insert arms defining an upwardly-facing curvate surface between the insert arms configured to receive the elongate rod when the elongate rod is positioned in the open channel, with upper ends of the insert arms projecting laterally outward and configured for positioning within the upper wider portion of the central bore,
 wherein the expanded portion of the lower opening is configured to provide an increase in clearance for increased pivotal movement of the shank with respect to the receiver in the direction of the expanded portion of the lower opening when the head of the shank is received within the lower portion of the central bore of the receiver.

2. The pivotal bone anchor assembly of claim 1, wherein the bottommost portion of the bottom surface of the receiver further comprises a planar surface oriented perpendicular with respect to the vertical centerline axis.

3. The pivotal bone anchor assembly of claim 1, wherein the upper wider portion of the central bore comprises a pair of opposed recesses having substantially the same size and shape with respect to each other.

4. The pivotal bone anchor assembly of claim 1,
 wherein the at least partial spherical outer surface of the head of the shank defines a hemisphere plane perpendicular to a longitudinal axis of the shank at a maximum width along the longitudinal axis, and
 wherein the downwardly-opening concave surface of the insert does not extend below the hemisphere plane when the insert is engaged with the head of shank and the longitudinal axis of the shank is aligned with the vertical centerline axis of the receiver.

5. The pivotal bone anchor assembly of claim 1, wherein the interior seating surface of the lower portion of the central bore is a partial spherical surface.

6. The pivotal bone anchor assembly of claim 1, wherein the insert is configured to be top-loaded into the receiver.

7. The pivotal bone anchor assembly of claim 6, wherein the insert is configured to be twisted with an applied force into position within the central bore of the receiver relative to the vertical centerline axis.

8. The pivotal bone anchor assembly of claim 1, wherein the non-threaded tool engagement groove is curvate and extends circumferentially between the front face and the back face of the respective upright arm.

9. The pivotal bone anchor assembly of claim 1, wherein the top surface of each upright arm is substantially planar and perpendicular to the vertical centerline axis of the receiver.

10. The pivotal bone anchor assembly of claim 1, wherein the break-off extensions further comprise opposing outer surfaces that together define an outer diameter of the break-off extensions that is less than an outer diameter of the top surfaces on the upright arms of the receiver as defined between the opposite side outer surfaces of the upright arms.

11. The pivotal bone anchor assembly of claim 1,
 wherein the upper internal thread form of the central bore extends helically about and upwardly along inner surfaces of the break-off extensions to form the internal thread form of the break-off extensions, and
 wherein the internal thread forms include an inner recess formed at a location opposite an outer notch located at a juncture of the top surfaces on the uprights arm and the break-off extension and at least partially defined by the lower portion of the outer surface of the break-off extension that tapers downwardly and inwardly toward the vertical centerline axis of the receiver, the inner recess cutting into the internal thread forms in a direction transverse to a slope of the internal thread forms.

12. The pivotal bone anchor assembly of claim 11, wherein the direction of the inner recess is perpendicular to the vertical centerline axis of the receiver.

13. The pivotal bone anchor assembly of claim 1, wherein an upper portion of each break-off extension further comprises an upper frusto-conical outer surface tapering upwardly and inwardly to a top edge of the break-off extension.

14. The pivotal bone anchor assembly of claim 13, wherein an inner surface of the break-off extension opposite the upper frusto-conical outer surface is substantially cylindrical and without the internal thread form being formed therein.

15. The pivotal bone anchor assembly of claim 1 and further comprising a retainer, the retainer being positionable within the lower portion of the central bore prior to the head of the shank and configured to capture and hold the head of the shank within the lower portion of the central bore.

16. The pivotal bone anchor assembly of claim 1, wherein the shank includes a cannulation through-bore extending an entire length of the anchor portion of the shank along a longitudinal axis of the shank.

17. The pivotal bone anchor assembly of claim 1 and further comprising the threaded closure top and the elongate rod, wherein the threaded closure top is configured to be positioned into an upper portion of the central bore above the elongate rod positioned in the open channel so as to couple the elongate rod to the pivotal bone anchor assembly in a locked configuration.

* * * * *